US 8,815,951 B2

(12) United States Patent
Hammock et al.

(10) Patent No.: US 8,815,951 B2
(45) Date of Patent: *Aug. 26, 2014

(54) INHIBITORS OF EPOXIDE HYDROLASES FOR THE TREATMENT OF INFLAMMATION

(75) Inventors: Bruce D Hammock, Davis, CA (US); Jiang Zheng, Seattle, WA (US); Christophe Morisseau, Davis, CA (US); Kazuhiko Motoba, Kawachinagano (JP); Mehran F. Moghaddam, San Diego, CA (US); Babak Borhan, East Lansing, MI (US); David F. Grant, Storrs, CT (US); Jessica Greene, Oakland, CA (US); Marlene F. Sisemore, Davis, CA (US); James Sanborn, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/566,171

(22) Filed: Dec. 1, 2006

(65) Prior Publication Data

US 2007/0117782 A1 May 24, 2007

Related U.S. Application Data

(63) Continuation of application No. 11/189,964, filed on Jul. 25, 2005, now abandoned, and a continuation of application No. 11/240,444, filed on Sep. 29, 2005, now abandoned, said application No. 11/189,964 is a continuation of application No. 10/694,641, filed on Oct. 27, 2003, now abandoned, said application No. 11/240,444 is a continuation of application No. 10/694,641, which is a continuation of application No. 10/328,495, filed on Dec. 23, 2002, now Pat. No. 6,693,130, which is a continuation of application No. 09/721,261, filed on Nov. 21, 2000, now Pat. No. 6,531,506, which is a continuation-in-part of application No. 08/909,523, filed on Aug. 12, 1997, now Pat. No. 5,955,496.

(60) Provisional application No. 60/023,397, filed on Aug. 13, 1996.

(51) Int. Cl.
*A01N 47/28* (2006.01)
*A61K 31/17* (2006.01)

(52) U.S. Cl.
USPC .................................................. 514/588

(58) Field of Classification Search
USPC .................................................. 514/588
See application file for complete search history.

(56) References Cited

U.S. PATENT DOCUMENTS

| 4,024,258 | A | 5/1977 | Glamkowski et al. |
| 4,448,939 | A * | 5/1984 | Fasolka et al. ................ 525/474 |
| 5,445,956 | A | 8/1995 | Hammock et al. |
| 5,834,293 | A | 11/1998 | Capdevila et al. |
| 5,955,496 | A | 9/1999 | Hammock et al. |
| 5,962,455 | A | 10/1999 | Blum et al. |
| 6,015,818 | A | 1/2000 | Oku et al. |
| 6,150,415 | A | 11/2000 | Hammock et al. |
| 6,174,895 | B1 | 1/2001 | Hammock et al. |
| 6,531,506 | B1 | 3/2003 | Kroetz et al. |
| 6,534,282 | B2 | 3/2003 | Kim et al. |
| 6,693,130 | B2 | 2/2004 | Kroetz et al. |
| 6,699,832 | B2 | 3/2004 | Hadcock |
| 2003/0022929 | A1 | 1/2003 | Ingraham et al. |
| 2005/0222252 | A1 | 10/2005 | Hammock et al. |

FOREIGN PATENT DOCUMENTS

| EP | 0 401 903 | * 12/1990 |
| EP | 0 401 903 A2 | 12/1990 |
| JP | 7-304755 A | 11/1995 |
| WO | WO 98/06261 A1 | 2/1998 |

OTHER PUBLICATIONS

Danopoulos et. al., Journal of surgical onclogy (1982) 19:127-131.*
Eaton et. al., Expert Opinion on Investigational drugs (2002) 11:37-48.*
Aboab et. al., Expert Opinion on Emerging Drugs (2006) 11:7-22.*
Eaton et. al. (Expert Opinion in Investigational Drugs (2002) 11:37-48).*
Aboab et. al. (Expert Opinion on Emerging Drugs (2006) 11:7-22).*

(Continued)

*Primary Examiner* — Marcos Sznaidman
(74) *Attorney, Agent, or Firm* — DLA Piper LLP (US)

(57) ABSTRACT

The invention provides compounds that inhibit epoxide hydrolase in therapeutic applications for treating hypertension. A preferred class of compounds for practicing the invention have the structure shown by Formula 1

$$R_1 \diagdown X \diagup \underset{R_2}{\overset{\overset{Z}{\|}}{W}} \diagdown Y \diagup R_3 \\ R_4$$

wherein Z is oxygen or sulfur, W is carbon phosphorous or sulfur, X and Y is each independently nitrogen, oxygen, or sulfur, and X can further be carbon, at least one of $R_1$-$R_4$ is hydrogen, $R_2$ is hydrogen when X is nitrogen but is not present when X is sulfur or oxygen, $R_4$ is hydrogen when Y is nitrogen but is not present when Y is sulfur or oxygen, $R_1$ and $R_3$ is each independently $C_1$-$C_{20}$ substituted or unsubstituted alkyl, cycloalkyl, aryl, acyl, or heterocyclic.

11 Claims, 9 Drawing Sheets

(56) References Cited

OTHER PUBLICATIONS

Hele et. al. (Expert Opinion on Investigational Drugs (2003) 12:5-18).*

Cazzola et. al., Expert Opinion on Therapeutic Targets (2007) 11:1273-1286.*

Maarten, P.K., et al. (2007) Role of soluble epoxide hydrolase (Ephx2) in the generation and maintenance of high blood pressure in spontaneously hypertensive rats. Abstract SA-PO063. 2007 Renal Week meeting of the American Society of Nephrology (Nov. 2-5, 2007; San Francisco, CA). http://www.abstracts2view.com/asn/view.php?nu=ASN07L1_1860a; Accessed Jan. 25, 2008.

Maarten, P.K., et al. (2007) Role of soluble epoxide hydrolase (Ephx2) in the generation and maintenance of high blood pressure in spontaneously hypertensive rats [Poster]. 2007 Renal Week meeting of the American Society of Nephrology Nov. 2-5, 2007; San Francisco, CA.

Abdel-Aal and Hammock, "Use of Transition-State Theory in the Development of Bioactive Molecules," Chapter 9 in Bioregulators for Pest Control, ACS Symposium Series No. 276 (based on a sympsoium held Jun. 24-29, 1984), Hedin, ed., American Chemical Society, Washington, D.C., pp. 135-160, 1985.

Beetham et al., "cDNA Cloning and Expression of a Soluble Epoxide Hydrolase from Human Liver," Archives of Biochemistry and Biophysics, 305 (1), pp. 197-201, Aug. 15, 1993.

Black et al., "Selective Toxicity of N-Sulfenylated Derivatives of Insecticidal Methylcarbamate Esters," Journal of Agricultural and Food Chemistry, 21 (5), pp. 747-751, Sep./Oct. 1973.

Blee and Schuber, "Enantioselectivity of the Hydrolysis of Linoleic Acid Monoepoxides Catalized by Soybean Fatty Acids Epoxide Hydrolase," Biochemical and Biophysical Research Communications, 187 (1), pp. 171-177, Aug. 31, 1992.

Bone, Roger C., "Toward an Epidemiology and Natural History of SIRS (Systemic Inflammatory Response Syndrome)," JAMA, 268 (24), pp. 3452-3455, Dec. 1992.

Borhan et al., "Improved Radiolabeled Substrates for Soluble Epoxide Hydrolase," Analytical Biochemistry, 231, pp. 188-200, 1995.

Campbell, William B. et al.; "Identification of epoxyeicosatrienoic acids as endothelium-derived hyperpolarizing factors"; *Circulation Research*; Mar. 1996; pp. 415-423; vol. 78, No. 3.

Campbell, William B.; "New role for epoxyeicosatrienoic acids as anti-inflammatory mediators"; *Trends Pharmacol Sci*; Apr. 2000; pp. 125-127; vol. 21, No. 4.

Carretero, Oscar A and Suzanne Oparil; "Essential Hypertension: Part I: Definition and Etiology"; *Circulation*; 2000; pp. 329-335; vol. 101.

Carretero, Oscar A and Suzanne Oparil; "Essential Hypertension: Part II: Treatment"; *Circulation*; 2000; pp. 446-453; vol. 101.

Cheung et al., "Pesticide Immunoassay as a Biotechnology," Chapter 18 in The Impact of Chemistry on Biotechnology: Multidisciplinary Discussions, ASC Symposium Series No. 362, Phillips et al., eds., American Chemical Soceity, Washington, D.C., pp. 217-229, 1988.

Davis, B. B. et al.; "Attenuation of vascular smooth muscle cell proliferation by 1-cyclohexyl-3-dodecyl urea is independent of soluble epoxide hydrolase inhibition"; *American Society of Pharmacology and Experimental Therapeutics*; 2006; pp. 815-821; vol. 316, No. 2.

Debernard et al., "Expression and Characterization of the Recombinant Juvenile Hormone Epoxide Hydrolase (JHEH) from Manduca sexta," Insect Biochemistry and Molecular Biology, 28, pp. 409-419, 1998.

Demling, Robert H., "The Modern Version of Adult Respiratory Distress Syndrome," Annu. Rev. Med., 46, p. 193-202, 1995.

Dietze et al., "Inhibition of Epoxide Hydrolase from Human, Monkey, Bovine, Rabbit and Murine Liver by trans-3-Phenylglycidols," Comp. Biochem. Physiol., 104B (2), pp. 309-314, 1993.

Dietze et al., "Inhibition of Human and Murine Cytosolic Epoxide Hydrolase by Group-Selective Reagents," Comp. Biochem. Physiol., 104B (2), pp. 299-308, 1993.

Dietze et al., "Spectrophotometric Substrates for Cytosolic Epoxide Hydrolase," Analytical Biochemistry, 216, pp. 176-187, 1994.

Dietze et al., "The Interaction of Cytosolic Epoxide Hydrolase with Chiral Epoxides" Int. J. Biochem., 25 (1), pp. 43-52, 1993.

Fahmy and Fukuto, "N-Sulfinylated Derivatives of Methylcarbamate Esters," J. Agric. Food Chem., 29, pp. 567-572, 1981.

Fahmy et al., "Selective Toxicity of N,N'-Thiodicarbamates," J. Agric. Food Chem., 26 (3), pp. 550-556, 1978.

Fang, Xiang; "Soluble epoxide hydrolase: a novel target for the treatment of hypertension"; *Recent Patents on Cardiovascular Drug Discovery*; 2006; pp. 67-72; vol. 1.

Fornage, Myriam et al.; "Polymorphism in soluble epoxide hydrolase and blood pressure in spontaneously hypertensive rats"; *Hypertension*; 2002; pp. 485-490; vol. 40.

Grant et al., "Molecular Cloning and Expression of Murine liver Soluble Epoxide Hydrolase," J. Biol. Chem., 268 (23), pp. 17628-17633, Aug. 15, 1993.

Guo et al., "Characterization of a Tobacco Epoxide Hydrolase Gene Induced During the Resistance Response to TMV," The Plant Journal, 15 (5), pp. 647-656, 1998.

Hammock et al., "Epoxide Hydrolases," Chapter 18 in Comprehensive Technology, vol. 3 (Biotransformation), Guengerich, ed., Oxford: Pergamon, pp. 283-305, 1997.

Harms et al., "Expression of a Flax Allene Oxide Synthase cDNA Leads to Increased Endogenous Jasmonic Acid (JA) Levels in Transgenic potato Plants but Not to a corresponding Activation of JA-Responding Genes," The Plant Cell, 7, pp. 1645-1654, Oct. 1995.

Hitz et al., "Expression of a Δ6-Oleate Desaturase-Related Enzyme from Vernonia galamenensis Results in Vernolic Acid Accumulation in Transgenic Soybean," Abstract from the 13th International Symposium of Plant Lipids, Sevilla, Spain, Jul. 5-10, 1998.

Jojima et al., "Sugar, Glyceryl, and (Pyridylalkoxy)sulfinyl Derivatives of Methylcarbamate Insecticides," J. Agric. Food Chem., 31, pp. 613-620, 1983.

Kayser et al., "Composition of the Essential Oils of Pelargonium sidoides DC. and Palargonium reniforme Curt," Flavour and Fragrance Journal, 13, pp. 209-212, 1998.

Kiyosue et al., "Characterization of an *Arabidopsis* cDNA for Soluble Epoxide Hydrolase Gene that is Inducible by Auxin and Water Stress," The Plant Journal, 6 (2), pp. 259-269, 1994.

Kozak et al., "Inhibitors of Alternative Pathways of Arachidonate Metabolism Differentially Affect Fever in Mice," Am. J. Physiol., 275, pp. 1031-1040, 1998.

Kroetz, Deanna L. et al.; "Developmentally regulated expression of the *CYP4A* genes in the spontaneoulsy hypertensive rat kidney"; *Molecular Pharamcology*; 1997; pp. 365-372; vol. 52.

Lee et al., "Identification of Non-Heme Diiron Proteins that Catalyze Triple Bond and Epoxy Group Formation," Science, 280, pp. 915-918, May 8, 1998.

Makita, Keiko et al.; "Cytochrome P450, the arachidonic acid cascade, and hypertension: new vistas for an old enzyme system"; *FASEB J*; 1996; pp. 1456-1463; vol. 10.

Makita, Keiko et al.; "Experimental and/or genetically controlled alterations of the renal microsomal cytochrome P450 epoxygenase induce hypertension in rats fed a high salt diet"; *J. Clin. Invest.*; 1994; pp. 2414-2420; vol. 94.

Moghaddam et al., "Bioactivation of Leukotoxins to Their Toxic Diols by Epoxide Hydrolase," Nature Medicine, 3 (5), pp. 562-566, May 1997.

Moghaddam et al., "Novel Metabolic Pathways for linoleic and Arachidonic Acid Metabolism," Biochimica et Bio-physica Acta, 1290, pp. 327-339, 1996.

Morisseau et al., "Mechanism of Mammalian Soluble Epoxide Hydrolase Inhibition by Chalcone Oxide Derivatives," Archives of Biochemistry and Biophysics, 356 (2), pp. 214-228, Aug. 15, 1998.

Morisseau, Christophe et al.; "Potent area and carbamate inhibitors of soluble epoxide hydrolases"; *Proc. Natl. Acad. Sci. U.S.A.*; Aug. 1999; pp. 8849-8854; vol. 96.

Mullin and Hammock, "Chalcone Oxides-Potent Selective Inhibitors of Cytosolic Epoxide Hydrolase," Archives of Biochemistry and Biophysics, 216 (2), pp. 423-439, Jul. 1982.

(56) References Cited

OTHER PUBLICATIONS

Mullin, Christopher A., "Adaptive Relationships of Epoxide Hydrolase in Herbivorous Arthropods," Journal of Chemical Ecology, 14 (10), pp. 1867-1888, 1988.
Mumby and Hammock, "Stability of Epoxide-Containing Juvenoids to Dilute Aqueous Acid," Agricultural and Food Chemistry, 27 (6), pp. 1223-1228, Nov./Dec. 1979.
Murray et al., "The Expression of Cytochrome P-450, Epoxide Hydrolase, and Glutathione S-Transferase in Hepatocellular Carcinoma," Cancer, 71 (1), pp. 36-43, Jan. 1, 1993.
Murray et al., "The Immunohistochemical Localization of Drug-Metabolizing Enzymes in Prostate Cancer," Journal of Pathology, 177, pp. 147-152, 1995.
Omata, K. et al.; "Age-related changes in renal cytochrome P-450 arachidonic acid metabolism in spontaneously hypertensive rats"; *Am. J. Physiol.*; Jan. 1992; pp. F8-F16; vol. 262, No. 1 Pt. 2.
Pinot et al., "Characterization of Epoxide Hydrolase Activity in *Alternaria alternata* f. sp. *lycopersici*. Possible Involvement in Toxin Production," Mycopathologia, 140, pp. 51-58, 1997.
Prestwich and Hammock, "Rapid Purification of Cytosolic Epoxide Hydrolase from Normal and Clofibrate-Treated Animals by Affinity Chromatography," Proc. Natl. Acad. USA. 82, pp. 1663-1667, Mar. 1985.
Stapleton et al., "Cloning and Expression of Soluble Epoxide Hydrolase from Potato," The Plant Journal 6 (2), pp. 251-258, 1994.
Stark et al., "Comparison of Fatty Acid Epoxide Hydrolase Activity in Seeds from Different Plant Species," Phytochemistry, 38 (1), pp. 31-33, 1995.
Su, Ping et al.; "Inhibition of renal arachidonic acid ω-hydrolase acitvity with ABT reduces blood pressure in the SHR"; *Am. J. Physiol.*; 1998; pp. R426-R438; vol. 275.
Taton et al., "Inhibition of Higher Plant 2,3-Oxidosqualene Cyclases by Nitroben-Containing Oxidosqualene Analogues," Phytochemistry, 43 (1), pp. 75-81, 1996.
The Merck Manual, "Hypertension", Fifteenth Edition, 1987.
Theyer et al., "Role of the MDR-1-Encoded Multiple Drug Resistance Phenotype in Prostate Cancer Cell Lines," The Journal of Urology, 150, pp. 1544-1547, Nov. 1993.
Wixtrom and Hammock, "Membrane-Bound and Soluble—Fraction Epoxide Hydrolases: Methodological Aspects," in Biochemical Pharmacology and Toxicology, vol. 1: Methodological Aspects of Drug Metabolizing Enzymes, (Zakin and Vessey, eds.), New York: John Wiley & Sons, pp. 1-93, 1985.
Wixtrom et al., "Affinity Purification of Cytosolic Epoxide Hydrolase Using Derivatized Epoxy-Activated Sepharose Gels," Analytical Biochemistry, 169, pp. 71-80, 1988.
Yu, Z et al.; "Antihypertensive effect of soluble epoxide hydrolase (sEH) inhibition"; *Clinical Pharmacology and Therapeutics*; Feb. 2000; p. 128 (Abstract PII-53); vol. 67, No. 2.
Zeldin, Darryl C.; "Regio-and enantiofacial selectivity of epoxyeicosatrienoic acid hydration by cytosolic epoxide hydrolase"; *The Journal of Biological Chemistry*; Mar. 25, 1993; pp. 6402-6407; vol. 268, No. 9.
Zou, A.P. et al.; "20-HETE is an endogenous inhibitor of the large-conductance $CA^{2+}$-activated $K^+$ Channel in renal arterioles"; *Am. J. Physiol.*; Jan. 1996; pp. R228-R237; vol. 270, No. 1 pt 2.
Chemical Abstracts, vol. 79, No. 19. Abstract No. 115883: Zikan, et al.; "Drugs with antineoplastic effects. LIV Amides of gamma-oxo-gamma-(3-pyridyl)butyric acid"; *Cesk. Farm.* 22(4): 166-168 (Czech) 1973.
Paget et al.; "Heterocyclic Substituted Ureas. I. Immunosuppression and Virus Inhibition by Benzimidazolyrueas"; *J. Med. Chem.*; 12(5): 1010-1015 (1969).
Extended European Search Report for EP 07014966.1, dated Dec. 14, 2009 (8 pages).
Office Communication from U.S. Appl. No. 10/694,641, dated Jun. 22, 2010 (7 pages).
Inceoglu et al., "Analgesia mediated by soluble epoxide hydrolase inhibitors is dependent on cAMP", *Proc Natl Acad Sci USA*. Mar. 22, 2011;108(12):5093-7. Epub Mar. 7, 2011, pp. 1-13.
Morin et al., "17, 18-Epoxyeicosatetraenoic Acid Targets PPAR and p38 Mitogen-Activated Protein Kinase to Mediate Its Anit-inflammatory Effects in the Lung", Role of Soluble Epoxide Hydrolase, *Am J Respir Cell Mol Biol*, vol. 43, pp. 564-575, 2010.
Schmelzer et al., "Soluble epoxide hydrolase is a therapeutic target for acute inflammation", *Proc Natl Acad Sci USA*, Jul. 12, 2005, vol. 102, No. 28, 9772-9777.
Smith et al., "Attenuation of tobacco smoke-induced lung inflammation by treatment with a soluble epoxide hydrolase inhibitor", *Proc Natl Acad Sci USA*, Feb. 8, 2005, vol. 102, No. 6, 2186-2191.
J. Yang et al., "Soluble Expoxide Hydrolase is a Novel Therapeutic Target in Asthma by Modulating the Inflammatory Response", *Am J Respir Crit Care Med* 181; 2010, A4241.

* cited by examiner

INHIBITORS OF EPOXIDE HYDROLASES FOR THE TREATMENT OF INFLAMMATION

CROSS-REFERENCES TO RELATED APPLICATIONS

This application is a continuation of U.S. application Ser. No. 11/189,964, filed Jul. 25, 2005, and Ser. No. 11/240,444, filed Sep. 29, 2005, which are both a continuation of U.S. application Ser. No. 10/694,641, filed Oct. 27, 2003, which is a continuation of U.S. application Ser. No. 10/328,495, filed Dec. 23, 2002, now U.S. Pat. No. 6,693,130, which is a continuation of U.S. application Ser. No. 09/721,261, filed Nov. 21, 2000, now U.S. Pat. No. 6,531,506, which is a continuation-in-part of U.S. application Ser. No. 09/252,148, filed Feb. 18, 1999, now U.S. Pat. No. 6,150,415, which is a continuation-in-part of U.S. application Ser. No. 08/909,523, filed Aug. 12, 1997, now U.S. Pat. No. 5,955,496, which claims the benefit of U.S. Provisional Application No. 60/023,397, filed Aug. 13, 1996. The disclosures of each of the aforementioned applications are herein incorporated by reference in their entirety and for all purposes.

STATEMENT AS TO RIGHTS TO INVENTIONS MADE UNDER FEDERALLY SPONSORED RESEARCH AND DEVELOPMENT

This invention was made with Government support under Grant Nos. HL53994, ES02710, and ES04699 awarded by the National Institutes of Health.

BACKGROUND OF THE INVENTION

1. Field of the Invention

The present invention generally relates to methods of treating hypertension using inhibitors of epoxide hydrolases. Preferred inhibitors include compounds, such as ureas, amides, and carbamates that can interact with the enzyme catalytic site and mimic transient intermediates. Other useful inhibitors include glycodiols and chalcone oxides which can interact with the enzyme as irreversible inhibitors.

2. Background of the Invention

Hypertension is the most common risk factor for cardiovascular disease, the leading cause of death in many developed countries. Essential hypertension, the most common form of hypertension, is usually defined as high blood pressure in which secondary causes such as renovascular disease, renal failure, pheochromocytoma, aldosteronism, or other causes are not present (for a discussion of the definition and etiology of essential hypertension see, Carretero and Oparil *Circulation* 101:329-335 (2000) and Carretero, O. A. and S. Oparil. *Circulation* 101:446-453 (2000).

A combination of genetic and environmental factors contribute to the development of hypertension and its successful treatment is limited by a relatively small number of therapeutic targets for blood pressure regulation. Renal cytochrome P450 (CYP) eicosanoids have potent effects on vascular tone and tubular ion and water transport and have been implicated in the control of blood pressure (Makita et al. *FASEB J* 10:1456-1463 (1996)). The major products of CYP-catalyzed arachidonic acid metabolism are regio- and stereoisomeric epoxyeicosatrienoic acids (EETs) and 20-hydroxyeicosatetraenoic acid (20-HETE). 20-HETE produces potent vasoconstriction by inhibition of the opening of a large-conductance, calcium-activated potassium channel leading to arteriole vascular smooth muscle depolarization (Zou et al. *Am J. Physiol.* 270:R228-237 (1996)). In contrast, the EETs have vasodilatory properties associated with an increased open-state probability of a calcium-activated potassium channel and hyperpolarization of the vascular smooth muscle and are recognized as putative endothelial derived hyperpolarizing factors (Campbell et al. *Cir. Res.* 78:415-423 (1996)). Hydrolysis of the EETs to the corresponding dihydroxyeicosatrienoic acids (DHETs) is catalyzed largely by soluble epoxide hydrolase (sEH) (Zeldin et al. *J. Biol. Chem.* 268: 6402-64-07 (1993)).

Recent studies have indicated that renal CYP-mediated 20-HETE and EET formation are altered in genetic rat models of hypertension and that modulation of these enzyme activities is associated with corresponding changes in blood pressure (Omata et al. *Am J Physiol* 262:F8-16 (1992); Makita et al. *J Clin Invest* 94:2414-2420 (1994); Kroetz et al. *Mol Pharmacol* 52:362-372 (1997); Su, P. et al., *Am J Physiol* 275, R426-438 (1998)). Modulation of the CYP pathways of arachidonic acid metabolism as a means to regulate eicosanoid levels is limited by multiple isoforms contributing to a single reaction and the general lack of selectivity of most characterized inhibitors and inducers. Similarly, modulating EET levels by regulation of their hydrolysis to the less active diols has not been considered in light of concerns that EETs are involved in many physiological processes. (Campbell, *Trends Pharmacol Sci* 21:125-7 (2000)).

SUMMARY OF THE INVENTION

The present invention provides methods of treating hypertension by administering to a patient a therapeutically effective amount of an inhibitor of epoxide hydrolase. A preferred class of compounds for practice in accordance with the invention has the structure shown by Formula 1.

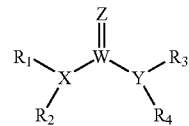

FORMULA 1 wherein Z is oxygen or sulfur, W is carbon phosphorous or sulfur, X and Y is each independently nitrogen, oxygen, or sulfur, and X can further be carbon, at least one of $R_1$-$R_4$ is hydrogen, $R_2$ is hydrogen when X is nitrogen but is not present when X is sulfur or oxygen, $R_4$ is hydrogen when Y is nitrogen but is not present when Y is sulfur or oxygen, $R_1$ and $R_3$ are each independently a substituted or unsubstituted alkyl, haloalkyl, cycloalkyl, aryl, acyl, or heterocyclic.

Preferred compounds of the invention have an $IC_{50}$ (inhibition potency or, by definition, the concentration of inhibitor which reduces enzyme activity by 50%) of less than about 500 µM. Exemplary compounds of the invention are listed in Table 1. The Table shows inhibition of recombinant mouse sEH (MsEH) and Human sEH (HsEH). The enzyme concentrations were 0.13 and 0.26 micromolar respectively

TABLE 1

Inhibition of MsEH (0.13 μM) and HsEH (0.2 μM)

| Structure inhibitors | nb | Mouse sEH IC$_{50}$ (μM)* | Human sEH IC$_{50}$ (μM)* |
|---|---|---|---|
| heptyl methyl carbamate | 72 | 0.11 ± 0.01 | 0.48 ± 0.01 |
| nonyl N-methylcarbamate | 248 | 0.33 ± 0.05 | 2.9 ± 0.6 |
| cyclohexyl cyclohexylcarbamate | 42 | 0.06 ± 0.01 | 0.13 ± 0.01 |
| 2-(hydroxymethyl)phenyl cyclohexylcarbamate | 224 | 0.99 ± 0.02 | 0.32 ± 0.08 |
| menthyl cyclohexylcarbamate | 225 | 0.84 ± 0.10 | 1.05 ± 0.03 |
| 4-cyclohexylbutyl cyclohexylcarbamate | 276 | 1.1 ± 0.1 | 0.34 ± 0.02 |
| 3-methylbut-3-enyl cyclohexylcarbamate | 277 | 0.12 ± 0.01 | 0.22 ± 0.02 |
| 4-(4-nitrophenyl)butyl cyclohexylcarbamate | 460 | 0.10 ± 0.02 | 0.18 ± 0.01 |
| naphthalen-2-yl cyclohexylcarbamate | 110 | 0.21 ± 0.01 | 0.35 ± 0.01 |

TABLE 1-continued

Inhibition of MsEH (0.13 μM) and HsEH (0.2 μM)

| Structure inhibitors | nb | Mouse sEH IC$_{50}$ (μM)* | Human sEH IC$_{50}$ (μM)* |
|---|---|---|---|
| | 259 | 0.45 ± 0.09 | 0.10 ± 0.02 |
| | 260 | 0.06 ± 0.01 | 0.10 ± 0.01 |
| | 261 | 0.08 ± 0.01 | 0.12 ± 0.01 |
| | 262 | 0.05 ± 0.01 | 0.10 ± 0.02 |
| | 263 | 3.0 ± 0.3 | 0.33 ± 0.06 |
| | 255 | 0.48 ± 0.07 | 2.88 ± 0.04 |
| | 514 | 0.27 ± 0.01 | |
| | 515 | 0.19 ± 0.05 | |

TABLE 1-continued

Inhibition of MsEH (0.13 μM) and HsEH (0.2 μM)

| Structure inhibitors | nb | Mouse sEH IC$_{50}$ (μM)* | Human sEH IC$_{50}$ (μM)* |
|---|---|---|---|
| [cyclohexyl-NH-C(=O)-CH$_2$-cyclohexyl] | 187 | 0.05 ± 0.01 | 0.42 ± 0.03 |
| [cyclohexyl-C(=O)-NH-CH$_2$-cyclohexyl] | 374 | 0.25 ± 0.01 | 2.03 ± 0.07 |
| [cyclohexyl-NH-C(=O)-(CH$_2$)$_3$-phenyl] | 381 | 0.06 ± 0.01 | 0.68 ± 0.03 |
| [cyclohexyl-N=C=N-cyclohexyl] |  | 0.25 ± 0.02 | 0.47 ± 0.01 |
| [propyl-NH-C(=O)-NH-cyclododecyl] | 189 | 0.80 ± 0.03 | 1.0 ± 0.2 |
| [tert-octyl-NH-C(=O)-NH-adamantyl] | 375 | 0.18 ± 0.01 | 0.11 ± 0.01 |
| [hexyl-NH-C(=O)-NH-phenyl] | 157 | 0.85 ± 0.01 | 1.43 ± 0.03 |
| [hexyl-NH-C(=O)-NH-2-naphthyl] | 143 | 1.0 ± 0.1 | 0.57 ± 0.01 |
| [hexyl-NH-C(=O)-NH-(3-chlorophenyl)] | 178 | 0.31 ± 0.01 | 0.25 ± 0.01 |

TABLE 1-continued

Inhibition of MsEH (0.13 μM) and HsEH (0.2 μM)

| Structure inhibitors | nb | Mouse sEH IC$_{50}$ (μM)* | Human sEH IC$_{50}$ (μM)* |
| --- | --- | --- | --- |
| heptyl-NH-C(O)-NH-propyl | 380 | 0.73 ± 0.03 | 0.68 ± 0.03 |
| heptyl-NH-C(O)-NH-butyl | 125 | 0.09 ± 0.01 | 0.72 ± 0.02 |
| heptyl-NH-C(O)-NH-isopropyl | 183 | 1.06 ± 0.07 | 5.9 ± 0.3 |
| heptyl-NH-C(O)-NH-hexyl | 175 | | 0.24 ± 0.01 |
| octyl-NH-C(O)-NH-cyclobutyl | 181 | 0.52 ± 0.02 | 1.71 ± 0.23 |
| octyl-NH-C(O)-NH-cyclohexyl | 168 | 0.06 ± 0.01 | 0.12 ± 0.01 |
| octyl-NH-C(O)-NH-phenyl | 151 | 2.29 ± 0.03 | 0.58 ± 0.01 |
| octyl-NH-C(O)-NH-(3-chlorophenyl) | 170 | 0.12 ± 0.01 | 0.18 ± 0.01 |
| octyl-NH-C(O)-NH-propyl | 429 | 0.38 ± 0.04 | 1.7 ± 0.4 |
| nonyl-NH-C(O)-NH-cyclohexyl | 153 | 0.06 ± 0.01 | 0.10 ± 0.01 |

TABLE 1-continued
Inhibition of MsEH (0.13 µM) and HsEH (0.2 µM)
| Structure inhibitors | nb | Mouse sEH IC$_{50}$ (µM)* | Human sEH IC$_{50}$ (µM)* |
|---|---|---|---|
| 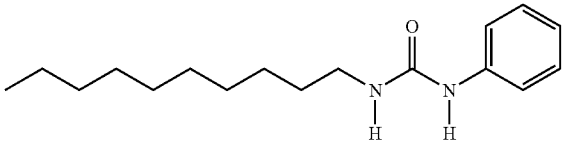 [SMILES: CCCCCCCCCCNC(=O)Nc1ccccc1] | 148 | 0.21 ± 0.01 | 0.61 ± 0.02 |
| 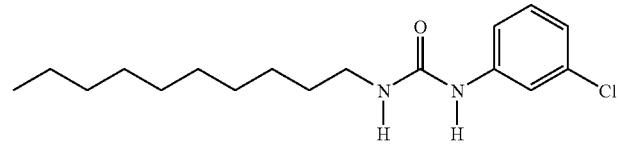 [SMILES: CCCCCCCCCCNC(=O)Nc1cccc(Cl)c1] | 172 | 0.12 ± 0.01 | 0.30 ± 0.01 |
| 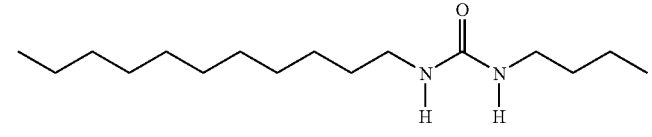 [SMILES: CCCCCCCCCCCNC(=O)NCCCC] | 556 | 0.20 ± 0.02 | 0.74 ± 0.07 |
| 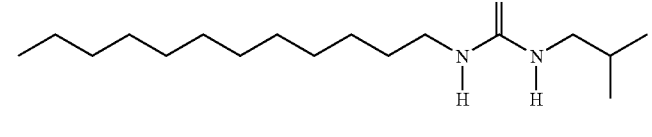 | 478 | 0.05 ± 0.01 | 0.26 ± 0.02 |
| 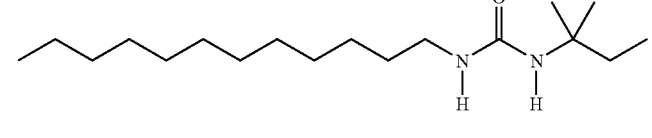 | 562 | 0.5 ± 0.1 | 15 ± 3 |
| 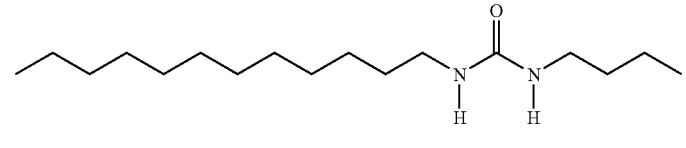 [SMILES: CCCCCCCCCCCCNC(=O)NCCCC] | 531 | 0.14 ± 0.02 | 0.64 ± 0.03 |
| 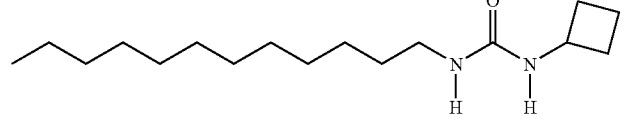 | 504 | 0.8 ± 0.1 | 23 ± 4 |
| 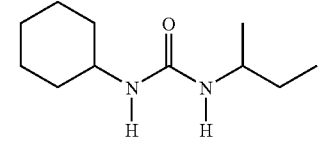 | 479 | 0.60 ± 0.06 | 5.0 ± 0.1 |
| 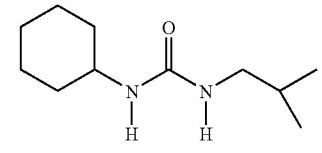 | 103 | 0.12 ± 0.01 | 2.2 ± 0.1 |
| 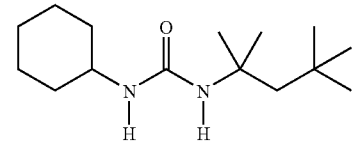 [SMILES: CC(C)(C)CC(C)(C)NC(=O)NC1CCCCC1] | 347 | 0.07 ± 0.01 | 3.10 ± 0.07 |

TABLE 1-continued
Inhibition of MsEH (0.13 µM) and HsEH (0.2 µM)
| Structure inhibitors | nb | Mouse sEH IC$_{50}$ (µM)* | Human sEH IC$_{50}$ (µM)* |
|---|---|---|---|
| 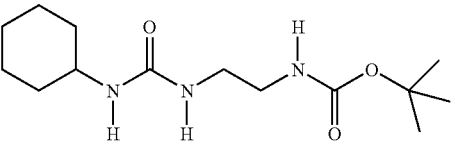 [SMILES: CC(C)(C)OC(=O)NCCNC(=O)NC1CCCCC1] | 124 | 0.05 ± 0.01 | 0.14 ± 0.01 |
| 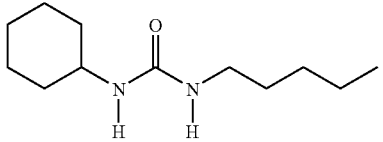 | 509 | 0.06 ± 0.01 | 0.92 ± 0.08 |
| 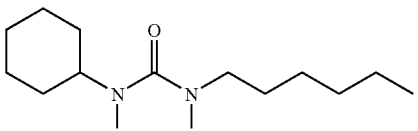 | 286 | 0.11 ± 0.03 | 0.07 ± 0.02 |
| 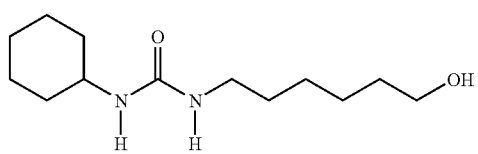 [SMILES: O=C(NCCCCCCO)NC1CCCCC1] | 344 | 0.05 ± 0.01 | 2.50 ± 0.08 |
| 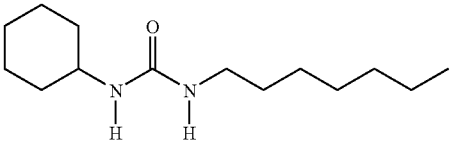 [SMILES: CCCCCCCNC(=O)NC1CCCCC1] | 508 | 0.05 ± 0.01 | 0.10 ± 0.01 |
| 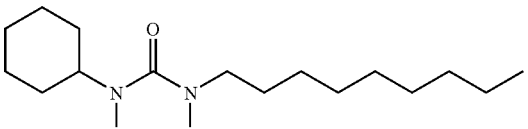 | 473 | 0.05 ± 0.01 | 0.10 ± 0.01 |
| 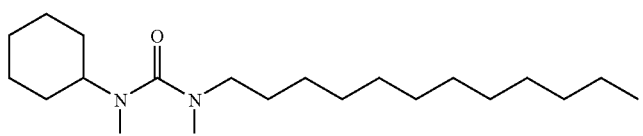 | 297 | 0.05 ± 0.01 | 0.10 ± 0.01 |
| 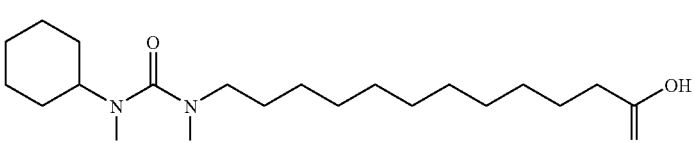 | 425 | 0.05 ± 0.01 | 0.10 ± 0.01 |
| 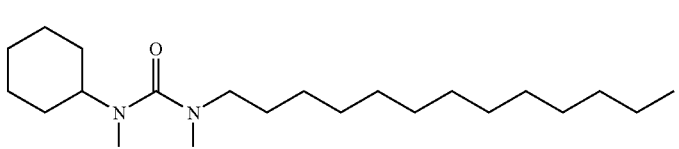 | 354 | 0.05 ± 0.01 | 0.10 ± 0.01 |

TABLE 1-continued
Inhibition of MsEH (0.13 μM) and HsEH (0.2 μM)
| Structure inhibitors | nb | Mouse sEH IC$_{50}$ (μM)* | Human sEH IC$_{50}$ (μM)* |
|---|---|---|---|
| 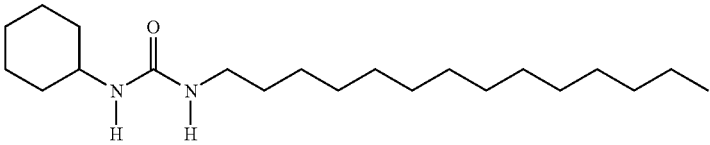 [SMILES: CCCCCCCCCCCCCCNC(=O)NC1CCCCC1] | 477 | 0.11 ± 0.01 | 0.24 ± 0.01 |
| 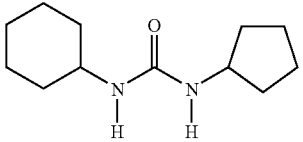 [SMILES: O=C(NC1CCCCC1)NC1CCCC1] | 23 | 0.10 ± 0.01 | 1.69 ± 0.05 |
| 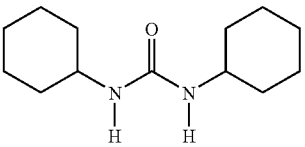 [SMILES: O=C(NC1CCCCC1)NC1CCCCC1] |  | 0.09 ± 0.01 | 0.16 ± 0.01 |
| 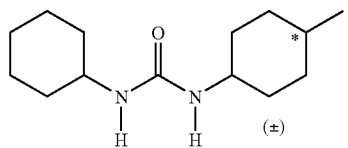 [SMILES: CC1CCC(NC(=O)NC2CCCCC2)CC1] | 538 | 0.05 ± 0.01 | 0.10 ± 0.01 |
| 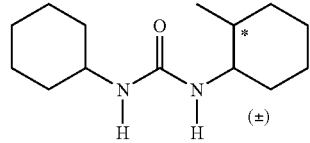 [SMILES: CC1CCCCC1NC(=O)NC1CCCCC1] | 551 | 0.05 ± 0.01 | 0.10 ± 0.01 |
| 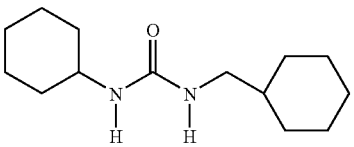 [SMILES: O=C(NCC1CCCCC1)NC1CCCCC1] | 57 | 0.06 ± 0.01 | 0.16 ± 0.01 |
| 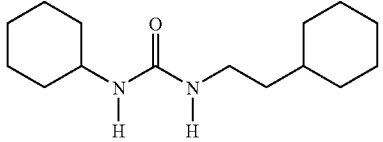 [SMILES: O=C(NCCC1CCCCC1)NC1CCCCC1] | 360 | 0.05 ± 0.01 | 0.10 ± 0.01 |
| 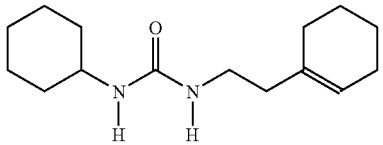 [SMILES: O=C(NCCC1=CCCCC1)NC1CCCCC1] | 359 | 0.05 ± 0.01 | 0.10 ± 0.01 |
| 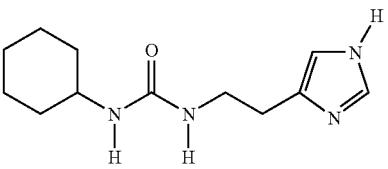 [SMILES: O=C(NCCc1c[nH]cn1)NC1CCCCC1] | 461 | 0.42 ± 0.01 | 0.55 ± 0.02 |

TABLE 1-continued
Inhibition of MsEH (0.13 μM) and HsEH (0.2 μM)
| Structure inhibitors | nb | Mouse sEH IC$_{50}$ (μM)* | Human sEH IC$_{50}$ (μM)* |
|---|---|---|---|
| 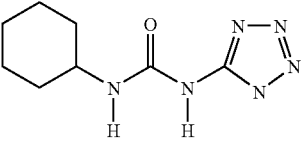 [SMILES: O=C(Nc1nnn[nH]1)NC1CCCCC1] | 533 | 0.05 ± 0.1 | 0.10 ± 0.01 |
| 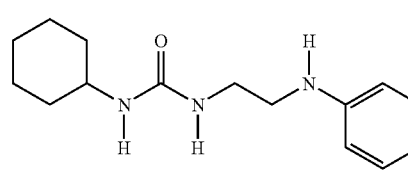 | 463 | 0.90 ± 0.07 | 8.3 ± 0.4 |
| 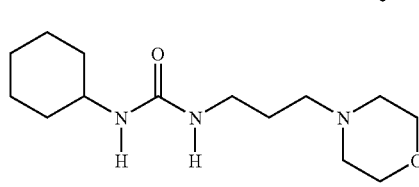 | 377 | 0.7 ± 0.1 | 17.8 ± 0.7 |
| 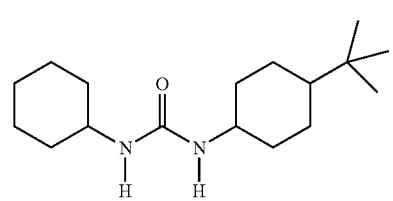 [SMILES: CC(C)(C)C1CCC(NC(=O)NC2CCCCC2)CC1] | 428 | 0.05 ± 0.1 | 0.10 ± 0.01 |
| 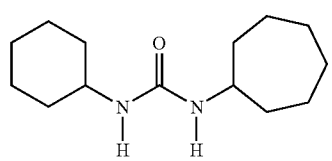 [SMILES: O=C(NC1CCCCCC1)NC1CCCCC1] | 22 | 0.05 ± 0.1 | 0.10 ± 0.01 |
| 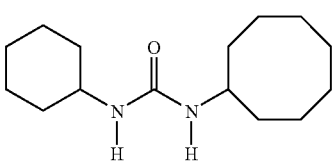 [SMILES: O=C(NC1CCCCCCC1)NC1CCCCC1] | 58 | 0.05 ± 0.01 | 0.09 ± 0.01 |
| 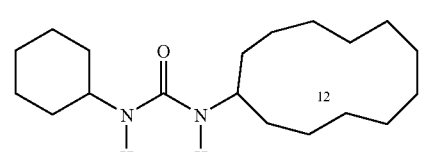 | 119 | 0.05 ± 0.01 | 0.10 ± 0.01 |
| 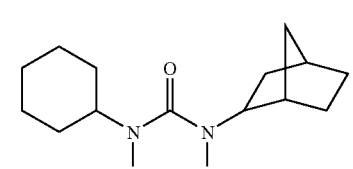 | 543 | 0.05 ± 0.01 | 0.10 ± 0.01 |
| 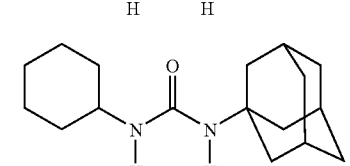 | 192 | 0.05 ± 0.01 | 0.10 ± 0.01 |

TABLE 1-continued

Inhibition of MsEH (0.13 μM) and HsEH (0.2 μM)

| Structure inhibitors | nb | Mouse sEH IC$_{50}$ (μM)* | Human sEH IC$_{50}$ (μM)* |
|---|---|---|---|
| cyclohexyl-NH-C(O)-NH-adamantyl | 427 | 0.05 ± 0.01 | 0.10 ± 0.01 |
| cyclohexyl-NH-C(O)-NH-CH(CH$_3$)-adamantyl | 358 | 0.05 ± 0.01 | 0.18 ± 0.04 |
| cyclohexyl-NH-C(O)-NH-phenyl | 21 | 0.76 ± 0.02 | 1.39 ± 0.02 |
| cyclohexyl-NH-C(O)-NH-(2,6-dimethylphenyl) | 435 | 0.05 ± 0.01 | 0.18 ± 0.01 |
| cyclohexyl-NH-C(O)-NH-CH$_2$-phenyl | 270 | 0.05 ± 0.01 | 1.9 ± 0.1 |
| cyclohexyl-NH-C(O)-NH-CH(CH$_3$)-phenyl (S-) | 544 | 0.05 ± 0.01 | 0.10 ± 0.01 |
| cyclohexyl-NH-C(O)-NH-CH(CH$_3$)-phenyl (R+) | 545 | 0.05 ± 0.01 | 3.7 ± 0.3 |
| cyclohexyl-CH$_2$-NH-C(O)-NH-adamantyl | 437 | 0.05 ± 0.01 | 0.10 ± 0.01 |

TABLE 1-continued
Inhibition of MsEH (0.13 μM) and HsEH (0.2 μM)
| Structure inhibitors | nb | Mouse sEH IC$_{50}$ (μM)* | Human sEH IC$_{50}$ (μM)* |
|---|---|---|---|
| 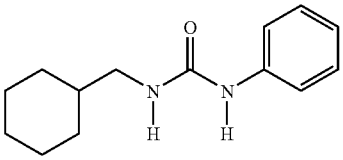 [SMILES: O=C(NCC1CCCCC1)Nc1ccccc1] | 176 | 0.06 ± 0.01 | 0.53 ± 0.03 |
| 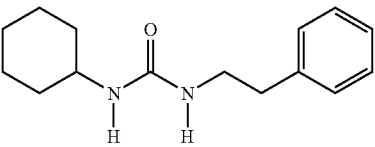 [SMILES: O=C(NCCc1ccccc1)NC1CCCCC1] | 36 | 0.06 ± 0.01 | 0.16 ± 0.02 |
| 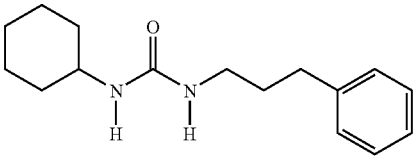 [SMILES: O=C(NCCCc1ccccc1)NC1CCCCC1] | 104 | 0.04 ± 0.01 | 0.29 ± 0.01 |
| 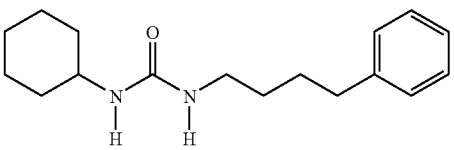 [SMILES: O=C(NCCCCc1ccccc1)NC1CCCCC1] | 105 | 0.05 ± 0.01 | 0.58 ± 0.03 |
| 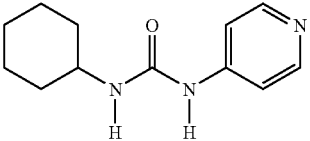 [SMILES: O=C(Nc1ccncc1)NC1CCCCC1] | 100 | 0.07 ± 0.01 | 0.15 ± 0.01 |
| 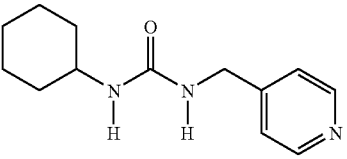 [SMILES: O=C(NCc1ccncc1)NC1CCCCC1] | 188 | 0.73 ± 0.08 | 2.50 ± 0.03 |
| 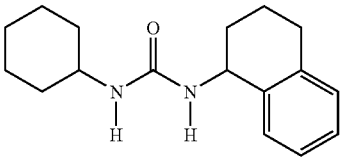 [SMILES: O=C(NC1CCCCC1)NC1CCCc2ccccc21] | 434 | 0.05 ± 0.01 | 0.10 ± 0.01 |
| 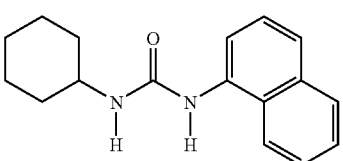 | 59 | 0.85 ± 0.02 | 0.48 ± 0.01 |
| 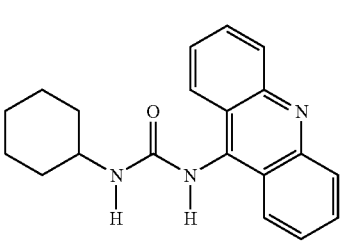 [SMILES: O=C(Nc1c2ccccc2nc2ccccc12)NC1CCCCC1] | 559 | 0.08 ± 0.01 | 0.14 ± 0.01 |

TABLE 1-continued
Inhibition of MsEH (0.13 μM) and HsEH (0.2 μM)
| Structure inhibitors | nb | Mouse sEH IC$_{50}$ (μM)* | Human sEH IC$_{50}$ (μM)* |
|---|---|---|---|
| 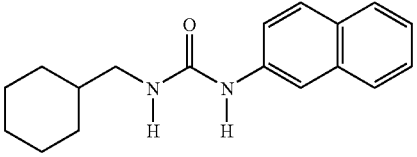 [SMILES: O=C(NCC1CCCCC1)Nc1ccc2ccccc2c1] | 169 | 0.06 ± 0.01 | 0.13 ± 0.01 |
| 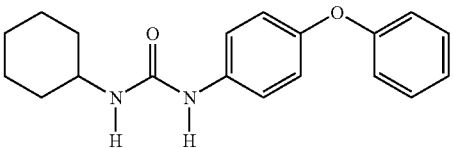 [SMILES: O=C(Nc1ccc(Oc2ccccc2)cc1)NC1CCCCC1] | 140 | 0.05 ± 0.01 | 0.10 ± 0.01 |
| 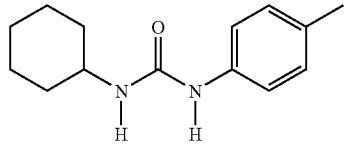 [SMILES: Cc1ccc(NC(=O)NC2CCCCC2)cc1] | 108 | 0.13 ± 0.01 | 0.17 ± 0.01 |
| 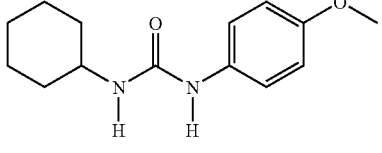 | 67 | 0.71 ± 0.04 | 0.23 ± 0.01 |
| 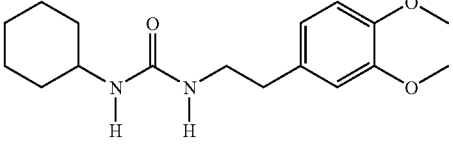 | 384 | 0.05 ± 0.01 | 1.0 ± 0.2 |
| 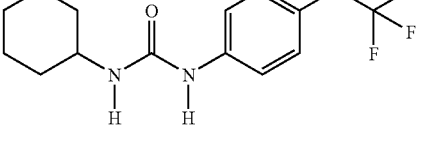 | 343 | 0.05 ± 0.01 | 0.10 ± 0.01 |
| 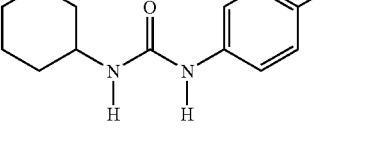 | 118 | 0.06 ± 0.01 | 0.10 ± 0.01 |
| 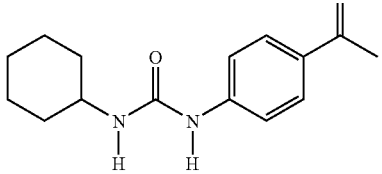 | 126 | 0.06 ± 0.01 | 0.27 ± 0.02 |

TABLE 1-continued
Inhibition of MsEH (0.13 μM) and HsEH (0.2 μM)
| Structure inhibitors | nb | Mouse sEH IC$_{50}$ (μM)* | Human sEH IC$_{50}$ (μM)* |
|---|---|---|---|
| 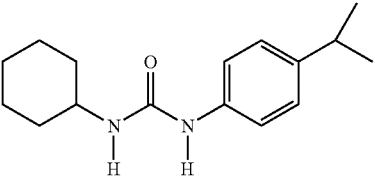 [SMILES: CC(C)c1ccc(NC(=O)NC2CCCCC2)cc1] | 66 | 0.09 ± 0.01 | 0.07 ± 0.01 |
| 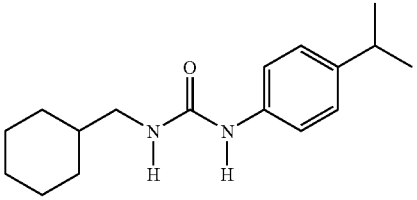 [SMILES: CC(C)c1ccc(NC(=O)NCC2CCCCC2)cc1] | 180 | 0.06 ± 0.01 | 0.10 ± 0.01 |
| 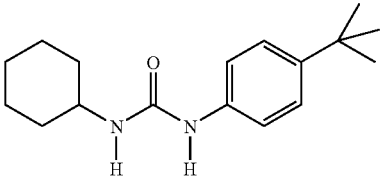 [SMILES: CC(C)(C)c1ccc(NC(=O)NC2CCCCC2)cc1] | 75 | 0.06 ± 0.01 | 0.23 ± 0.01 |
| 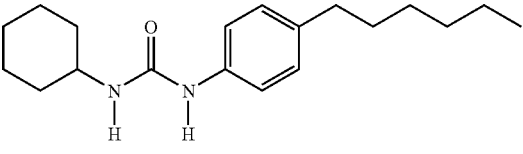 [SMILES: CCCCCCc1ccc(NC(=O)NC2CCCCC2)cc1] | 501 | 0.05 ± 0.01 | 0.16 ± 0.01 |
| 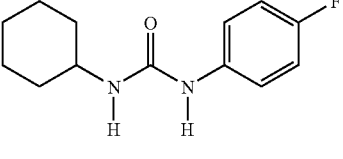 | 60 | 0.78 ± 0.02 | 0.43 ± 0.02 |
| 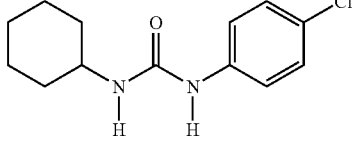 | 20 | 0.19 ± 0.02 | 0.40 ± 0.05 |
| 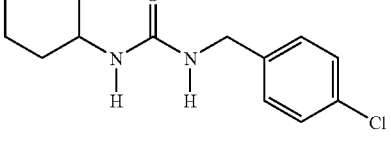 | 193 | 0.05 ± 0.01 | 0.19 ± 0.01 |
| 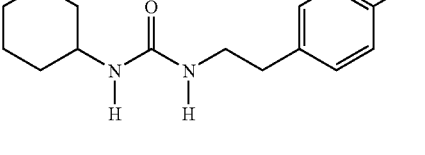 | 361 | 0.07 ± 0.02 | 0.20 ± 0.02 |

TABLE 1-continued
Inhibition of MsEH (0.13 µM) and HsEH (0.2 µM)
| Structure inhibitors | nb | Mouse sEH IC$_{50}$ (µM)* | Human sEH IC$_{50}$ (µM)* |
|---|---|---|---|
| 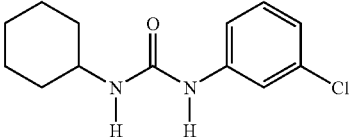 [SMILES: O=C(Nc1cccc(Cl)c1)NC1CCCCC1] | 44 | 0.07 ± 0.01 | 0.19 ± 0.01 |
| 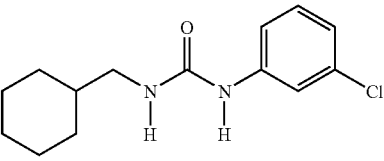 [SMILES: O=C(NCC1CCCCC1)Nc1cccc(Cl)c1] | 179 | 0.06 ± 0.01 | 0.10 ± 0.01 |
| 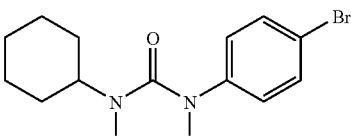 | 65 | 0.17 ± 0.01 | 0.11 ± 0.01 |
| 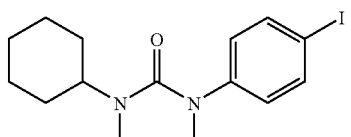 | 53 | 0.07 ± 0.01 | 0.12 ± 0.01 |
| 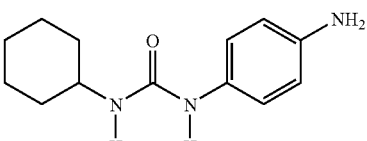 | 385 | 0.17 ± 0.02 | 2.2 ± 0.1 |
| 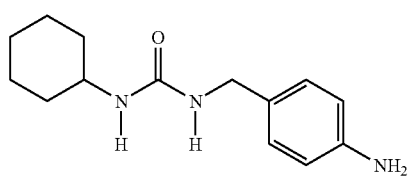 | 379 | 0.05 ± 0.01 | 1.5 ± 0.1 |
| 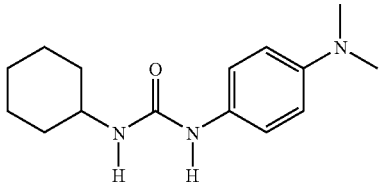 [SMILES: CN(C)c1ccc(NC(=O)NC2CCCCC2)cc1] | 362 | 0.05 ± 0.01 | 1.5 ± 0.1 |
| 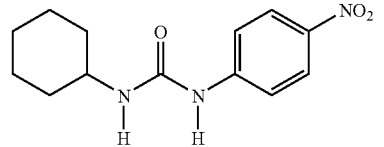 [SMILES: O=C(Nc1ccc([N+](=O)[O-])cc1)NC1CCCCC1] | 38 | 0.17 ± 0.01 | 0.36 ± 0.02 |
| 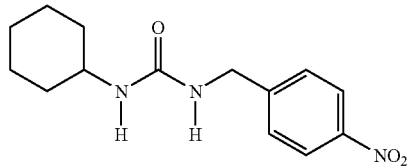 [SMILES: O=C(NCc1ccc([N+](=O)[O-])cc1)NC1CCCCC1] | 341 | 2.3 ± 0.3 | 4.3 ± 0.4 |

TABLE 1-continued

Inhibition of MsEH (0.13 μM) and HsEH (0.2 μM)

| Structure inhibitors | nb | Mouse sEH IC$_{50}$ (μM)* | Human sEH IC$_{50}$ (μM)* |
|---|---|---|---|
| cyclohexyl-NH-C(O)-NH-C$_6$H$_4$-OH | 128 | 0.79 ± 0.08 | 11.1 ± 0.8 |
| 1-adamantyl-NH-C(O)-NH-1-adamantyl | 411 | 0.05 ± 0.01 | 0.10 ± 0.01 |
| 2-adamantyl-NH-C(O)-NH-2-adamantyl | 412 | 0.05 ± 0.01 | 0.10 ± 0.01 |
| 1-adamantyl-NH-C(O)-NH-cyclooctyl | 413 | 0.05 ± 0.01 | 0.10 ± 0.01 |
| 1-adamantyl-NH-C(O)-NH-(CH$_2$)$_3$-Ph | 438 | 0.05 ± 0.01 | 0.10 ± 0.01 |
| Ph-NH-C(O)-NH-(CH$_2$)$_3$-Ph | 430 | 0.21 ± 0.02 | 0.55 ± 0.03 |
| PhCH$_2$-NH-C(O)-NH-(CH$_2$)$_2$-Ph | 470 | 0.59 ± 0.08 | 7.6 ± 0.1 |
| PhCH$_2$-NH-C(O)-NH-(CH$_2$)$_2$-cyclohexenyl | 471 | 0.25 ± 0.03 | 2.2 ± 0.1 |

TABLE 1-continued

Inhibition of MsEH (0.13 μM) and HsEH (0.2 μM)

| Structure inhibitors | nb | Mouse sEH IC$_{50}$ (μM)* | Human sEH IC$_{50}$ (μM)* |
| --- | --- | --- | --- |
| (4-isopropylphenyl)-urea-CH$_2$-CH(OEt)$_2$ | 159 | 0.59 ± 0.03 | 3.40 ± 0.04 |
| (4-isopropylphenyl)-urea-CH$_2$CH$_2$-phenyl | 156 | 0.20 ± 0.01 | 0.48 ± 0.01 |
| (4-isopropylphenyl)-urea-n-hexyl | 287 | 0.09 ± 0.01 | 0.10 ± 0.01 |
| (3-chlorophenyl)-urea-(CH$_2$)$_3$-CH(OEt)$_2$ | 167 | 0.39 ± 0.02 | 3.77 ± 0.03 |
| (4-chlorophenyl)-urea-(3,4-dichlorophenyl) | | 0.36 ± 0.02 | 0.12 ± 0.01 |
| (3,4-dichlorophenyl)-urea-(3,4-dichlorophenyl) | 299 | 0.7 ± 0.1 | 0.26 ± 0.02 |
| (1-naphthyl)-urea-n-propyl | 253 | 0.10 ± 0.02 | 0.28 ± 0.01 |
| (2-naphthyl)-urea-(CH$_2$)$_{10}$-COOH | 283 | 0.7 ± 0.2 | 1.12 ± 0.03 |

TABLE 1-continued

Inhibition of MsEH (0.13 μM) and HsEH (0.2 μM)

| Structure inhibitors | nb | Mouse sEH IC$_{50}$ (μM)* | Human sEH IC$_{50}$ (μM)* |
|---|---|---|---|
| (cyclohexyl-NH-C(O)-NH-C(O)-C$_6$H$_4$-Cl) | 257 | 0.05 ± 0.01 | 0.10 ± 0.04 |

A second preferred class of compounds for practice in accordance with the invention has the structure shown by Formula 2,

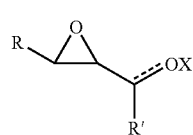

FORMULA 2 wherein R is alkyl or aryl, the compound is trans-across the epoxide ring, OX is a carbonyl (═O) or hydroxy group (OH) and R' is a H, alkyl or aryl group. The preparation of these compounds is described in U.S. Pat. No. 5,955,496 and in WO98/06261.

Exemplary compounds are shown in Table 2, below.

TABLE 2

Inhibition of MsEH (0.13 μM) and HsEH (0.26 μM)

| R | R' | X—Y | Abs. Conf. | Mouse sEH IC$_{50}$ (μM)* | Human sEH IC$_{50}$ (μM)* |
|---|---|---|---|---|---|
| C$_6$H$_5$ | C$_6$H$_5$ | C═O | ± | 2.9 ± 0.3 | 0.3 ± 0.1 |
| C$_6$H$_5$ | C$_6$H$_5$ | CH—OH | ± | 12.6 ± 0.9 | 22 ± 2 |
| C$_6$H$_5$ | C$_6$H$_5$ | C═NOH | ± | 3.5 ± 0.5 | 0.29 ± 0.01 |
| C$_6$H$_5$ | C$_6$H$_5$ | S═O | ± | 2.3 ± 0.4 | 0.31 ± 0.02 |
| C$_6$H$_5$ | C$_6$H$_5$ | CH—OCH$_3$ | ± | 103 ± 5 | 34 ± 1 |
| 4-F-C$_6$H$_4$ | C$_6$H$_5$ | C═O | ± | 1.3 ± 0.3 | 0.3 ± 0.1 |
| 4-F-C$_6$H$_4$ | C$_6$H$_5$ | CH—OH | ± | 72 ± 16 | 18 ± 2 |
| 4-C$_6$F$_5$—C$_6$H$_4$ | C$_6$H$_5$ | C═O | ± | 0.14 ± 0.01 | 0.20 ± 0.01 |
| 4-C$_6$H$_5$—C$_6$H$_4$ | C$_6$H$_5$ | CH—OH | ± | 0.51 ± 0.04 | 0.72 ± 0.03 |
| 4-C$_6$H$_5$—C$_6$H$_4$ | C$_6$H$_5$ | C═NOH | ± | 42 ± 3 | 35 ± 1 |
| 4-C$_6$H$_5$—C$_6$H$_4$ | C$_6$H$_5$ | S═O | ± | 73 ± 5 | 70 ± 3 |
| 4-C$_6$H$_5$—C$_6$H$_4$ | C$_6$H$_5$ | CH—OCH$_3$ | ± | 0.48 ± 0.05 | 1.36 ± 0.07 |
| C$_{10}$H$_7$ | C$_6$H$_5$ | C═O | ± | 0.49 ± 0.02 | 0.85 ± 0.06 |
| 4-C$_6$H$_5$—C$_6$H$_4$ | 4-CH$_3$—C$_6$H$_4$ | C═O | ± | 0.10 ± 0.01 | 0.19 ± 0.03 |
| 4-C$_6$H$_5$—C$_6$H$_4$ | 4-CH$_3$—C$_6$H$_4$ | CH—OH | ± | 0.09 ± 0.01 | 0.15 ± 0.02 |
| 4-NO$_2$—C$_6$H$_4$ | CH$_3$ | C═O | ± | 163 ± 11 | 269 ± 5 |
| 4-NO$_2$—C$_6$H$_4$ | CH$_3$ | CH—OH | ± | 6.5 ± 0.2 | 39 ± 1 |
| C$_6$H$_5$ | H | CH—OH | R,R | 1100 ± 23 | |
| C$_6$H$_5$ | H | CH—OH | S,S | 2400 ± 46 | |
| 4-NO$_2$—C$_6$H$_4$ | H | CH—OH | ± | 5 ± 1 | |
| 4-NO$_2$—C$_6$H$_4$ | H | CH—OH | R,R | 1200 ± 25 | |
| 4-NO$_2$—C$_6$H$_4$ | H | CH—OH | S,S | 1.6 ± 0.6 | |

Abs. Conf.: Absolute configuration

The enzymes of interest for this invention typically are able to distinguish enantiomers. Thus, in choosing an inhibitor for use for an application in accordance with the invention it is preferred to screen different optical isomers of the inhibitor with the selected enzyme by routine assays so as to choose a better optical isomer, if appropriate, for the particular application. The pharmacophores described here can be used to deliver a reactive functionality to the catalytic site. These could include alkylating agents such as halogens or epoxides or Michael acceptors which will react with thiols and amines. These reactive functionalities also can be used to deliver fluorescent or affinity labels to the enzyme active site for enzyme detection.

DETAILED DESCRIPTION OF THE PREFERRED EMBODIMENTS

Figure 1:
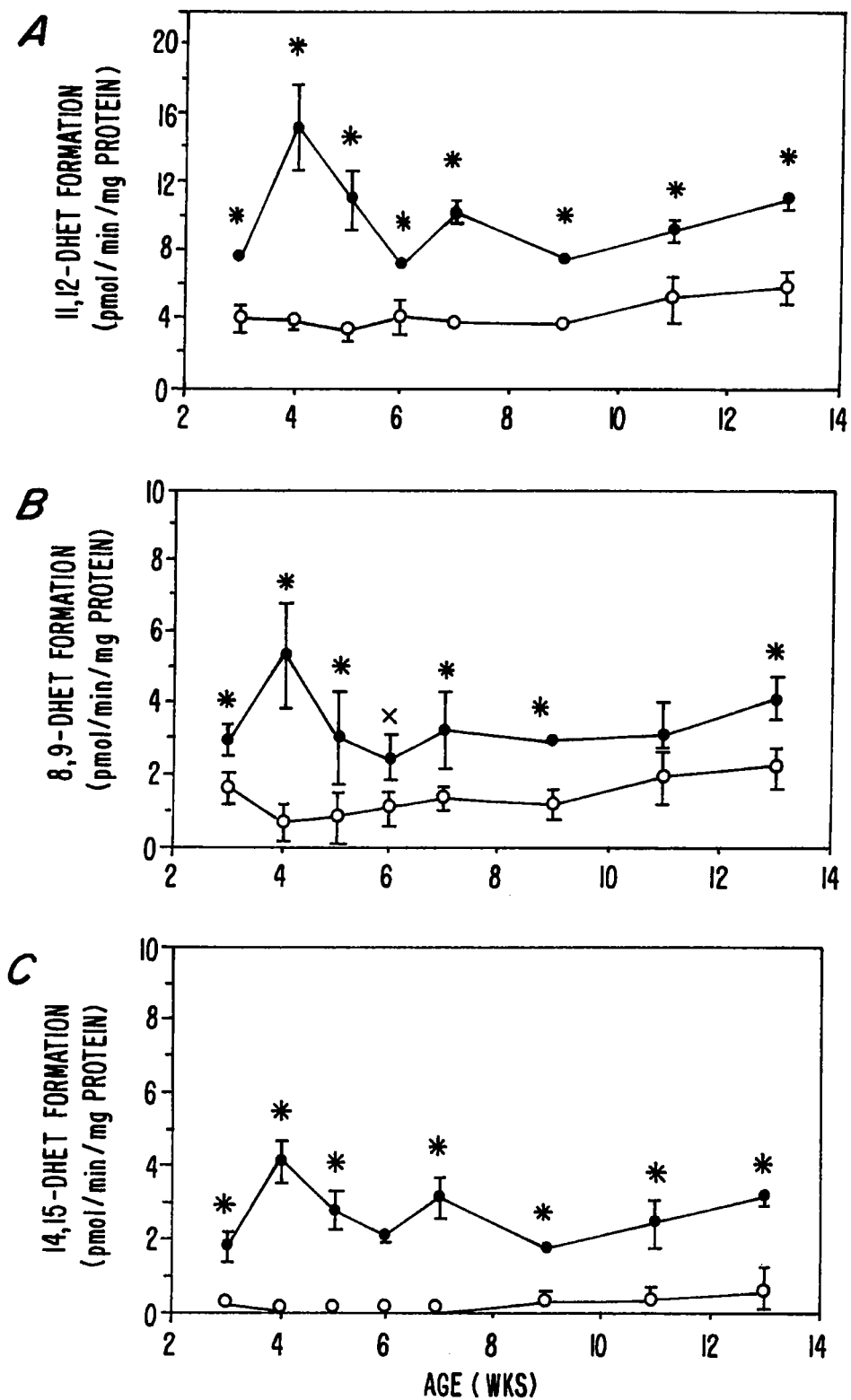
FIGS. 1 and 2 show that renal microsomal DHET formation is increased in the SHR relative to the WKY and this is due to increased renal EET hydrolysis. The NADPH-dependent formation of 11,12-DHET (FIG. 1A), 8,9-DHET (FIG. 1B) and 14,15-DHET (FIG. 1C) was measured in incubations of WKY (o) and SHR (●) renal microsomes with [$^{14}$C]-arachidonic acid (FIG. 1) or [$^{14}$C]-regioisomeric EETs (FIG. 2). Values are the mean ±SE from three to six animals of a given age and strain (FIG. 1) or means of two separate animals (FIG. 2). Significant differences between WKY and SHR samples at a given age are indicated (p<0.05). The hydrolysis of all of the major EETs was increased in the SHR kidney.

The present invention is based on the discovery that epoxide hydrolase activity is associated with hypertension. The epoxyeicosatrienoic acids (EETs) are regarded as antihypertensive eicosanoids due to their potent effects on renal vascular tone and sodium and water transport in the renal tubule. As shown here, EET activity is regulated by hydrolysis to the corresponding dihydroxyeicosatrienoic acids by epoxide hydrolase. Inhibition of EET hydrolysis in vivo with a potent and selective soluble epoxide hydrolase inhibitor leads to a decrease in blood pressure. Thus, the present invention provides a new therapeutic approach for the control of blood pressure.

Abbreviations and Definitions:

The abbreviations used herein have their conventional meaning within the chemical and biological arts.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NH—C(NH$_2$)=NH, —NR"C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R"' each independently refer to hydrogen, unsubstituted (C$_1$-C$_8$)alkyl and heteroalkyl, unsubstituted aryl, aryl substituted with 1-3 halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R"' are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include trifluoromethyl, 2,2,2-trifluoroethyl, 4-chlorobutyl, 3-bromopropyl, and the like.

As used herein, the term "heteroatom" is meant to include oxygen (O), nitrogen (N), Boron (B), phosphorous (P) and sulfur (S).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

Inhibitors of Epoxide Hydrolases

As noted above, a preferred class of inhibitors of the invention are compounds shown by Formulas 1 and 2, above. Means for preparing such compounds and assaying desired compounds for the ability to inhibit epoxide hydrolases is described in the parent application, U.S. Ser. No. 09/252,148. Compounds of Formula 2 are described in U.S. Pat. No. 5,955,496 and in WO98/06261.

In addition to the compounds in Formula 1 which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 can direct the inhibitor to the enzyme where a reactive functionality in the enzyme catalytic site can form a covalent bond with the inhibitor. One group of molecules which could interact like this would have a leaving group such as a halogen or tosylate which could be attacked in an $S_N2$ manner with a lysine or histidine. Alternatively, the reactive functionality could be an epoxide or Michael acceptor such as a α/β-unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., *The Pharmacological Basis of Therapeutics*, 7$^{th}$ Edition, MacMillan Publishing Company, New York, p. 16 (1985)) Esters, for example, are common prodrugs which are released to give the corresponding alcohols and acids enzymatically (Yoshigae et al., *Chirality*, 9:661-666 (1997)). The prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., *Journal of Agricultural and Food Chemistry*, 21(5):747-751 (1973); Fahmy et al, *Journal of Agricultural and Food Chemistry*, 26(3):550-556 (1978); Jojima et al., *Journal of Agricultural and Food Chemistry*, 31(3):613-620 (1983); and Fahmy et al., *Journal of Agricultural and Food Chemistry*, 29(3):567-572 (1981).)

Such active proinhibitor derivatives are within the scope of the present invention, and the just-cited references are incorporated herein by reference. Without being bound by theory, it is believed that suitable inhibitors of the invention mimic the enzyme transition state so that there is a stable interaction with the enzyme catalytic site. The inhibitors appear to form hydrogen bonds with the nucleophilic carboxylic acid and a polarizing tyrosine of the catalytic site.

Where the modified activity of the complexed epoxide hydrolase is enzyme inhibition, then particularly preferred compound embodiments have an $IC_{50}$ (inhibition potency or, by definition, the concentration of inhibitor which reduces enzyme activity by 50%) of less than about 500 μM.

Although the preferred inhibitors of the invention specifically inhibit the activity of sEH, some inhibitors of the invention can be used to inhibit the activity of microsomal epoxide hydrolase (mEH). The micosomal enzyme play a significant role in the metabolism of xenobiotics such as polyaromatic toxicants. Additionally, polymorphism studies have underlined a potential role of this enzyme in relation to several diseases, such as emphysema, spontaneous abortion and several forms of cancer. Inhibition of recombinant rat and human mEH can be obtained using primary ureas, amides, and amines. For example, elaidamide, has a $K_i$ of 70 nM for recombinant rat mEH. This compound interacts with the enzyme forming a non-covalent complex, and blocks substrate turnover through an apparent mix of competitive and non-competitive inhibition kinetics. Furthermore, in insect cell culture expressing rat mEH, elaidamide enhances the toxicity effects of epoxide-containing xenobiotics.

Assays for Epoxide Hydrolase Activity

The invention also provide methods for assaying for epoxide hydrolase activity as diagnostic assay to identify individuals at increased risk for hypertension and/or those that would benefit from the therapeutic methods of the invention. Any of a number of standard assays for determining epoxide hydrolase activity can be used. For example, suitable assays are described in Gill, et al., *Anal Biochem* 131, 273-282 (1983); and Borhan, et al., *Analytical Biochemistry* 231, 188-200 (1995)). Suitable in vitro assays are described in Zeldin et al. *J Biol. Chem.* 268:6402-6407 (1993). Suitable in vivo assays are described in Zeldin et al. *Arch Biochem Biophys* 330:87-96 (1996). Assays for epoxide hydrolase using both putative natural substrates and surrogate substrates have been reviewed (see, Hammock, et al. *In: Methods in Enzymology, Volume III, Steroids and Isoprenoids, Part B*, (Law, J. H. and H. C. Rilling, eds. 1985), Academic Press, Orlando, Fla., pp. 303-311 and Wixtrom et al., *In: Biochemical Pharmacology and Toxicology, Vol.* 1*: Methodological Aspects of Drug Metabolizing Enzymes*, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, and Hammock. *Anal. Biochem.* 174:291-299 (1985) and Dietze, et al. *Anal. Biochem.* 216:176-187 (1994)).

The enzyme also can be detected based on the binding of specific ligands to the catalytic site which either immobilize the enzyme or label it with a probe such as luciferase, green fluorescent protein or other reagent. For the data in this disclosure the enzyme was assayed by its hydration of EETs, its hydrolysis of an epoxide to give a colored product as described by Dietze et al. (1994) or its hydrolysis of a radioactive surrogate substrate (Borhan et al., 1995)

The assays of the invention are carried out using an appropriate sample from the patient. Typically, such a sample is a blood sample.

Other Means of Inhibiting EH Activity

Other means of inhibiting EH activity or gene expression can also be used. For example, a nucleic acid molecule complementary to at least a portion of the human EH gene can be used to inhibit EH gene expression. Means for inhibiting gene expression using, for example, antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the EH gene is retained as a functional property of the polynucleotide. As one embodiment of the antisense molecules form a triple helix-containing, or "triplex" nucleic acid. Triple helix formation results in inhibition of gene expression by, for example, preventing transcription of the target gene (see, e.g., Cheng et al., 1988, *J Biol. Chem.* 263:151 10; Ferrin and Camerini-Otero, 1991, *Science* 354:1494; Ramdas et al., 1989, *J. Biol. Chem.* 264: 17395; Strobel et al., 1991, *Science* 254:1639; and Rigas et al., 1986, *Proc. Natl. Acad. Sci. U.S.A.* 83:9591)

In another embodiment, ribozymes can be used (see, e.g., Cech, 1995, *Biotechnology* 13:323; and Edgington, 1992, *Biotechnology* 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA can be made by inserting (ligating) an EH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

It will be appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired $T_m$). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, *Science* 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, 1996, *Current Opinion in Neurobiology* 6:629-634. Another subsequence, the h (hydrophobic) domain of signal peptides, was found to have similar cell membrane translocation characteristics (see, e.g., Lin et al., 1995, *J. Biol. Chem.* 270:14255-14258). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

Epoxide Hydrolase Inhibition to Treat Inflammatory Disease

The inflammatory response is one of the most important physiological mechanisms for the maintenance of human health. However, disorders of inflammation or an inappropriate inflammatory response can result in tissue injury, morbidity, or mortality.

Adult respiratory distress syndrome (ARDS) is a pulmonary disease that has a mortality rate of 50% and results from lung lesions that are caused by a variety of conditions found in trauma patients and in severe burn victims. Ingram, R. H. Jr., "Adult Respiratory Distress Syndrome," *Harrison's Principals of Internal Medicine*, 13, p. 1240, 1995. With the possible exception of glucocorticoids, there have not been therapeutic agents known to be effective in preventing or ameliorating the tissue injury, such as microvascular damage, associated with acute inflammation that occurs during the early development of ARDS.

ARDS, which is defined in part by the development of alveolar edema, represents a clinical manifestation of pulmonary disease resulting from both direct and indirect lung injury. While previous studies have detailed a seemingly unrelated variety of causative agents, the initial events underlying the pathophysiology of ARDS are not well understood. ARDS was originally viewed as a single organ failure, but is now considered a component of the multisystem organ failure syndrome (MOFS). Pharmacologic intervention or prevention of the inflammatory response is presently viewed as a more promising method of controlling the disease process than improved ventilatory support techniques. See, for example, Demling, *Annu. Rev. Med.*, 46, pp. 193-203, 1995.

Another disease (or group of diseases) involving acute inflammation is the systematic inflammatory response syndrome, or SIRS, which is the designation recently established by a group of researchers to describe related conditions resulting from, for example, sepsis, pancreatitis, multiple trauma such as injury to the brain, and tissue injury, such as laceration of the musculature, brain surgery, hemorrhagic shock, and immune-mediated organ injuries. Bone, *JAMA*, 268(24):3452-3455 (1992).

We view an important therapeutic application for an aspect of this invention to be in treating diseases of the lung. The lung, with its extensive surface area exposed directly to the environment, is particularly susceptible to oxidant injury and products of inflammation. Since the entire cardiac output passes through the pulmonary artery, the lungs can also be injured by blood-borne agents. The cellular heterogeneity of mammalian lung complicates direct study of these pulmonary cells most susceptible to injury. Furthermore, the complex pulmonary anatomy renders it difficult to distinguish precisely where biological agents are metabolized in lung tissues. The target tissue and sequence of events underlying alveolar edema are not conclusively established; consequently, the interrelationships and relative contributions of endothelial versus epithelial versus inflammatory compartments in mitigating damage to the air-blood barrier remain equivocal.

The ARDS ailments are seen in a variety of patients with severe burns or sepsis. Sepsis in turn is one of the SIRS symptoms. In ARDS there is an acute inflammatory reaction with high numbers of neutrophils that migrate into the interstitium and alveoli. If this progresses there is increased inflammation, edema, cell proliferation, and the end result is impaired ability to extract oxygen. ARDS is thus a common complication in a wide variety of diseases and trauma. The only treatment is supportive. There are an estimated 150,000 cases per year and mortality ranges from 10% to 90%.

The exact cause of ARDS is not known. However it has been hypothesized that over-activation of neutrophils leads to the release of linoleic acid in high levels via phospholipase $A_2$ activity. Linoleic acid in turn is converted to 9,10-epoxy-12-octadecenoate enzymatically by neutrophil cytochrome P-450 epoxygenase and/or a burst of active oxygen. This lipid epoxide, or leukotoxin, is found in high levels in burned skin and in the serum and bronchial lavage of burn patients. Furthermore, when injected into rats, mice, dogs, and other mammals it causes ARDS. The mechanism of action is not known. However, the leukotoxin diol produced by the action of the soluble epoxide hydrolase appears to be a specific inducer of the mitochondrial inner membrane permeability transition (MPT). This induction by leukotoxin diol, the diagnostic release of cytochrome c, nuclear condensation, DNA laddering, and CPP32 activation leading to cell death were all inhibited by cyclosporin A which is diagnostic for MPT induced cell death. Actions at the mitochondrial and cell level were consistent with this mechanism of action suggesting that the inhibitors of this invention could be used therapeutically with compounds which block MPT.

Therapeutic or pharmaceutical compositions of the invention that contain the inhibitors may be prepared by any of the various methods well known. Typically, the inhibitor is formulated so as to be suitable for oral or parenteral administration and is typically dissolved or dispersed in a physiologically tolerable carrier or diluent. As one example, an inhibitor can be dissolved or dispersed in a liquid composition such as sterile suspension or solution or as an isotonic preparation. Particularly well suited are injectable medium formulated with buffered or unbuffered isotonic and sterile saline or glucose solution. For in vitro use was in which inhibition of the activity of the target epoxide hydrolase may be monitored by the lessening of the degree of inflammation are well known. The amount of therapeutic inhibitor administered can be by a single administration or a submultiple of the total amount. In addition, multiple administrations over a period of several days, weeks, or months are contemplated.

The active agent can also be used in compositions such as tablets or pills, preferably containing a unit dose, and may be mixed with conventional tableting ingredients. Actual dosage levels of the epoxide hydrolase inhibitor can be varied to obtain the desired therapeutic response for a particular composition and method of administration. The total daily dose administered is contemplated to be from about 0.001 to about 100 mg per kg body weight. However, when practicing the invention a drug like clofibrate, which is known to induce the soluble epoxide hydrolase and cytochrome P-450, and a drug like acetaminophen, which depletes glutathione, should be avoided. This is because we have experimental data suggesting that when glutathione levels are depleted, then leukotoxin becomes more toxic. By contrast, parallel therapies designed to enhance alternate pathways of leukotoxin metabolism such as administration of N-acetylcysteine and glutathione and their ethyl esters should be encouraged.

Therapeutic Administration

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of the invention or a pharmaceutically acceptable salt of the compound.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

A therapeutically effective amount of the compounds of the invention is employed in treatment. The dosage of the specific compound for treatment depends on many factors that are well known to those skilled in the art. They include for example, the route of administration and the potency of the particular compound. An exemplary dose is from about 0.001 µM/kg to about 100 mg/kg body weight of the mammal. Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

Male Swiss Webster mice (25-28 g) were purchased from Simonsen, Gilroy, Calif. The animals had free access to water and food. The mice (three in each group) were pretreated i.p. with dicyclohexylurea (compound 2) suspended in corn oil (400 mg/kg, 7 ml/kg) or corn oil as positive controls. After 30 minutes of the pretreatment, the mice were treated intravenously through the tail vein with a 1:1 mixture of leukotoxin/isoleukotoxin methyl esters in ethanol (700 mg/kg, 1.0 ml/kg).

The mice died of respiratory distress after exposure to leukotoxin/isoleukotoxin. The lethal reactions took place sequentially with accelerated breathing, opening of the mouth to assist breathing, and bloody fluid running from the nose. However, pretreatment with N,N'-dicyclohexylurea 2 either blocked the animal death induced by leukotoxin/isoleukotoxin or lengthened the lives of the mice.

EXAMPLE 2

Synthesis of 1-Octyl-3-pentylurea

To 0.262 g (3.00 mmol) of pentylamine in 20 mL of hexane is added 0.53 mL (0.47 g, 3.0 mmol) of octylisocyanate with stirring to eventually produce a white crystalline solid. After standing overnight the mixture is cooled, the solid product collected, and washed with cold hexane. On air drying there is obtained 0.705 g (2.91 mmol, 97%) of 1-octyl-3-pentylurea as very fine white needles, mp 65.0-65.5° C. The material displays a $^{13}$C-NMR and a mass spectrum consistent with the assigned structure. $^{13}$C-NMR (CDCl$_3$): δ 159.0 (C=O), 40.47 and 40.45 (C-1 and C-1'), 31.8 (C-6 and C-3'), 30.4 (C-2), 30.1 (C-2'), 29.3 (C-4), 29.2 (C-5), 27.0 (C-3), 22.5 (C-7), 22.4 (C-4'), 13.9 (C-8 and C-5'); important infrared absorption bands (KBr disc) are present at 3334 (s, N—H), 1617 (vs, C=O), and 1579 (vs, amide II) cm$^{-1}$.

EXAMPLE 3

Synthesis of 1-Cyclohexyl-3-cyclooctylurea

Cyclooctylamine, 0.382 g (3.00 mmol), 0.40 mL (0.39 g, 3.1 mmol) of cyclohexylisocyanate in 20 mL of hexane, on standing for one day provides 0.664 g (88%) of 1-cyclohexyl-3-cyclooctylurea as white needles, mp 194.0-194.5° C. An infrared spectrum [3344 (s, NH), 3334 (s, NH), 1624 (vs, C=O), 1564 (vs. amide II) cm$^{-1}$] and mass spectrum [FAB-MS m/z calcd. for $C_{15}H_{28}N_2O$: 252, obsd: 253 (M+H$^+$)] confirms the identity of this material.

EXAMPLE 4

Cyclohexylcarbamothioic Acid S-Cyclohexyl Ester

To a solution of 0.61 mL (0.58 g, 5.0 mmol) of cyclohexylthiol in 25 mL of hexane is slowly added a solution of 0.626 g (5.00 mmol) of cyclohexylisocyanate in 5 mL of hexane. Adding one drop of 1,8-diazabicyclo[5.4.0]undec-7-ene initiates the formation of a white crystalline product. After several days at ambient temperature, the mixture is cooled, the cyclohexylcarbamothioic acid S-cyclohexyl ester is collected, washed with ice-cold hexane and dried to provide a 1.15 g (4.76 mmol, 95%) of product melting at 117.0-118.0° C. A confirmatory $^{13}$C-NMR (CDCl$_3$) is observed for this material: δ 165.9 (C=O), 50.3 (C-1), 42.4 (C-1'), 33.8 (C-2', 6'), 33.1 (C-2, 6), 26.0 (C-3', 5'), 25.5 (C-4$^1$), 25.4 (C-4), 24.7 (C-3, 5). Supportive infrared bands (KBr) are observed at 3343 (s, N—H), 1649 (vs, C=O), and 1206 (m, C—N) cm$^{-1}$.

EXAMPLE 5

Assay to Determine Inhibition of Soluble EH

Recombinant mouse sEH (MsEH) and human sEH (HsEH) were produced in a baculovirus expression system as previously reported. Grant et al., *J. Biol. Chem.*, 268:17628-17633 (1993); Beetham et al., *Arch. Biochem. Biophys.*, 305:197-201 (1993). The expressed proteins were purified from cell lysate by affinity chromatography. Wixtrom et aL, *AnaL Biochem.*, 169:71-80 (1988). Protein concentration was quantified using the Pierce BCA assay using bovine serum albumin as the calibrating standard. The preparations were at least 97% pure as judged by SDS-PAGE and scanning densitometry. They contained no detectable esterase or glutathione transferase activity which can interfere with the assay. The assay was also evaluated with similar results in crude cell lysates or homogenate of tissues.

The $IC_{50}$s for each inhibitor were determined by the spectrophotometric assay of Dietze et al. (Dietze et al., "Spectrophotometric Substrates for Cytosolic Epoxide Hydrolase," *Anal. Biochem.*, 216:176-187 (1994)) using cloned epoxide hydrolase genes expressed in the baculovirus system using racemic 4-nitrophenyl-trans-2,3-epoxy-3-phenylpropyl carbonate (NEP2C) as substrate. In a styrene 96-well microplate, 20 µl of enzyme preparation and 2 µl of the inhibitor solution in DMF ([I]final: 0.05 to 500 µM) were added to 180 µl of sodium phosphate (0.1 M, pH 7.4) containing 0.1 mg/ml of BSA. The mixture was incubated at 30° C. for 5 minutes. A substrate concentration of 40 µM was then obtained by adding 4 µl of a 2 mM solution. Activity was assessed by measuring the appearance of the 4-nitrophenolate at 405 nm at 30° C. for 1 minute (Spectramax 200; Molecular Device Inc., USA). Assays were performed in quadruplicate. By definition, the $IC_{50}$ is the concentration of inhibitor which reduces enzyme activity by 50%. $IC_{50}$s were determined by regression of at least five datum points with a minimum of two points in the linear region of the curve on either side of the $IC_{50}$. The curve was generated from at least four separate runs to obtain the standard deviation. In at least one run compounds of similar potency were included to insure rank order. A further rank order among very good compounds was determined with the $^3$H trans-stilbene oxide assay as described in Wixtrom and Hammock (below) or a related assay based on Borhan et al., "Improved Radiolabeled Substrates for Soluble Epoxide Hydrolase," *Anal. Biochem.*, 231:188-200 (1995). A similar partition assay based on $^3$H cis-stilbene oxide is described in Wixtrom et al., "Membrane-Bound and Soluble-Fraction Epoxide Hydrolases: Methodological Aspects," *Biochemical Pharmacology and Toxicology* (Zakim and Vessey, eds.), John Wiley & Sons, Inc., New York, 1:1-93 (1985).

EXAMPLE 6

Effect on Other Enzymes

Mammalian microsomal EH was assayed using $^3$H-cis-stilbene oxide, insect microsomal EH was assayed with 3H-juvenile hormone III, and $^3$H-trans-diphenyl-propene oxide, mammalian and plant cytosolic, and peroxisomal EHs were assayed using $^3$H-trans-diphenyl-propene oxide, P-450 was assayed using $^{3H}$-testosterone, carboxylic esterase assay used para-nitrophenylacetate, and gluthatione-S-transferase assay used chlorodinitrobenzene. Pepsin was assayed using hemoglobin as substrate.

It is to be understood that while the invention has been described above in conjunction with preferred specific embodiments, the description and examples are intended to illustrate and not limit the scope of the invention, which is defined by the scope of the appended claims.

EXAMPLE 7

This example shows that inhibitors of epoxide hydrolase are effective in decreasing blood pressure in mammals.

Methods

Animals. Male SHR and WKY rats 3-13 wks of age were purchased from Charles River Laboratories (Wilmington, Mass.) and housed in a controlled environment with 12 hr light/dark cycles and fed standard laboratory chow for □ 3 days before euthanasia. All animal use was approved by the University of California San Francisco Committee on Animal Research and followed the National Institutes of Health guidelines for the care and use of laboratory animals. For isolation of kidney subcellular fractions, rats were anesthetized with methoxyflurane, the abdominal cavities were opened, and the kidneys were perfused with ice-cold saline. Perfused kidneys were rapidly removed, the cortex and medulla dissected out and immersed in liquid nitrogen. All tissue was stored at −80° C. until preparation of microsomes. In some cases WKY and SHR rats were housed in metabolic cages for up to three days and urine was collected over triphenylphosphine in 24 hr intervals. The urine volume was noted and aliquots were stored at −80° C. prior to extraction and quantitation of DHETs and EETs. For the sEH inhibition studies, groups of 8 wk old male SHRs and WKY rats were treated daily for 1-4 days with a 3 mg/kg i.p. dose of N,N'-dicyclohexylurea (DCU) in a 1.5:1 mixture of corn oil and DMSO. Systolic blood pressure was measured at room temperature by a photoelectric tail cuff system (Model 179, IITC, Inc., Woodland Hills, Calif.) for up to four days following the dose of inhibitor. Blood pressures are reported as the average of three separate readings over a 30 min period. Urine was collected for 24 hr immediately following a dose of DCU or vehicle for quantification of DHET and EET excretion. Similar inhibition studies were carried out with equimolar doses of N-cyclohexyl-N'-dodecylurea, N-cyclohexyl-N'-ethylurea and dodecylaamine.

Renal microsomal arachidonic acid metabolism. Microsomes, cytosol, and S9 fractions were prepared from the renal cortex or outer medulla samples from a single animal as described previously (Kroetz, D. L. et al. Mol Pharmacol 52, 362-372 (1997), Su, P. et al. Am J Physiol 275, R426-438 (1998)). Reaction conditions for the in vitro determination of arachidonic acid epoxygenase activity, metabolite extraction and HPLC analysis were described in detail elsewhere (Su, P. et al. Am J Physiol 275, R426-438 (1998)).

Western immunoblotting. Renal and hepatic microsomes and cytosol (4 to 10 □g) were separated on a 8% sodium dodecyl sulfate-polyacrylamide gel and transferred to nitrocellulose in 25 mM Tris/192 mM glycine/20% methanol using a semidry transfer system (BioRad, Hercules, Calif.). The primary antibody used in these studies was a rabbit anti-mouse sEH antisera (Silva, M. H. et al. Comp. Biochem Physiol B: Comp Biochem 87, 95-102 (1987)). Western blots were incubated with a 1:2000 fold dilution of the primary antibody followed by a 1:2000-fold dilution of horseradish peroxidase-conjugated goat anti-rabbit IgG. Immunoreactive proteins were visualized using an ECL detection kit (Amersham Life Science, Arlington Heights, Ill.).

EET hydrolysis. Racemic [1-14C]EETs were synthesized and purified according to published methods from [1-14C] arachidonic acid (56-57 µCi/µmole) by nonselective epoxidation (Falck, J. R. et al., Meth Enzymol 187, 357-364 (1990)). Hydrolysis of [1-14C]EETs was measured in WKY and SHR renal S9 fractions at 37° C. as described previously (Zeldin, D. C. et al. J Biol Chem 268, 6402-6407 (1993)). The reaction mixture consisted of 50 μM EET (0.045-0.09 μCi) and 1 mg/ml S9 protein (0.5 mg/ml SHR S9 protein for 14,15-EET hydrolysis) in 150 mM KCl, 10 mM MgCl2, 50 mM potassium phosphate buffer pH 7.4. Reactions were carried out for 40 min (10 min for 14,15-EET hydrolysis in SHR samples) and the reaction products were extracted into ethyl acetate, evaporated under a blanket of nitrogen and detected by reverse phase HPLC with radiometric detection as described for the arachidonic acid incubations.

DHET urinary excretion. Urinary creatinine concentrations were measured by the Medical Center Clinical Laboratories at the University of California San Francisco. Methods used to quantify endogenous EETs and DHETs present in rat urine were similar to those described by Capdevila et al. (Capdevila, J. H. et al. J Biol Chem 267, 21720-21726 (1992)). DHET and [1-14C]DHET internal standards were prepared by chemical hydration of EETs and [1-14C]EETs as described (Zeldin, D. C. et al. J Biol Chem 268, 6402-6407 (1993)). All synthetic EETs and DHETs were purified by reverse-phase HPLC. EET quantifications were made by GC/MS analysis of their pentafluorobenzyl (PFB) esters with selected ion monitoring at m/z 319 (loss of PFB from endogenous EET-PFB) and m/z 321 (loss of PFB from [1-14C]EET-PFB internal standard). The EET-PFB/[1-14C]EET-PFB ratios were calculated from the integrated values of the corresponding ion current intensities. Quantifications of DHETs were made from GC/MS analysis of their PFB esters, trimethylsilyl (TMS) ethers with selected ion monitoring at m/z 481 (loss of PFB from endogenous DHET-PFB-TMS) and m/z 483 (loss of PFB from [1-14C]DHET-PFB-TMS internal standard). The DHET-PFB-TMS/[1-14C]DHET-PFB-TMS ratios were calculated from the integrated values of the corresponding ion current intensities. Data were normalized for kidney function by expressing per mg creatinine. Control studies demonstrated that under the conditions used, artifactual EET or DHET formation was negligible.

Other enzyme assays. Activities of microsomal and soluble EH were determined in liver and kidney samples according to previously published protocols (Gill, S. S. et al., Anal Biochem 131, 273-282 (1983); Borhan, B., et al., Anal Biochem 231, 188-200 (1995)). Inhibition of recombinant soluble EH by DCU was described recently (Morisseau, C., et al. Proc. Natl. Acad. Sci. USA 96, 8849-8854, (1999)). Epoxide hydrolase activities are reported as the transdiol formation rates.

Statistics. Statistical significance of differences between mean values was evaluated by a one-way analysis of variance or a Student's t-test. Significance was set at a p value of <0.05.

Results

The spontaneously hypertensive rat (SHR) is a well accepted experimental model of essential hypertension and was used in the present study to characterize the contribution of EET hydrolysis to the elevated blood pressure in these animals. Renal transplantation studies support a role for the kidneys in the development of hypertension in the SHR and altered renal function is essential for the development and maintenance of elevated blood pressure (Bianchi, G. et al., Clin Sci Mol Med 47, 435-448 (1974); Cowley, A. W. et al., JAMA 275, 1581-1589 (1996)). Arachidonic acid metabolism was measured in renal cortical microsomes of SHR and WKY rats and a dramatic increase in DHET formation was observed in the SHR relative to the WKY samples (FIG. 1). The formation of 11,12- and 8,9-DHET was measurable in both strains and was 2- to 8-fold higher in the SHR relative to the WKY rat throughout their development (FIG. 1A and 1B). Interestingly, 14,15-DHET formation was readily detected in the 3-13 wk old SHR kidneys but could not be measured in the majority of the WKY samples (FIG. 1C). In the several instances where 14,15-DHET formation was detectable in the WKY kidneys it was never greater than 17% of the corresponding value in SHR. Calculation of the percentage of EETs that were converted to the corresponding DHETs revealed a large discrepancy between the WKY and SHR strains. In the WKY renal microsomes 32±3.1% of the EETs were converted to DHETs, while the DHET recovery was 66±2.1% in the SHR renal microsomes (p<0.00001).

Figure 2:
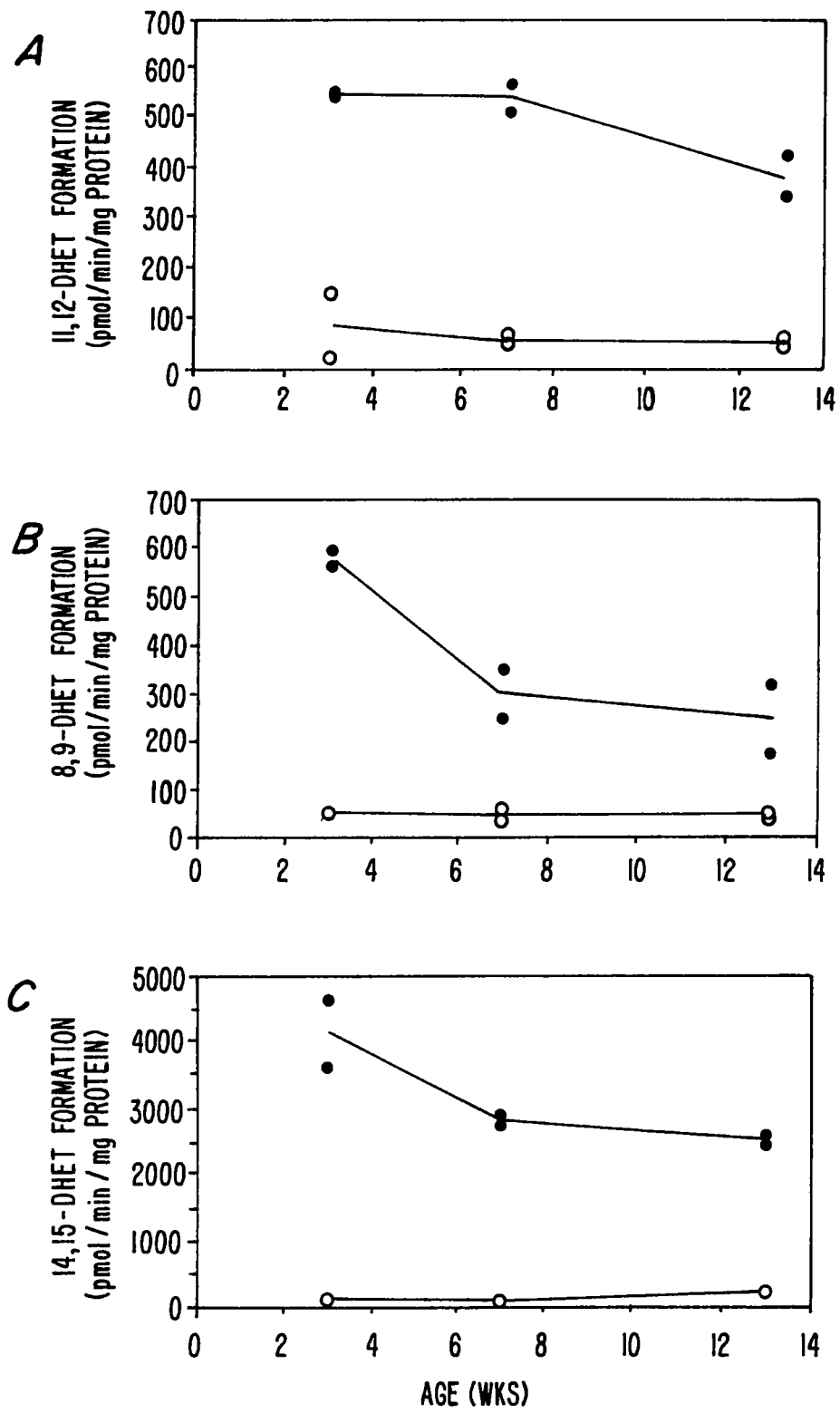

A dramatic increase in DHET formation in incubations of arachidonic acid with SHR renal cortical microsomes relative to the WKY samples (FIG. 1) led us to hypothesize that EET hydrolysis may be altered in this experimental model of hypertension and that epoxide hydrolase activity may be an important determinant of blood pressure regulation. Two major EH isoforms, a microsomal (mEH) and soluble (sEH) form are expressed in most tissues and species (Vogel-Bindel, U. et al., Eur J Biochem 126, 425-431 (1982); Kaur, S. et al., Drug Metab Disp 13, 711-715 (1985)). EET hydrolysis rates in cytosol and microsomes and the regioisomeric product distribution in urine relative to recombinant EH proteins are consistent with the majority of EET hydrolysis being catalyzed by sEH (Zeldin, D. C. et al., J Biol Chem 268, 6402-6407, (1993)). Direct hydrolysis of the regioisomeric EETs was measured in S9 fractions (containing both the soluble and microsomal forms of EH) from WKY and SHR renal cortex. There was measurable hydrolysis of 8,9-, 11,12- and 14,15-EET in S9 fractions from both WKY and SHR kidneys (FIG. 2), with a significant increase in hydrolysis in the SHR relative to the WKY. For example, 8,9- and 11,12-EET hydrolysis rates were 5- to 15-fold higher in the SHR compared to the WKY and 14,15-EET hydrolysis was as much as 54-fold higher in the SHR. These data also showed a distinct preference of sEH for the 14,15-EET regioisomer. In the SHR kidney hydrolysis of 14,15-EET was 10-fold higher than that of 8,9- and 11,12-EET.

Figure 3A:
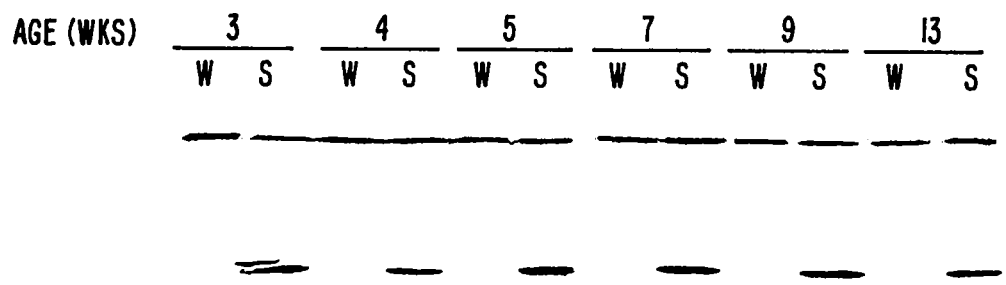
FIG. 3 shows that sEH expression is increased in the SHR kidney relative to the WKY kidney and that DHET urinary excretion is also increased in the SHR. (A) Microsomal proteins from WKY (W) and SHR (S) renal cortex were separated on a 8% SDS-polyacrylamide gel, transferred to nitrocellulose, and blotted with antisera against rat mEH (top panel) or mouse sEH (bottom panel). The age of the rats is indicated on the top of the blot. (B) Microsomal (top panel) and cytosolic (bottom panel) proteins from WKY (W) and SHR (S) cortex, outer medulla and liver were separated and transferred as described above and blotted with antisera against mouse sEH. A renal cortex sample from a Sprague-Dawley (SD) rat and a purified recombinant sEH protein sample are also included on the blot. Immunoreactive proteins were detected by chemiluminescence. The blots are representative of the results from three to six animals/experimental group. (C) Urine was collected for 24 hr from untreated WKY rats (solid bars) and SHR (hatched bars). DHETs were extracted from urine and quantified by GC-MS as described in the Methods section. The values shown are the means ±SE of four animals/strain. Significant differences between WKY and SHR are indicated (p<0.0005).
Figure 3B:
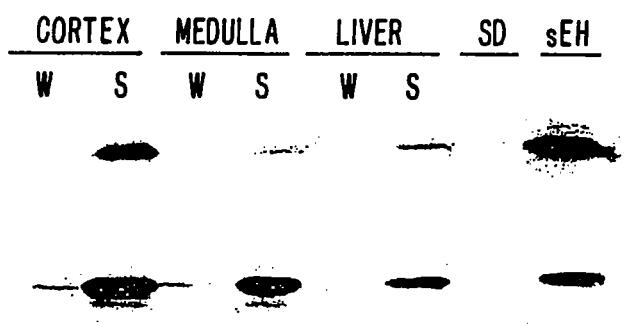

To investigate the possibility that altered EH expression is responsible for the differences in EET hydrolysis in the SHR and WKY rat renal microsomes and S9 fractions, we measured EH protein levels in these samples. mEH was abundantly expressed in the renal microsomes at relatively constant levels throughout development and there was no evidence of altered expression of mEH in the SHR kidney (FIG. 3A). The soluble EH isoform was also easily detected in SHR cortical microsomes but not in the corresponding WKY samples (FIG. 3A). Quantitation of the immunoreactive protein bands indicated that levels of sEH protein in the SHR microsomes were 6- to 90-fold higher than the corresponding levels in the WKY microsomes. The high levels of expression of sEH in the SHR microsomes were limited to the renal cortex (FIG. 3B). Immunodetectable sEH was barely detectable in SHR outer medulla and liver microsomes by Western blot. Relatively high levels of sEH were detected in SHR cortex, outer medulla and liver cytosol (FIG. 3B). In the WKY rats, the level of sEH protein was uniformly low in both microsomes and cytosol from the kidney and liver. Importantly, sEH protein in the normotensive Sprague-Dawley rat kidney was also barely detectable. Increased sEH expression in SHR vs. WKY rats provides an explanation for the increased EET hydrolysis in the SHR kidney and the absence or very low levels of 14,15-EET hydrolysis, the preferred sEH substrate (Zeldin, D. C., et al., J Biol Chem 268, 6402-6407 (1993)), in the WKY kidney.

Increased sEH activity in the SHR kidney was independently confirmed using the sEH substrate trans-1,3-diphenylpropene oxide (tDPPO). There was a 26-fold increase in tDPPO hydrolysis in the SHR cortical cytosol relative to that of the WKY rat cortical cytosol (Table 2). The corresponding difference in the microsomal fraction was 32-fold. Hydrolysis of tDPPO was also significantly higher in SHR vs. WKY rat liver microsomes and cytosol. Consistent with the Western blots, sEH activity was easily detectable in the SHR microsomes and very low in the WKY cytosol and microsomes from kidney. In contrast, mEH activity, as measured by cSO hydrolysis, was similar in WKY and SHR cortex and liver (Table 2).

Figure 3C:
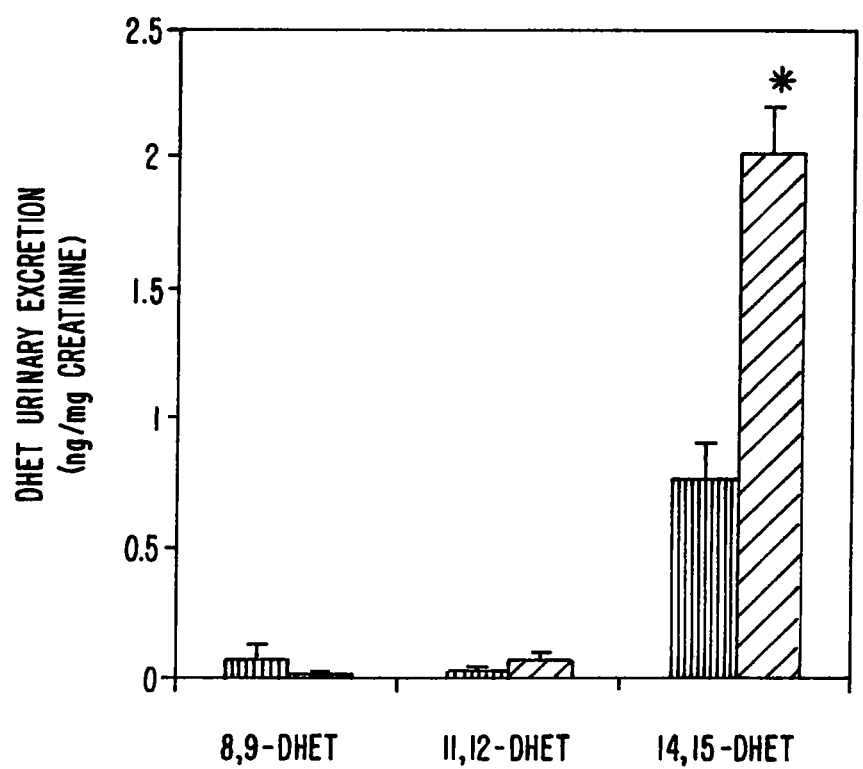

Urinary excretion of DHETs was measured to evaluate whether increased sEH expression and EET hydrolysis in the SHR was also apparent in vivo. Urine was collected in untreated 4 and 8 wk old SHR and WKY rats and their DHET excretion rates are shown in FIG. 3C. The excretion rates were similar for the 4 and 8 wk animals and the reported numbers are averages from all samples of a given strain. The excretion of 14,15-DHET was 2.6-fold higher in the SHR relative to the WKY rat, consistent with the increased EET hydrolysis and sEH expression in SHR kidney. In contrast, the 8,9- and 11,12-DHET urinary excretion in the SHR and WKY rats were comparable.

A tight binding sEH specific inhibitor, dicyclohexylurea (DCU) (Morisseau, C. et al., Proc Natl Acad Sci USA 96, 8849-8854 (1999)), was used to reduce sEH activity in vivo and to determine the effect of decreased EET hydrolysis on blood pressure. Inhibition of EET hydrolysis by DCU was confirmed in incubations of renal S9 fractions with the regioisomeric EETs (FIG. 4A). A dose-dependent inhibition of EET hydrolysis by DCU was apparent for all three regioisomers. DCU had the most significant effect on the hydrolysis of 8,9-EET, inhibiting this reaction with an IC50 of 0.086±0.014 □M. The corresponding IC50 values for inhibition of 11,12- and 14,15-EET hydrolysis were 0.54±0.08 □M and 0.45±0.16 □M, respectively. At concentrations up to 25 □M, DCU had no effect on CYP epoxygenase or □-hydroxylase activity and previous studies from our laboratory have shown that DCU does not inhibit mEH (Morisseau, C. et al., Proc Natl Acad Sci USA 96, 8849-8854 (1999)). The potent inhibition of sEH by DCU was confirmed with purified recombinant rat sEH. DCU inhibited sEH-catalyzed tDPPO hydrolysis with a Ki of 34 nM. This is comparable to the Ki values for DCU with human (30 nM) and murine (26 nM) sEH (Morisseau, C. et al., Proc Natl Acad Sci USA 96, 8849-8854 (1999)).

DCU was administered to eight wk old SHRs daily for four days and urinary DHET excretion was measured during the 24 hr period immediately following the third dose. The dose of DCU was based on in vitro estimates of inhibitory potency and previous studies in the mouse (Morisseau, C. et al., Proc Natl Acad Sci USA 96, 8849-8854 (1999). In the DCU-treated rats there was a significant 65% decrease in 14,15-DHET urinary excretion and a corresponding 30% increase in 14,15-EET urinary excretion relative to vehicle-treated controls (FIG. 4B), consistent with DCU-mediated inhibition of sEH in vivo. The excretion of total epoxygenase-derived products (EETs and DHETs) was decreased from 2020 pg/mg creatinine in the vehicle-treated animals to 1237 pg/mg creatinine in the DCU-treated rats (p<0.05). This inhibition of 14,15-DHET excretion was accompanied by a significant decrease in blood pressure measured in conscious animals three to five hr after the fourth dose. Systolic blood pressure decreased from 128±5 mm Hg in the vehicle-treated rats to 102±5 mm Hg (p<0.01) in the DCU-treated animals.

Figure 4:
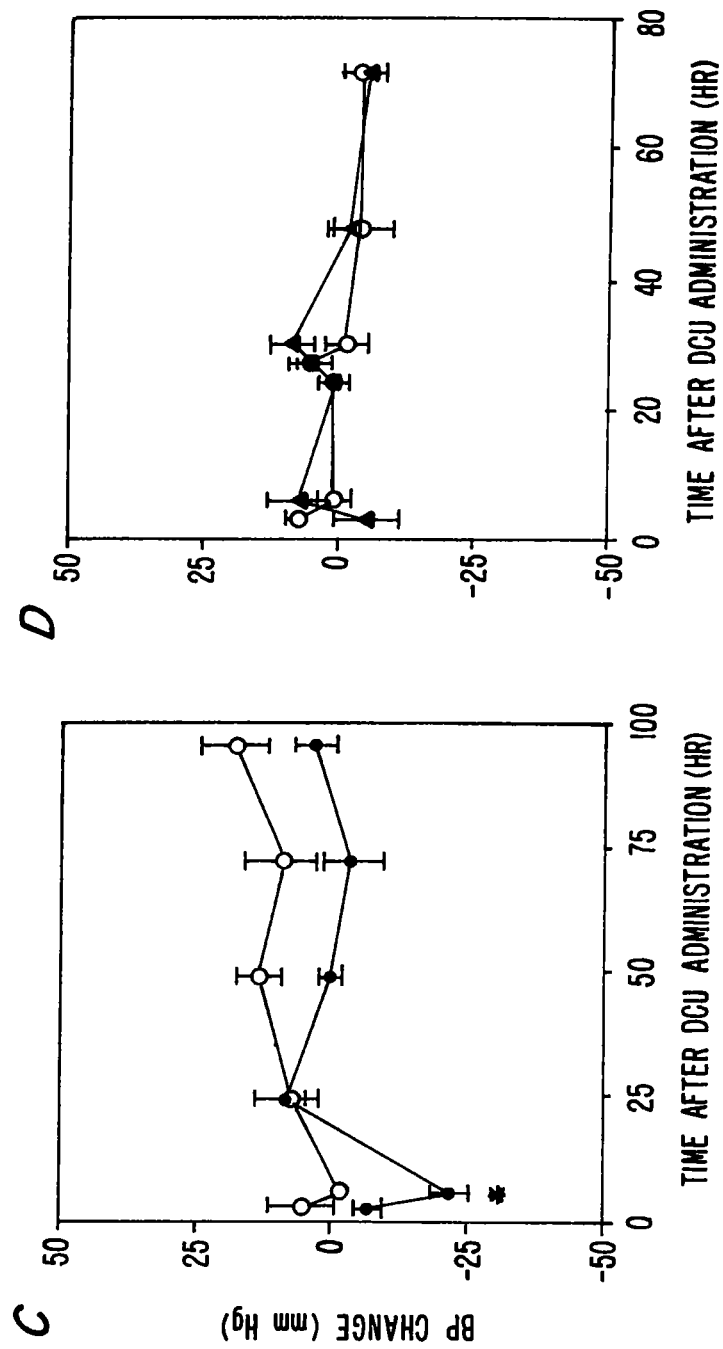
FIG. 4 shows that DCU is a potent and selective inhibitor of sEH and has antihypertensive effects in the SHR. (A) The formation of $[1-^{14}C]$11,12-(A), 8,9-(B), and 14,15-DHET (C) from $[1-^{14}C]$EETs (50 µM) was measured in SHR renal S9 fractions in the presence of increasing concentrations of DCU. The values shown are the average of two samples/concentration, expressed as % of control. The difference between the individual values was 7-33%. Control formation rates were 7193 pmol/min/mg protein for 14,15-DHET, 538 pmol/min/mg protein for 11,12-DHET, and 595 pmol/min/mg protein for 8,9-DHET. DCU was a potent and selective inhibitor of EET hydrolysis in vitro. (B) Urine was collected for 24 hr following treatment of SHR with vehicle (solid bars) or DCU (hatched bars) daily for 3 days. EETs and DHETs were extracted from urine and quantified by GC-MS as described in the Methods section. The values shown are the means ±SE of four animals/strain. Significant differences between vehicle- and DCU-treated SHR are indicated (p<0.05). DCU was a potent inhibitor of 14,15-EET hydrolysis in vivo. (C) Male SHR rats were treated with a single 3 mg/kg dose of DCU (●) or vehicle (○). Systolic blood pressure was measured with a photoelectric tail cuff for up to 96 hr after the dose. The values shown are the mean ±SE from DCU- and vehicle-treated rats (n=5/group). Baseline systolic blood pressure was 143±3 mm Hg in the SHRs. (D) Male WKY rats were treated with a single 3 mg/kg dose of DCU (●) or vehicle (○). Systolic blood pressure was measured with a photoelectric tail cuff for up to 96 hr after the dose. The values shown are the mean ±SE from DCU- and vehicle-treated rats (n=5/group). Baseline systolic blood pressure was and 118±2 mm Hg in the WKY rats. Blood pressure decreased an average of 22 mm Hg in the DCU-treated SHRs 6 hr after the dose (p<0.01) and was unaffected by DCU in the WKY rats.
Figure 4A:
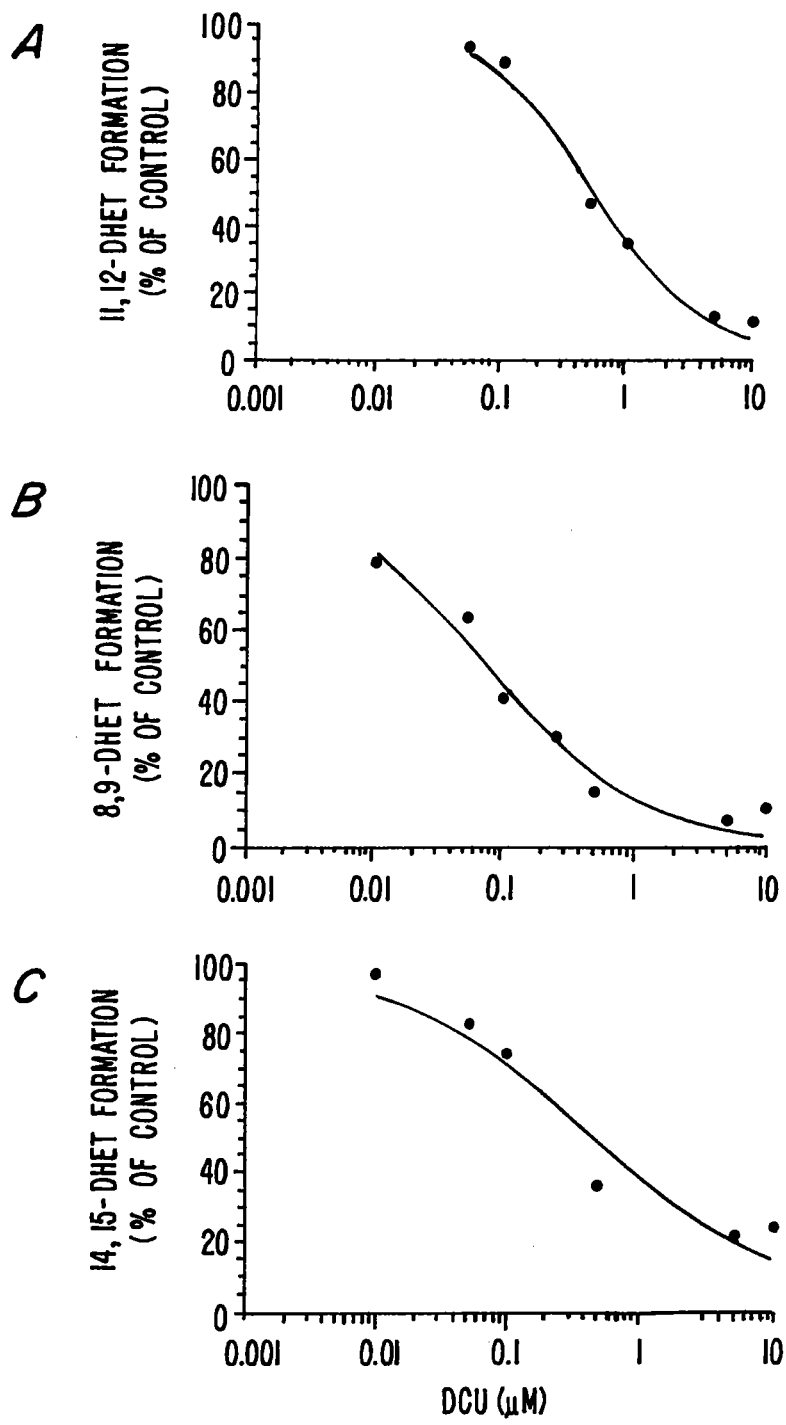
Figure 4B:
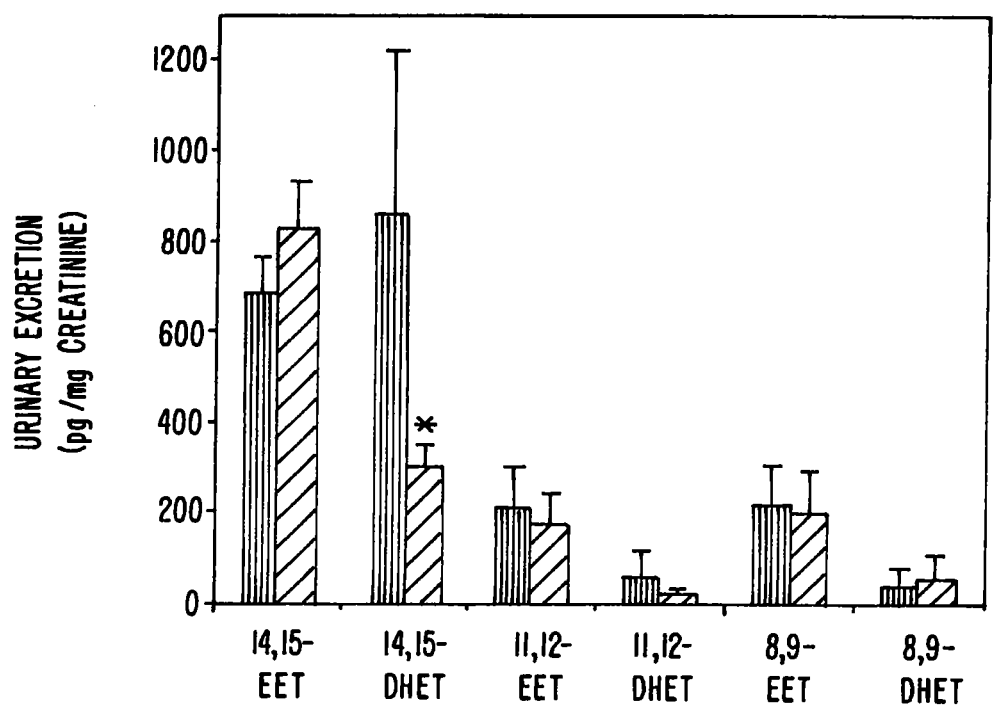
Figure 5:
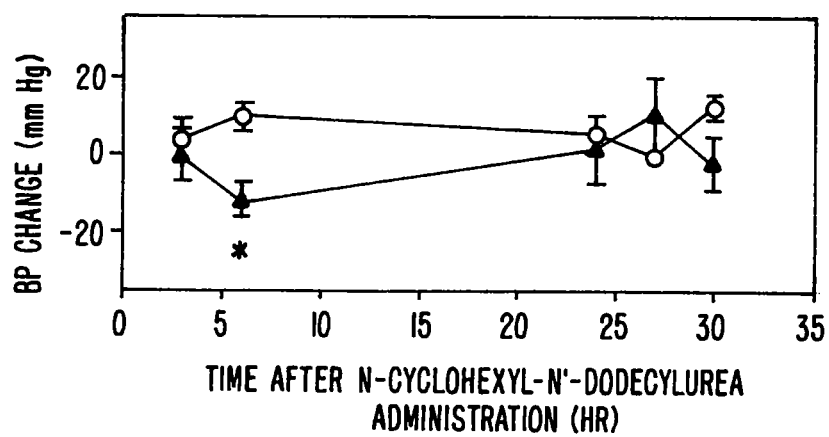
FIG. 5 shows that a structurally related urea inhibitor of sEH also has antihypertensive effects in the SHR. Male SHRs were treated with a single dose of vehicle (○) or N-cyclohexyl-N'-dodecylurea (●) (equimolar to 3 mg/kg DCU). Systolic blood pressure was measured with a photoelectric tail cuff for 24 hr after the dose. The values shown are the mean ±SE from inhibitor- and vehicle-treated rats (n=5/group). Baseline systolic blood pressures were 135±5 mm Hg in the N-cyclohexyl-N'-dodecylurea group. Blood pressure decreased an average of 12 mm Hg in the N-cyclohexyl-N'-dodecylurea-treated SHRs 6 hr after the dose (p<0.01).
Figure 6:
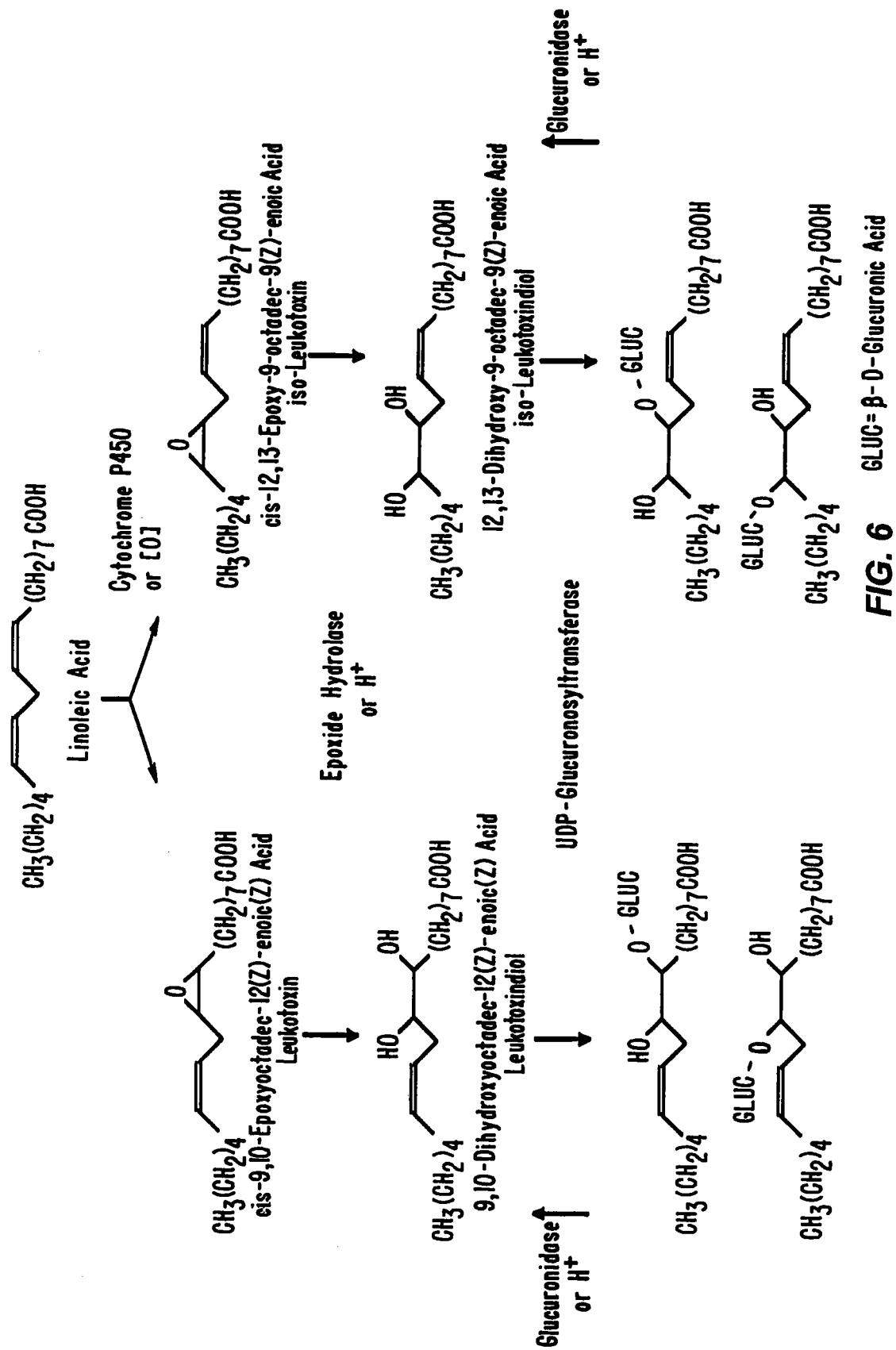
FIG. 6 shows the metabolic pathway for linoleic acid, the most abundant fatty acid in the average American diet. As shown in the Figure, linoleic acid can be epoxidized at either or both of the double bonds. The epoxides can be converted by the soluble epoxide hydrolase into 1,2-diols which can then be conjugated.

A study of the time course of the effect of a single dose of DCU (3 mg/kg) demonstrated that the antihypertensive effect in the SHR was acute (FIG. 4C). Blood pressure was decreased 22±4 mm Hg 6 hr after DCU treatment (p<0.01) and returned to baseline levels by 24 hr after the dose. Importantly, there was no effect of DCU on blood pressure in the WKY (FIG. 4D). This is consistent with the very low levels of sEH protein in the WKY kidney. Several additional structurally related inhibitors were also studied in the SHR. N-cyclohexyl-N'-dodecylurea is a sEH inhibitor with similar potency to DCU (IC50 with mouse sEH=0.05±0.01 compared to 0.09±0.01 □M for DCU; unpublished data, C. Morisseau and B. Hammock, 2000). A single dose of N-cyclohexyl-N'-dodecylurea significantly decreased systolic blood pressure 12±2 mm Hg 6 hr after the dose, and similar to DCU, blood pressure returned to normal by 24 hours after the dose (FIG. 5). The N-cyclohexyl-N'-ethylurea analog is a weak sEH inhibitor (IC50 with mouse sEH=51.7±0.7 □M; unpublished data, C. Morisseau and B. Hammock, 2000) and had no effect on blood pressure in the SHR. Likewise, the selective mEH inhibitor dodecylamine also had no effect on blood pressure. Collectively, these data suggest that the effect of DCU and N-cyclohexyl-N'-dodecylurea on blood pressure is related to their ability to inhibit sEH and EET hydrolysis in vivo.

Discussion

The EET eicosanoids are recognized as important mediators of vascular tone and renal tubular sodium and water transport (Makita, K. et al., FASEB J 10, 1456-1463 (1996)). These data provide substantial evidence in support of the protective role of the EETs. The potential protective effects of increased EET formation in the SHR kidney are attenuated by an even greater increase in FET hydrolysis. Increased expression of sEH in the SHR kidney results in increased EET hydrolysis in vitro and in vivo and therefore lower levels of the antihypertensive EETs. In contrast, inhibition of EET hydrolysis in vivo is associated with elevated EET levels and a reduction in blood pressure. Importantly, this provides a common link between the pathophysiological regulation of blood pressure in rats and humans (Catella, F. et al., Proc Natl Acad Sci USA 87, 5893-5897 (1990)). The 8,9-DHET regioisomer is easily detected in the urine of healthy women while excretion of 14,15- and 11,12-DHET is minimal in this population. For all three isomers DHET excretion is increased during a normal pregnancy and during pregnancy-induced hypertension 14,15- and 11,12-DHET excretion increased even further. This was most dramatic for 14,15-EET, the preferred substrate for sEH (Zeldin, D. G. et al., J Biol Chem 268, 6402-6407 (1993)). The excretion of 14,15-DHET increased from a median of 85 pg/mg of creatinine during normal pregnancy to 2781 pg/mg of creatinine in women with pregnancy-induced hypertension. Pharmacokinetic evidence is consistent with a renal origin of the urinary DHETs (Catella, F. et al., Proc Natl Acad Sci USA 87, 5893-5897 (1990)) so altered EET and DHET levels could potentially affect tubular ion transport and/or renal vascular tone. The present results in the SHR support the possibility that sEH expression is altered in women with pregnancy induced hypertension.

Inhibition of EET hydrolysis is a new therapeutic approach to regulating renal eicosanoid formation. Recently, inhibition of arachidonic acid ω-hydroxylase activity with a mechanism-based CYP inhibitor has been shown to effectively lower blood pressure in the SHR (Su, P. et al., Am J Physiol 275, R426-438 (1998)). The approach of inhibition of EET hydrolysis in the present study produces a significantly greater decrease in blood pressure than the CYP inhibition strategy. The possibility exists of a synergistic effect of CYP4A inhibition resulting in decreased levels of the prohypertensive 20-HETE eicosanoid and sEH inhibition leading to increased levels of the antihypertensive EETs. Parallel inhibition of related enzymes is a limitation of CYP epoxygenase and co-hydroxylase inhibition but is of little concern with sEH inhibition. These findings make it of interest to fully characterize the impact of sEH inhibition on renal tubular ion transport, vascular tone and blood pressure. The possibility of similar changes in sEH activity in human hypertensive populations is compelling. Identification of individuals with elevated sEH activity may prove useful in designing the most effective antihypertensive therapy.

It is to be understood that while the invention has been described above in conjunction with preferred specific embodiments, the description and examples are intended to illustrate and not limit the scope of the invention, which is defined by the scope of the appended claims. All publications, sequences referred to in GenBank accession numbers, patents, and patent applications cited herein are hereby incorporated by reference for all purposes.

What is claimed is:

1. A method of treating inflammation in an inflammatory disorder of the lung in a patient in need thereof, comprising administering to said patient a therapeutically effective amount of an inhibitor of soluble epoxide hydrolase ("sEH"), wherein said inhibitor of sEH is a compound selected from the group consisting of:

(compound no. 72)

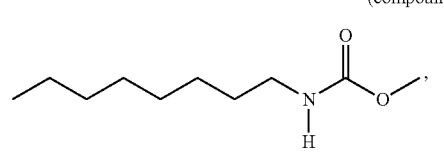

(compound no. 248)

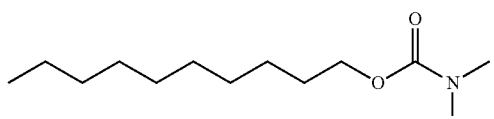

(compound no. 42)

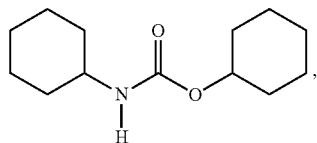

(compound no. 224)

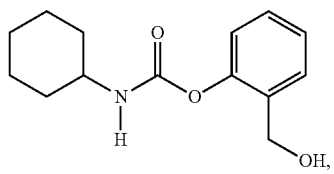

(compound no. 225)

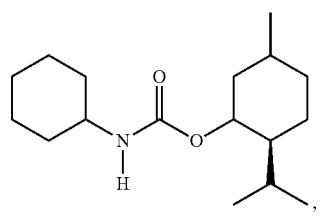

(compound no. 276)

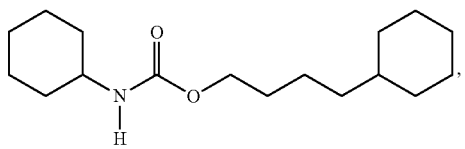

(compound no. 277)

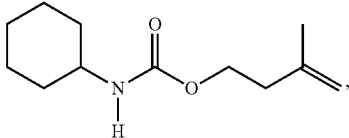

(compound no. 460)

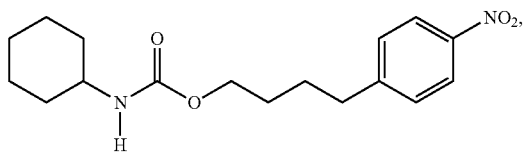

(compound no. 110)

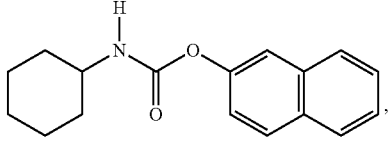

(compound no. 259)

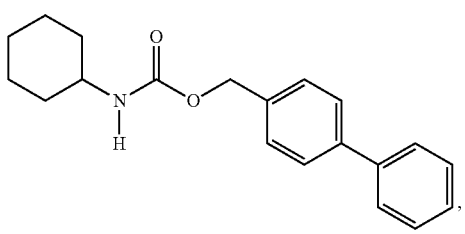

(compound no. 260)

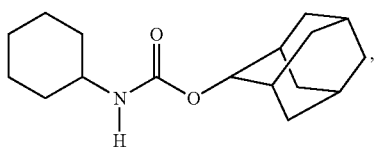

(compound no. 261)

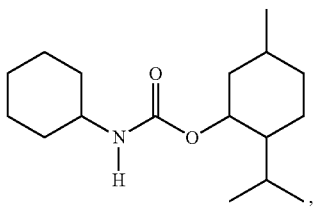

(compound no. 262)

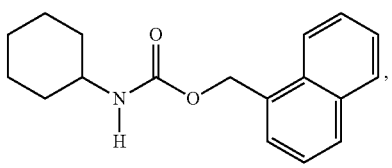

(compound no. 263)
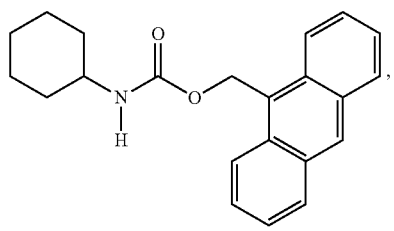
(compound no. 255)
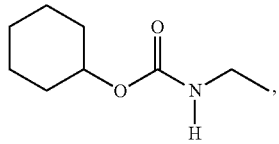
(compound no. 514)
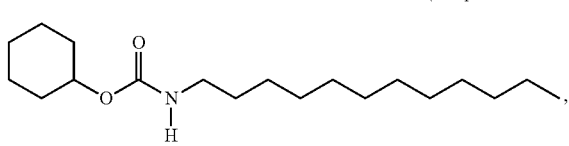
(compound no. 515)
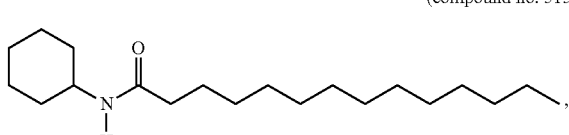
(compound no. 187)
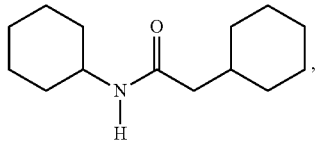
(compound no. 374)
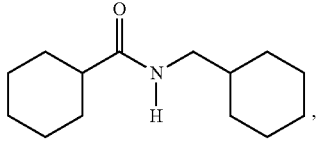
(compound no. 381)
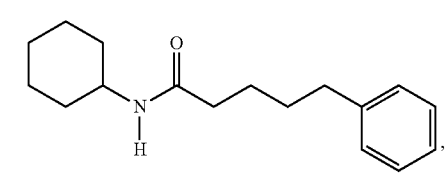
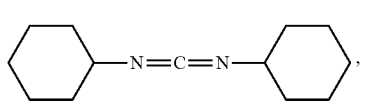
(compound no. 189)
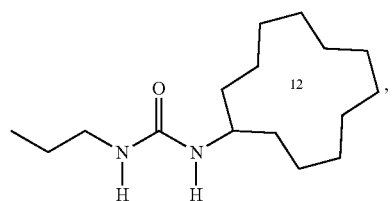
(compound no. 375)
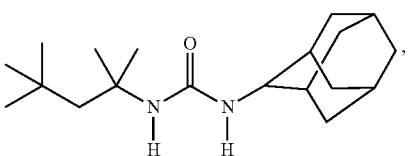
(compound no. 157)
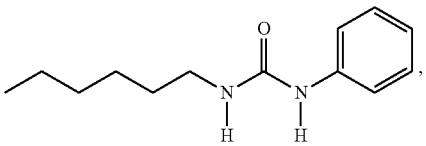
(compound no. 143)
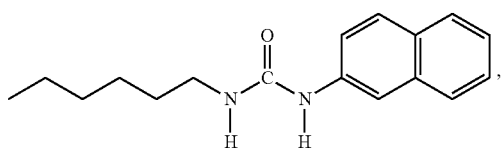
(compound no. 178)
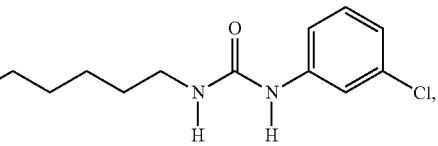
(compound no. 380)
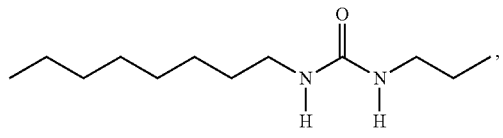
(compound no. 125)
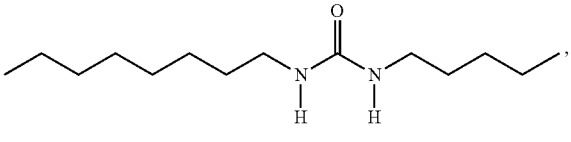
(compound no. 183)
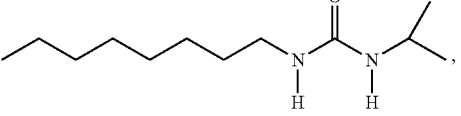
(compound no. 175)
(compound no. 181)
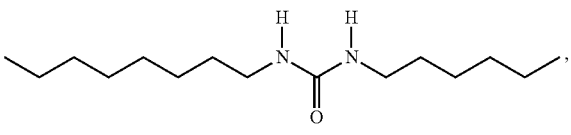

(compound no. 168)
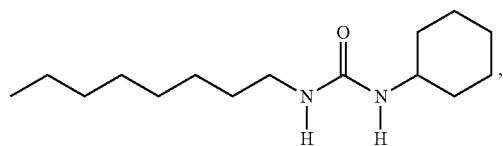
(compound no. 151)
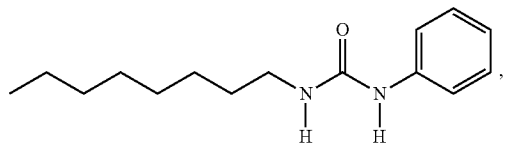
(compound no. 170)
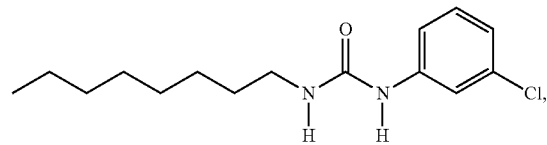
(compound no. 429)
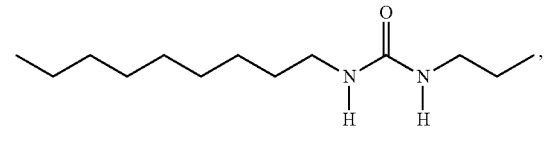
(compound no. 153)
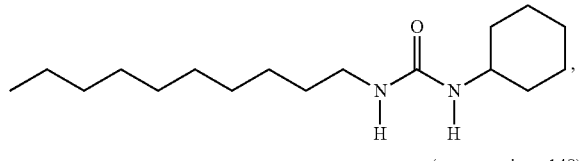
(compound no. 148)
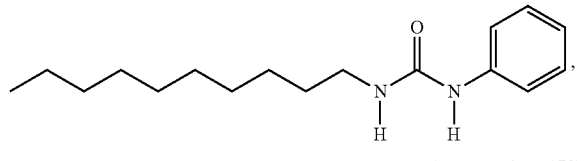
(compound no. 172)
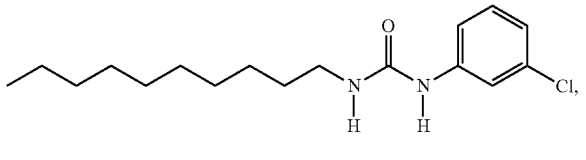
(compound no. 556)
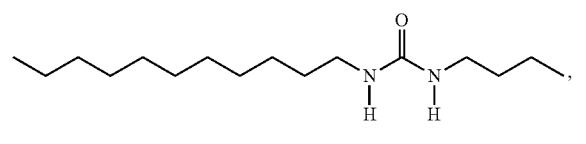
(compound no. 478)
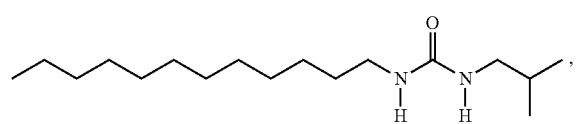
(compound no. 562)
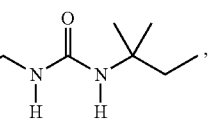
(compound no. 531)
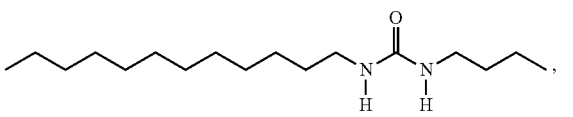
(compound no. 504)
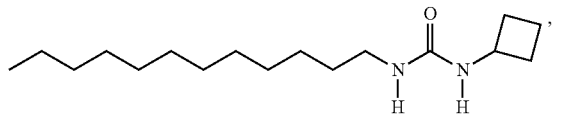
(compound no. 479)
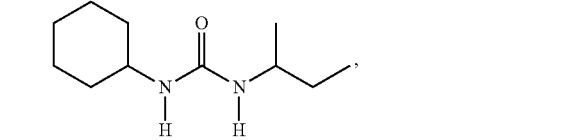
(compound no. 103)
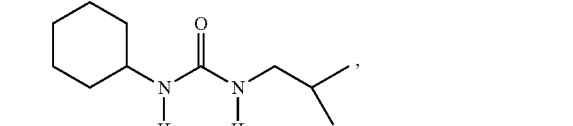
(compound no. 347)
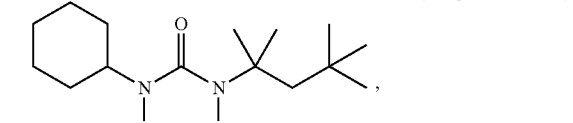
(compound no. 124)
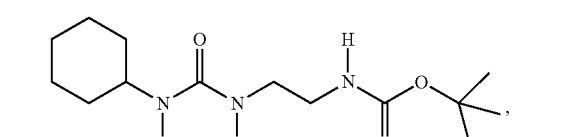
(compound no. 509)
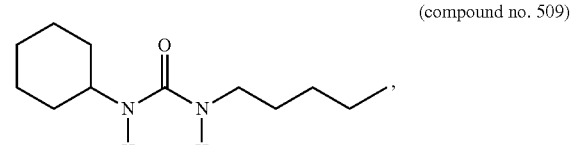
(compound no. 286)
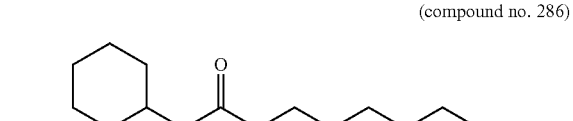
(compound no. 344)
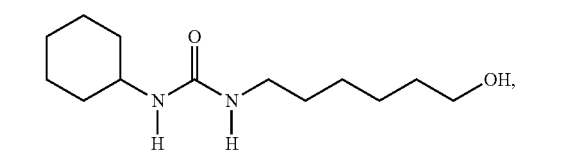

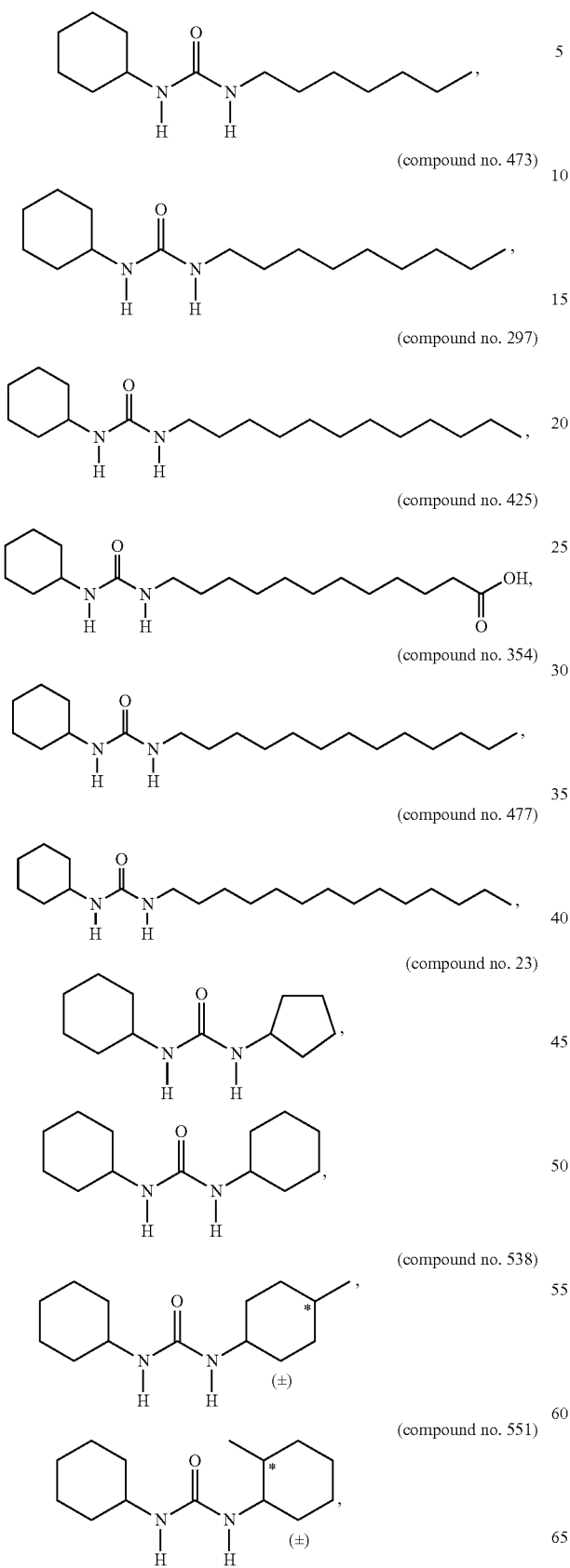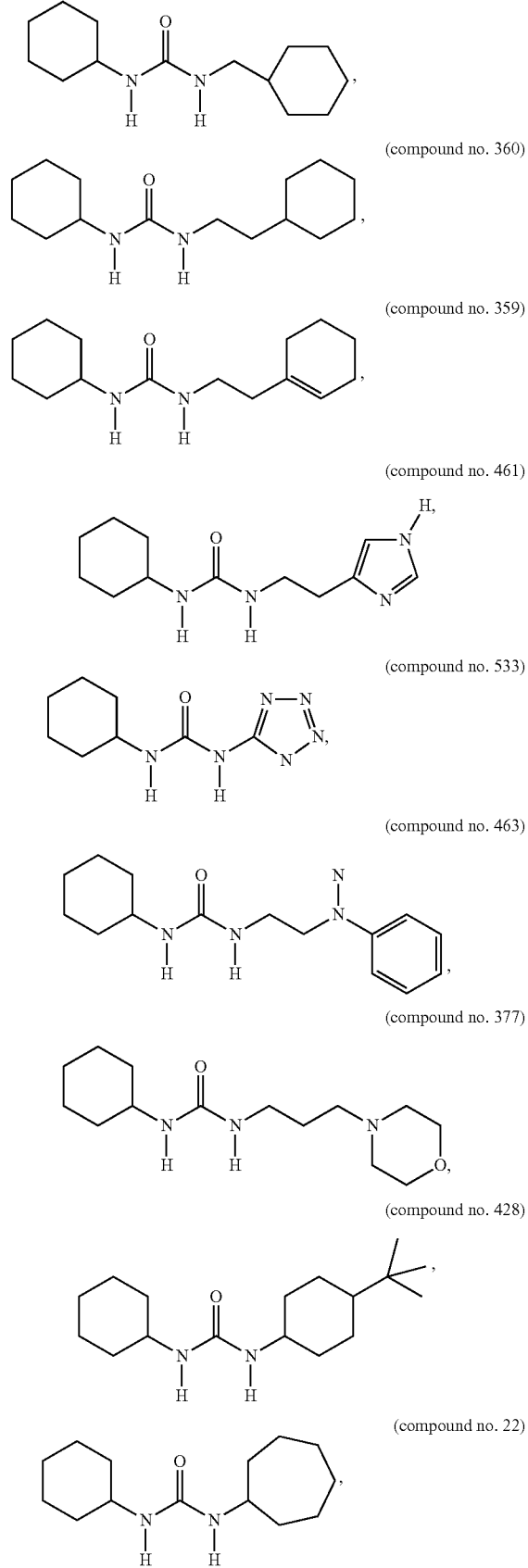

(compound no. 58)
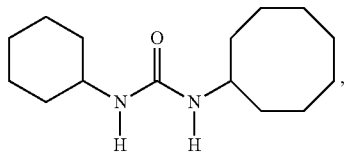
(compound no. 119)
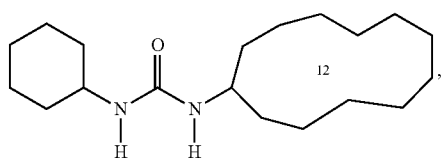
(compound no. 543)
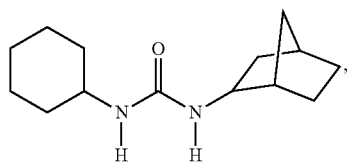
(compound no. 192)
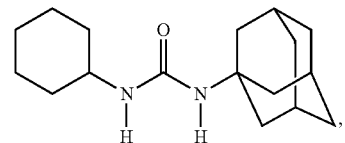
(compound no. 427)
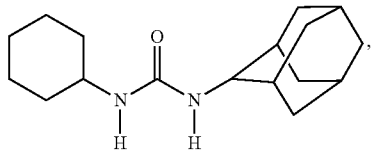
(compound no. 358)
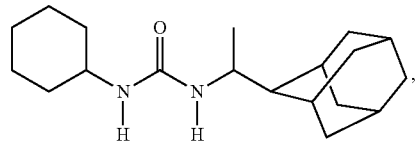
(compound no. 21)
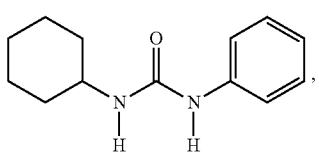
(compound no. 435)
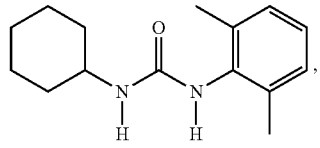
(compound no. 270)
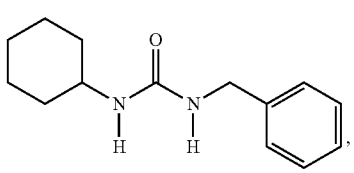
(compound no. 544)
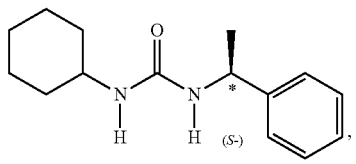
(compound no. 545)
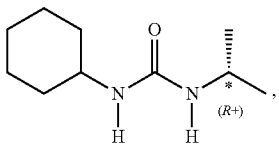
(compound no. 437)
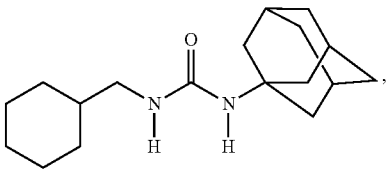
(compound no. 176)
(compound no. 36)
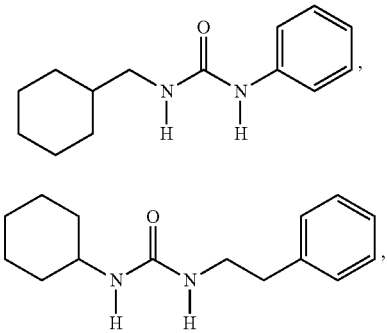
(compound no. 104)
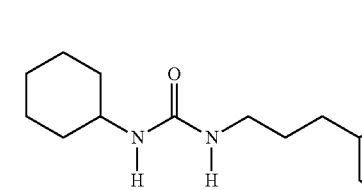
(compound no. 105)
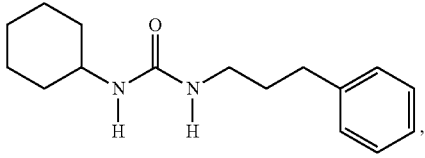
(compound no. 100)
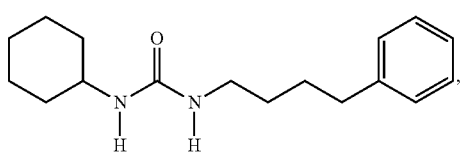
(compound no. 188)
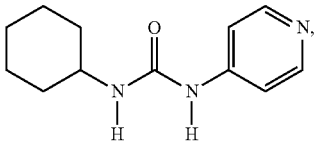

(compound no. 434)
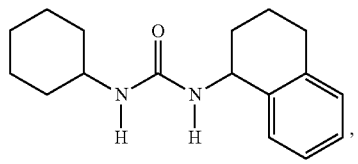
(compound no. 59)
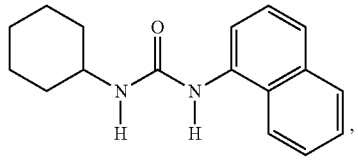
(compound no. 559)
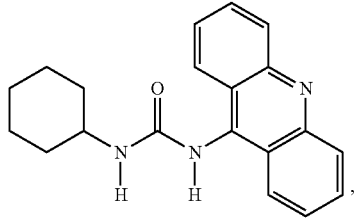
(compound no. 169)
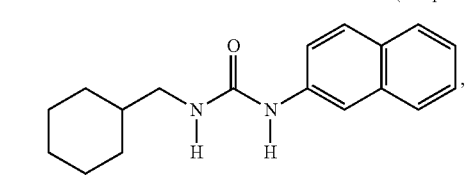
(compound no. 140)
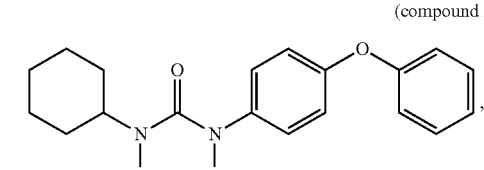
(compound no. 108)
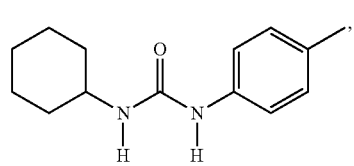
(compound no. 67)
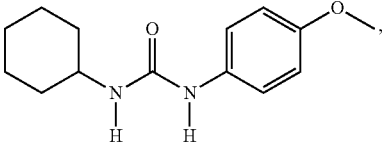
(compound no. 384)
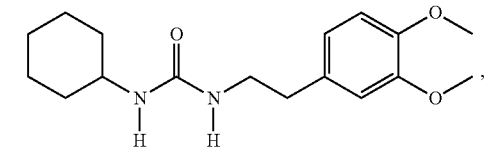
(compound no. 343)
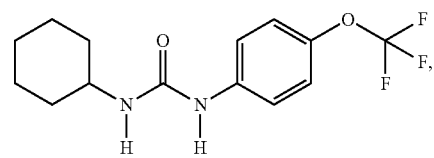
(compound no. 118)
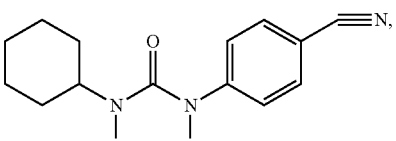
(compound no. 126)
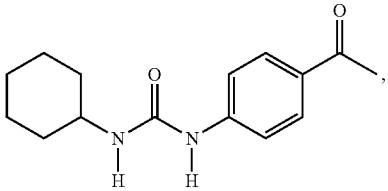
(compound no. 66)
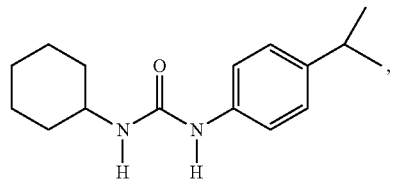
(compound no. 180)
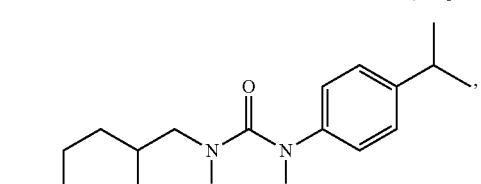
(compound no. 75)
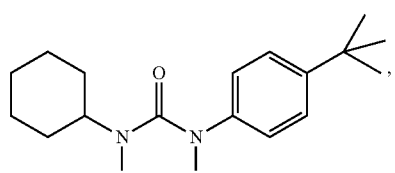
(compound no. 501)
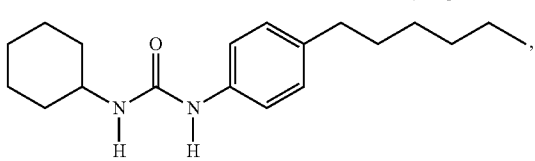
(compound no. 60)
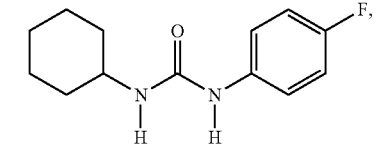
(compound no. 20)
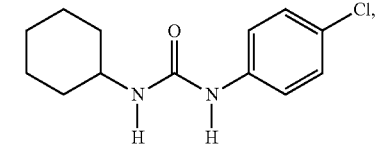

(compound no. 193)
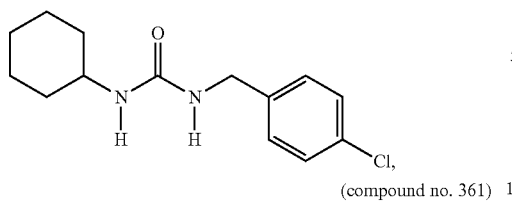
(compound no. 361)
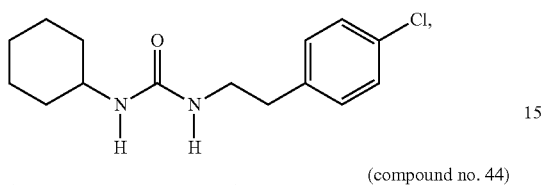
(compound no. 44)
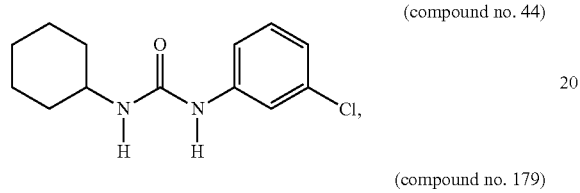
(compound no. 179)
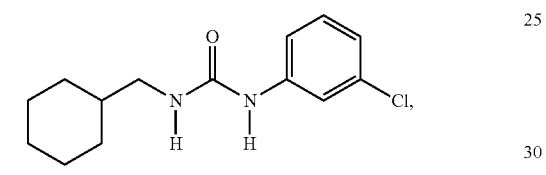
(compound no. 65)
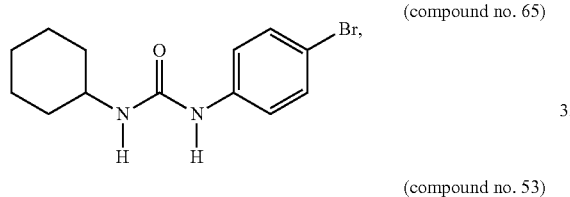
(compound no. 53)
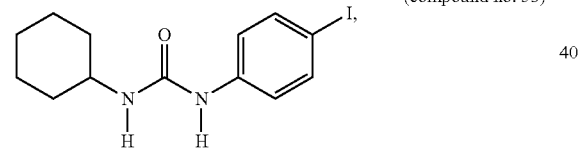
(compound no. 385)
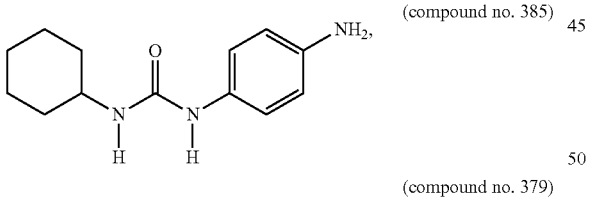
(compound no. 379)
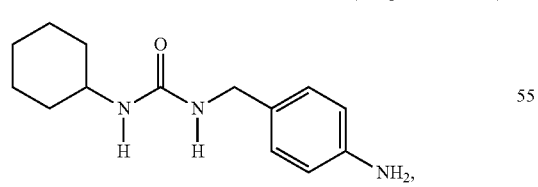
(compound no. 362)
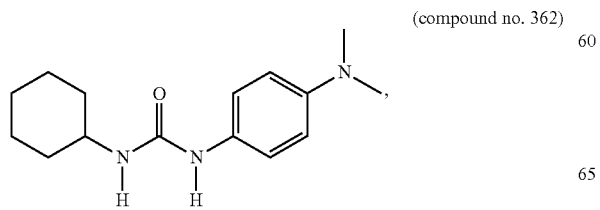
(compound no. 38)
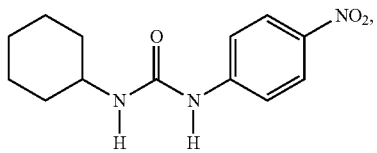
(compound no. 341)
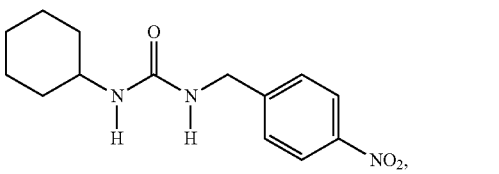
(compound no. 128)
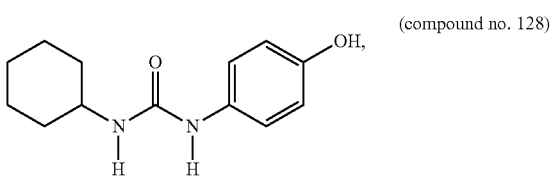
(compound no. 411)
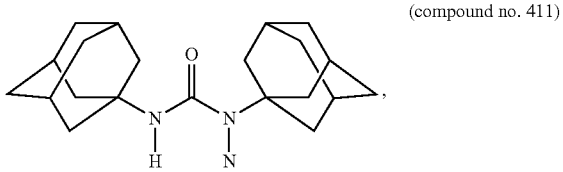
(compound no. 412)
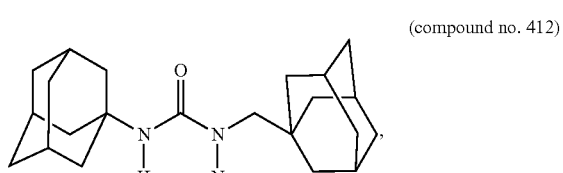
(compound no. 413)
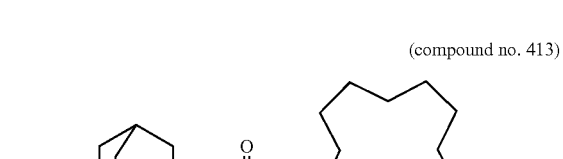
(compound no. 438)
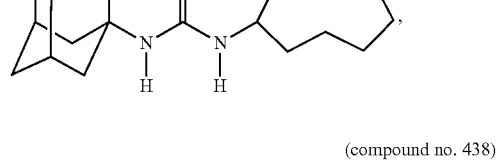
(compound no. 430)
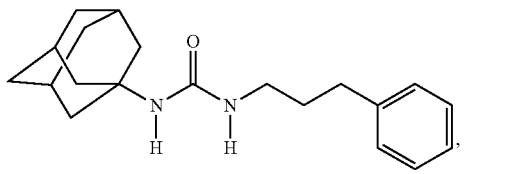
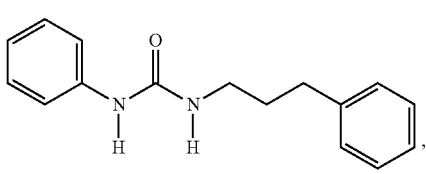

(compound no. 470)

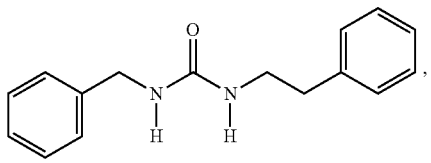

(compound no. 471)

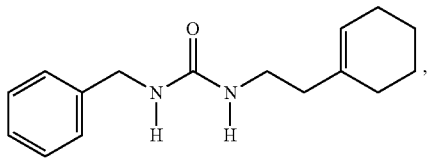

(compound no. 159)

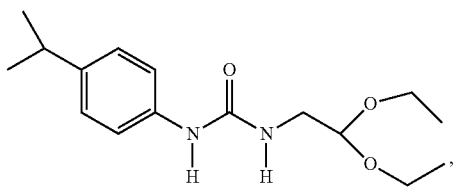

(compound no. 156)

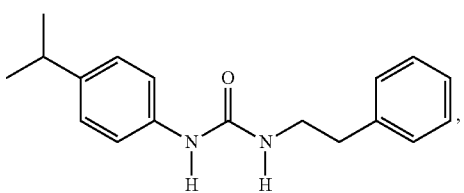

(compound no. 287)

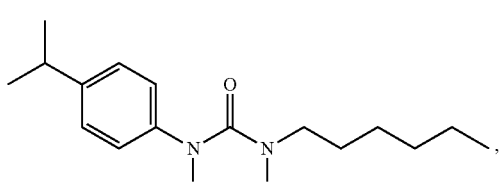

(compound no. 167)

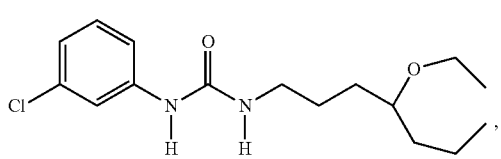

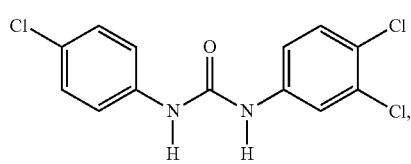

(compound no. 299)

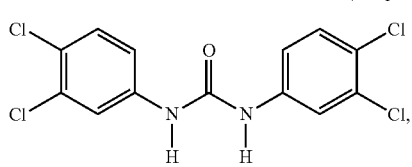

(compound no. 253)

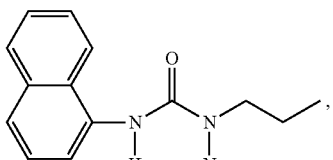

(compound no. 283)

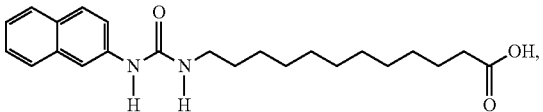

and (compound no. 257)

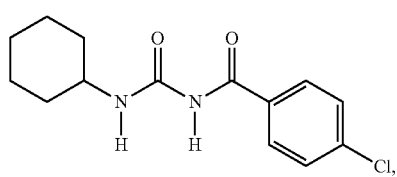

or a pharmaceutically acceptable salt thereof, whereby the inflammation is treated.

2. A method of treating inflammation in a subject with adult respiratory distress syndrome ("ARDS"), comprising administering to said patient a therapeutically effective amount of an inhibitor of soluble epoxide hydrolase ("sEH"), wherein said inhibitor is a compound selected from the group consisting of:

(compound no. 72)

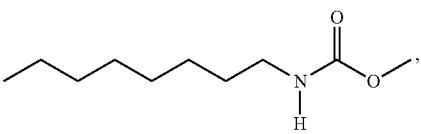

(compound no. 248)

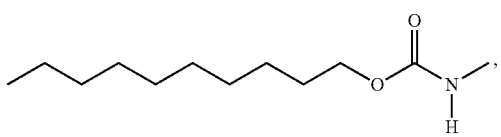

(compound no. 42)

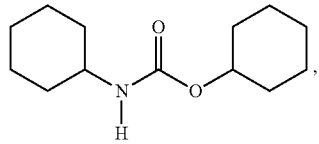

(compound no. 224)

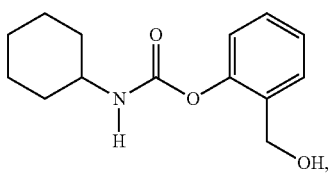

(compound no. 225)
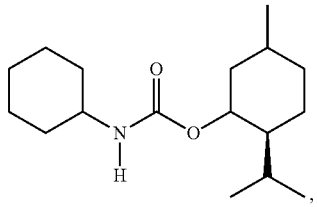
(compound no. 276)
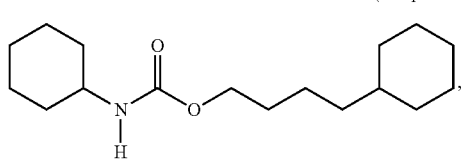
(compound no. 277)
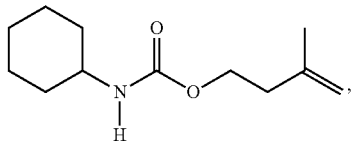
(compound no. 460)
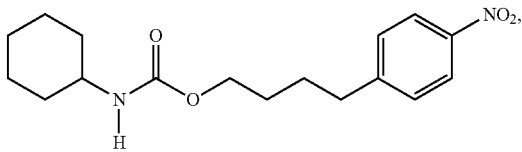
(compound no. 110)
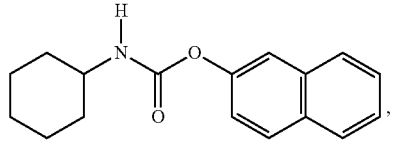
(compound no. 259)
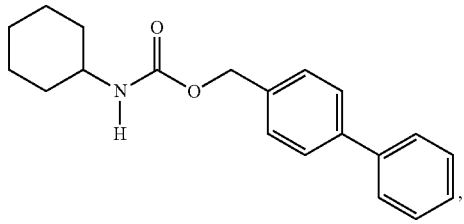
(compound no. 260)
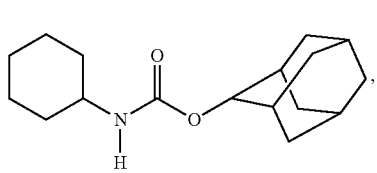
(compound no. 261)
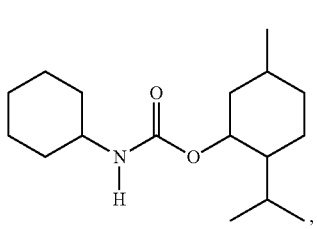
(compound no. 262)
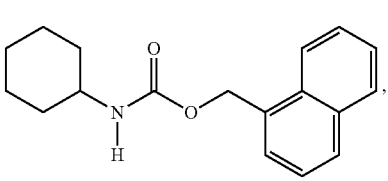
(compound no. 263)
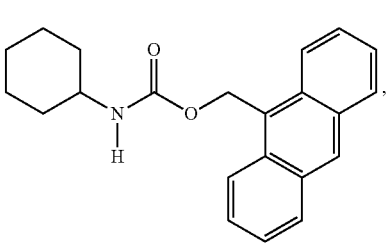
(compound no. 255)
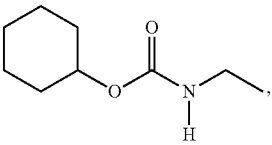
(compound no. 514)
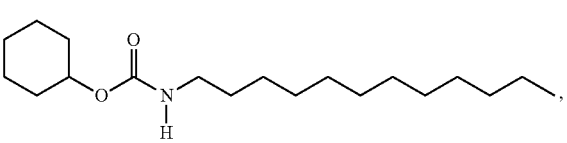
(compound no. 515)
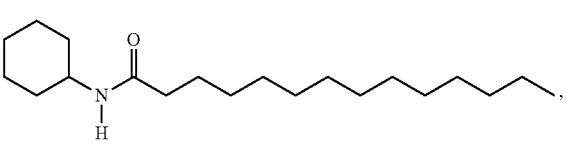
(compound no. 187)
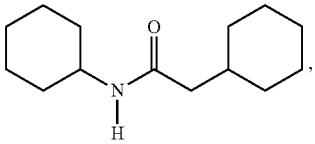
(compound no. 374)
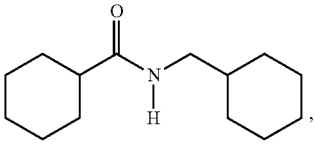
(compound no. 381)
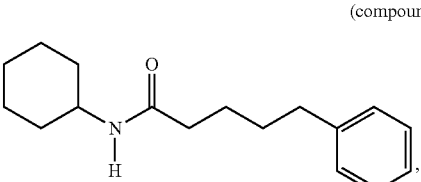
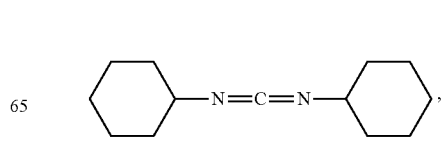

(compound no. 189)
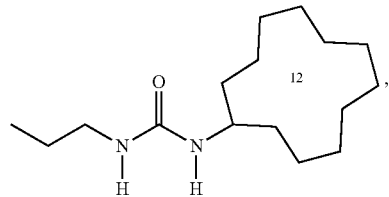
(compound no. 375)
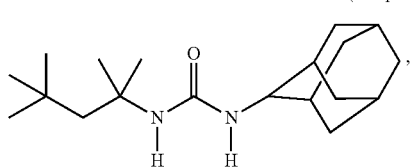
(compound no. 157)
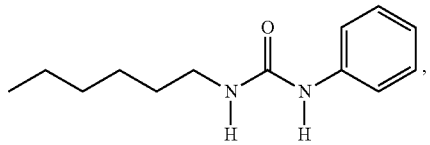
(compound no. 143)
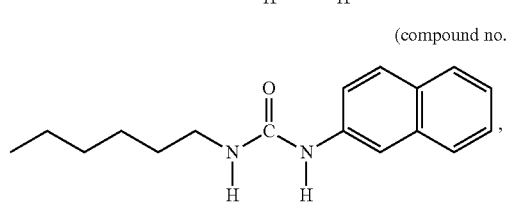
(compound no. 178)
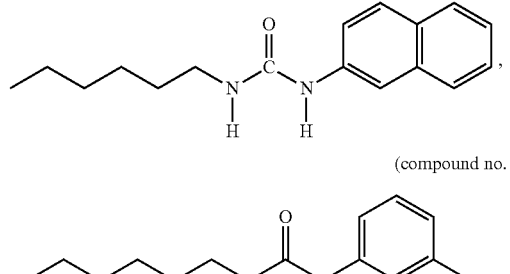
(compound no. 380)
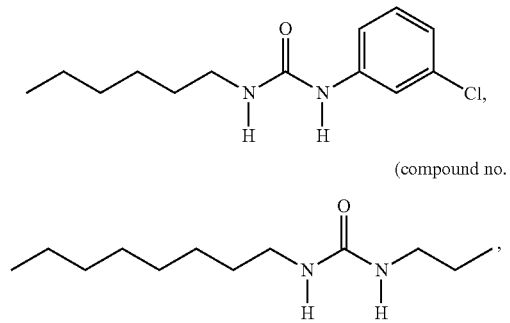
(compound no. 125)
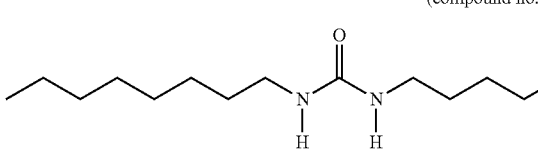
(compound no. 183)
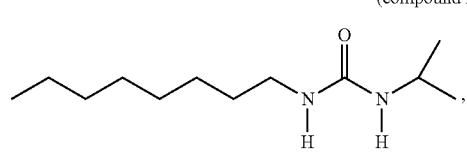
(compound no. 175)
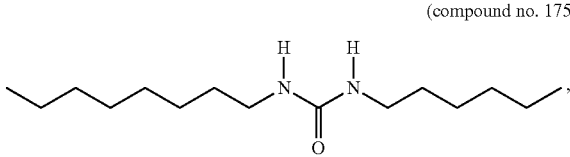
(compound no. 181)
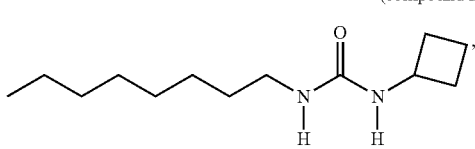
(compound no. 168)
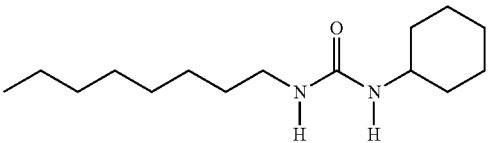
(compound no. 151)
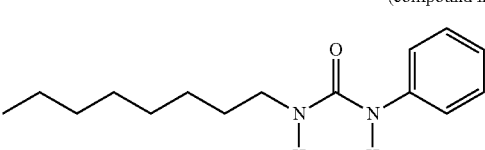
(compound no. 170)
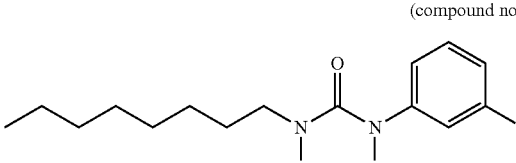
(compound no. 429)
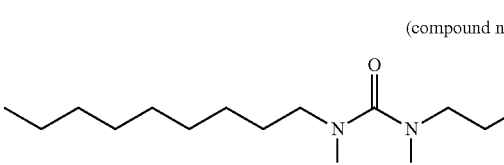
(compound no. 153)
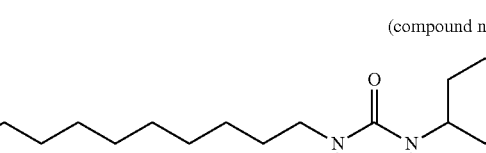
(compound no. 148)
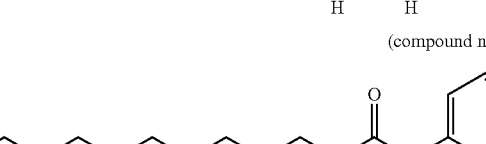
(compound no. 172)
(compound no. 556)
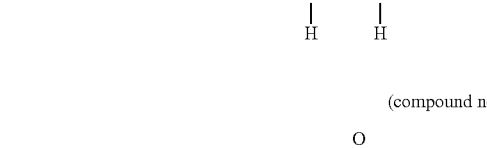

-continued
(compound no. 478)
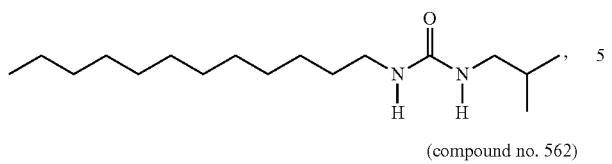
(compound no. 562)
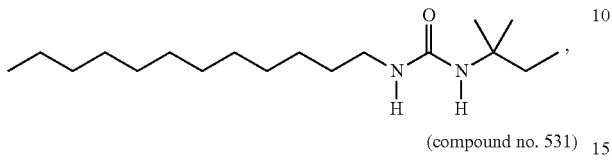
(compound no. 531)
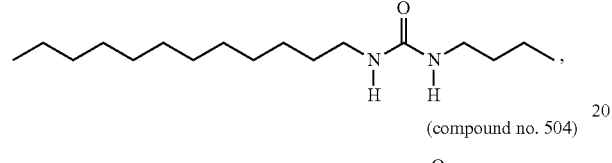
(compound no. 504)
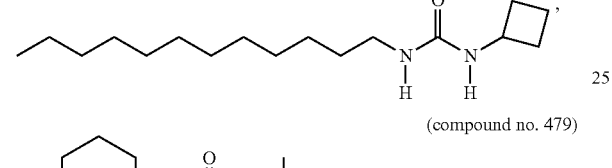
(compound no. 479)
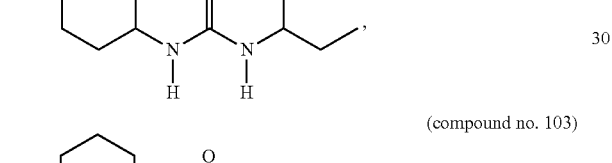
(compound no. 103)
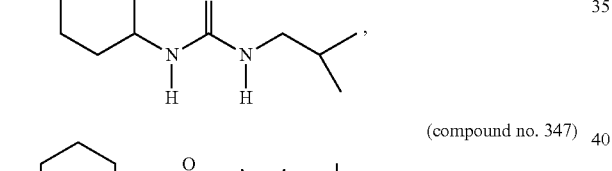
(compound no. 347)
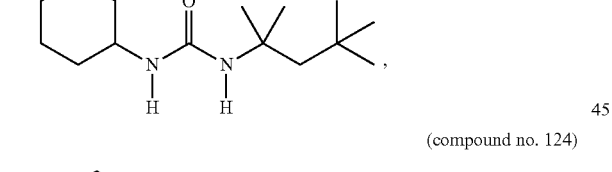
(compound no. 124)
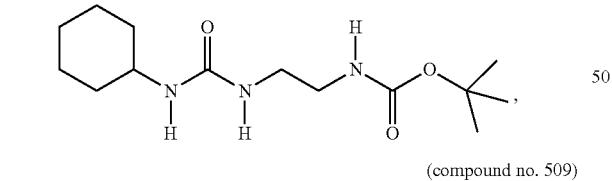
(compound no. 509)
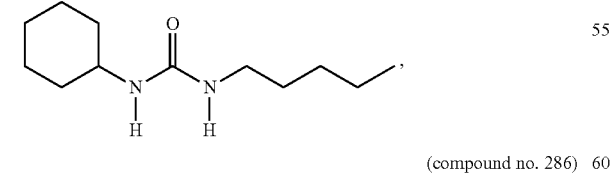
(compound no. 286)
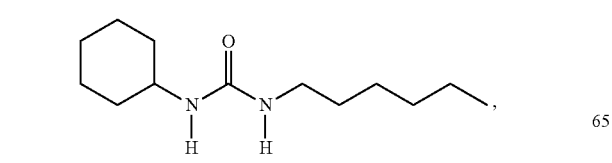
-continued
(compound no. 344)
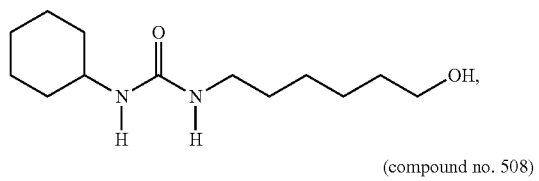
(compound no. 508)
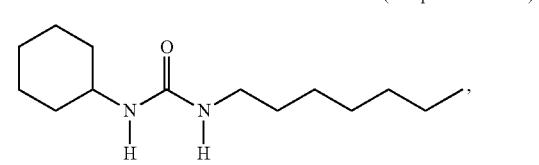
(compound no. 473)
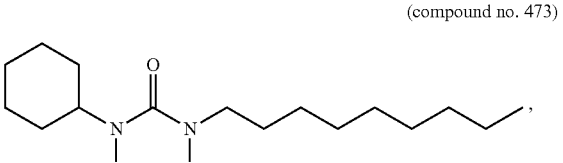
(compound no. 297)
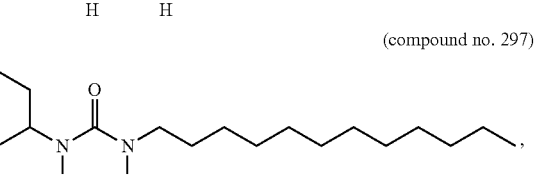
(compound no. 425)
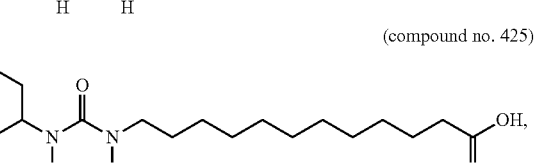
(compound no. 354)
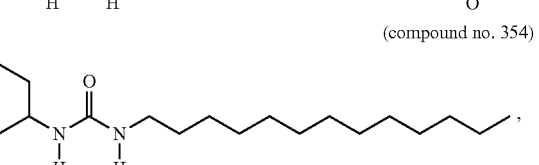
(compound no. 477)
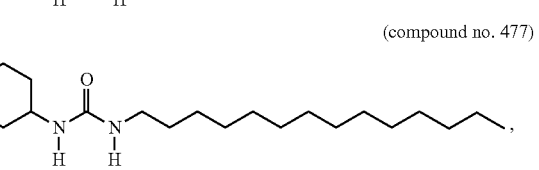
(compound no. 23)
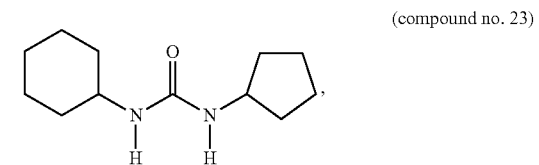
(compound no. 538)
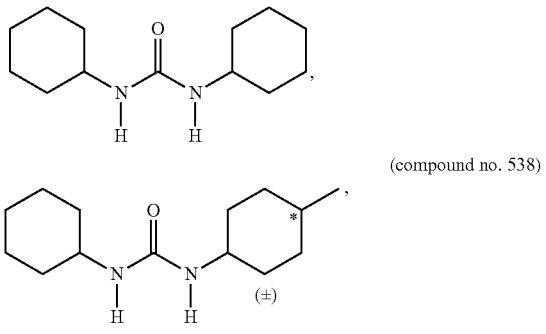

(compound no. 551)
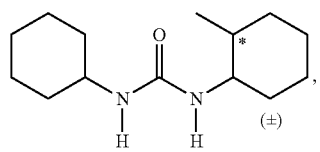
(compound no. 57)
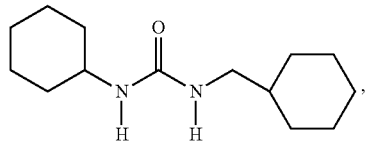
(compound no. 360)
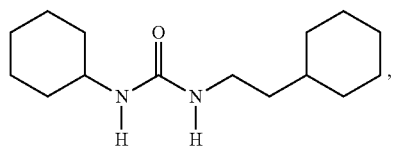
(compound no. 359)
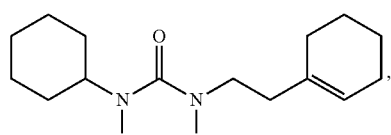
(compound no. 461)
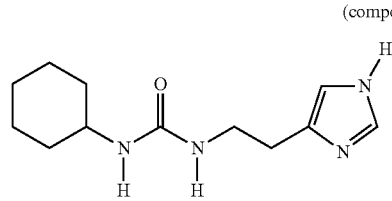
(compound no. 533)
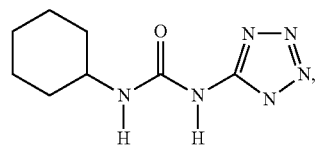
(compound no. 463)
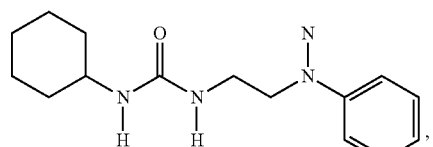
(compound no. 377)
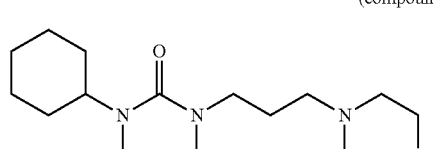
(compound no. 428)
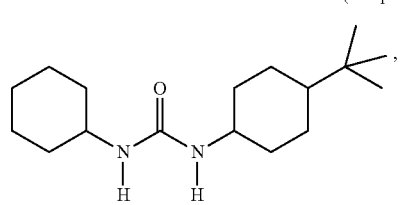
(compound no. 22)
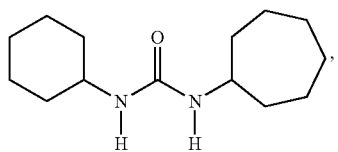
(compound no. 58)
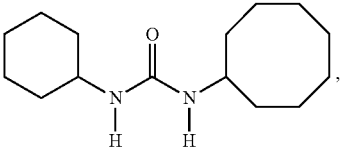
(compound no. 119)
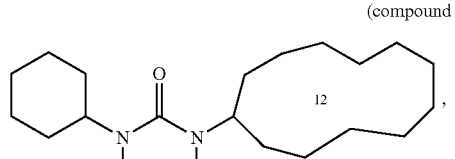
(compound no. 543)
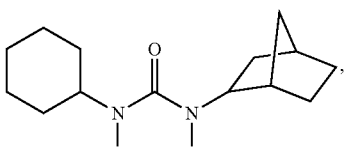
(compound no. 192)
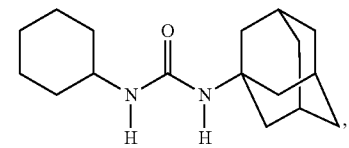
(compound no. 427)
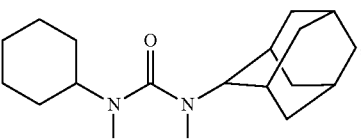
(compound no. 358)
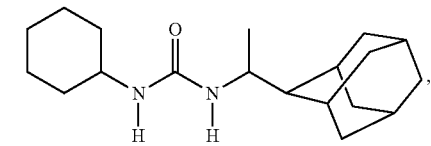
(compound no. 21)
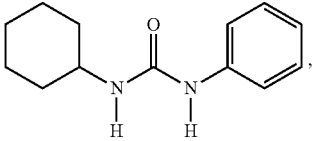
(compound no. 435)

(compound no. 270)
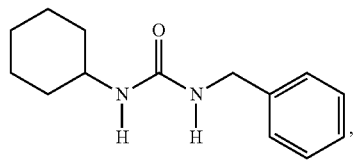
(compound no. 544)
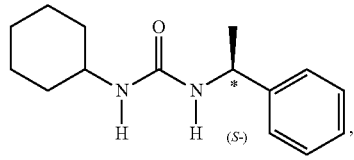
(compound no. 545)
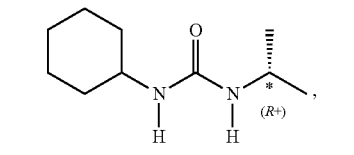
(compound no. 437)
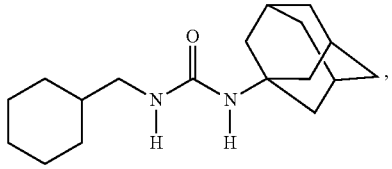
(compound no. 176)
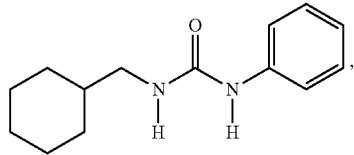
(compound no. 36)
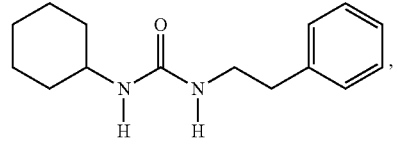
(compound no. 104)
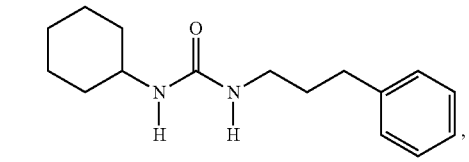
(compound no. 105)
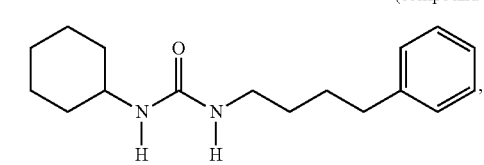
(compound no. 100)
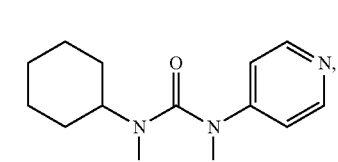
(compound no. 188)
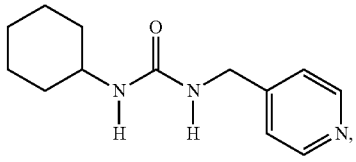
(compound no. 434)
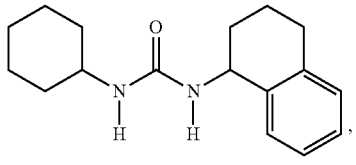
(compound no. 59)
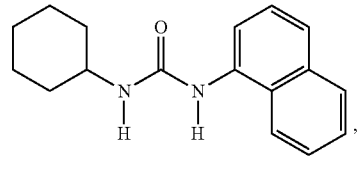
(compound no. 559)
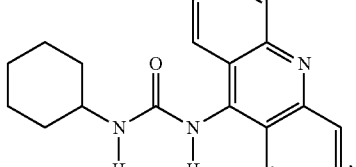
(compound no. 169)
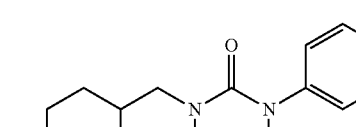
(compound no. 140)
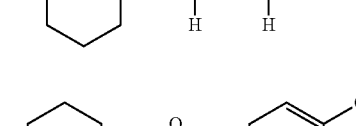
(compound no. 108)
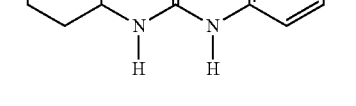
(compound no. 67)
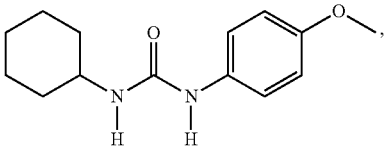
(compound no. 384)
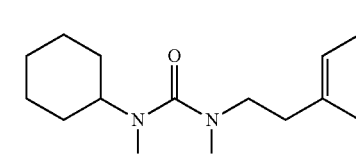

-continued
(compound no. 343)
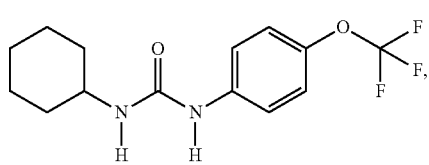
(compound no. 118)
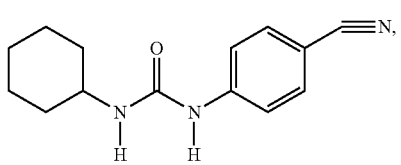
(compound no. 126)
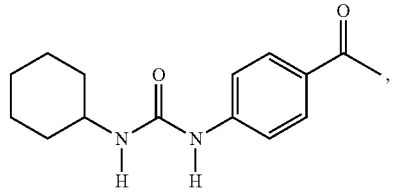
(compound no. 66)
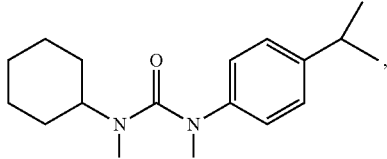
(compound no. 180)
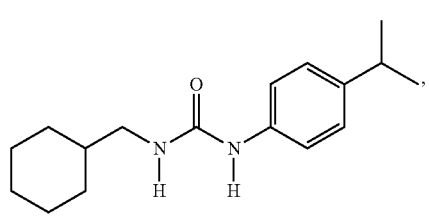
(compound no. 75)
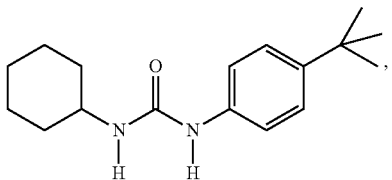
(compound no. 501)
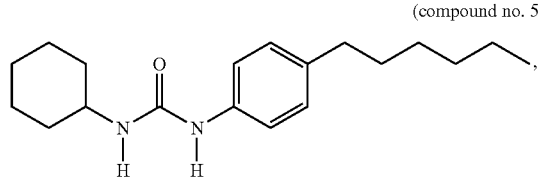
(compound no. 60)
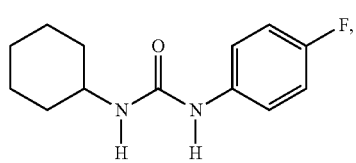
-continued
(compound no. 20)
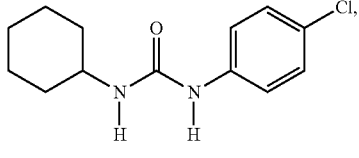
(compound no. 193)
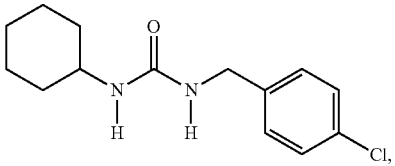
(compound no. 361)
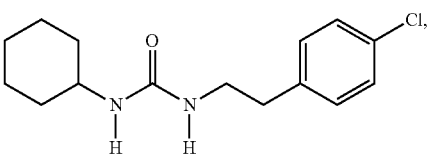
(compound no. 44)
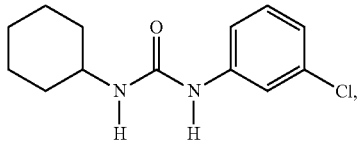
(compound no. 179)
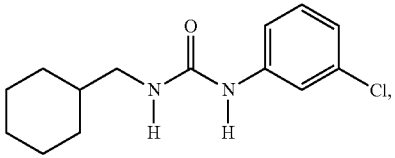
(compound no. 65)
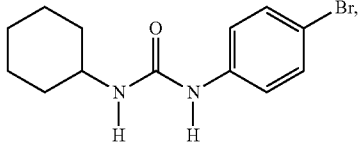
(compound no. 53)
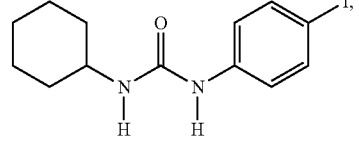
(compound no. 385)
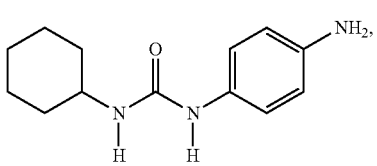
(compound no. 379)
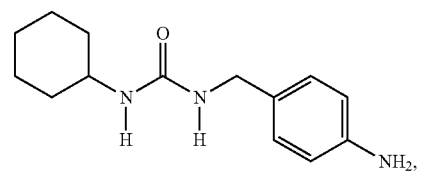

-continued
(compound no. 362)
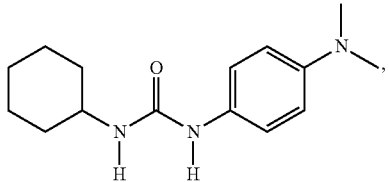
(compound no. 38)
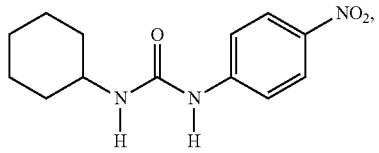
(compound no. 341)
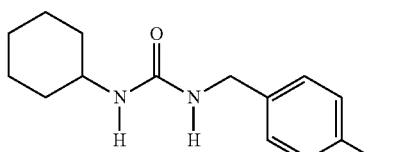
(compound no. 128)
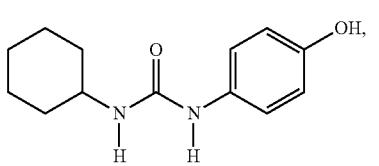
(compound no. 411)
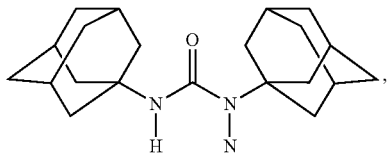
(compound no. 412)
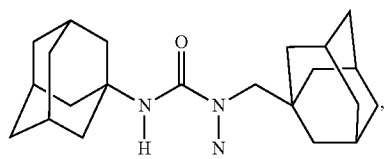
(compound no. 413)
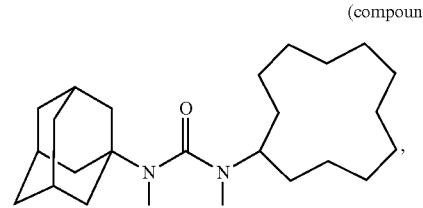
(compound no. 438)
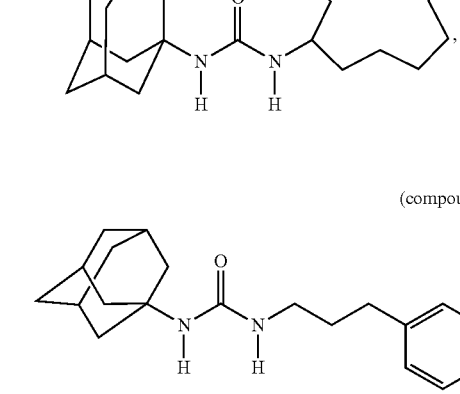
-continued
(compound no. 430)
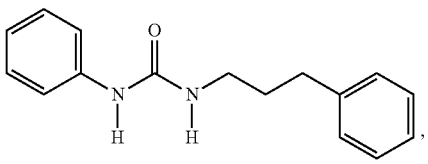
(compound no. 470)
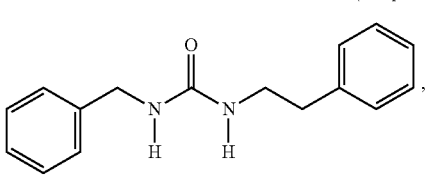
(compound no. 471)
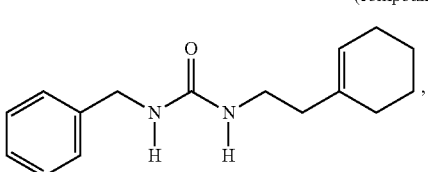
(compound no. 159)
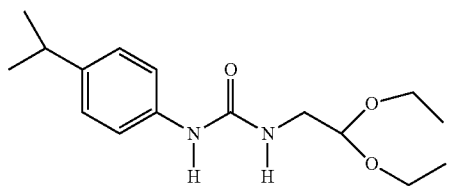
(compound no. 156)
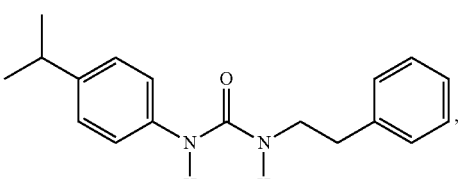
(compound no. 287)
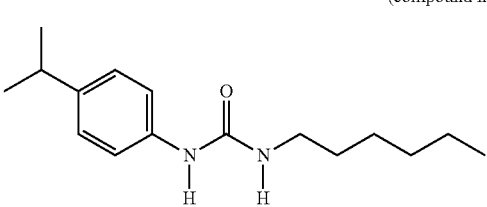
(compound no. 167)
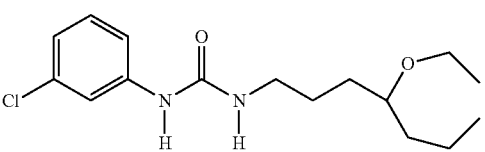 [SMILES: CCOC(CCCNC(=O)Nc1cccc(Cl)c1)OCC]
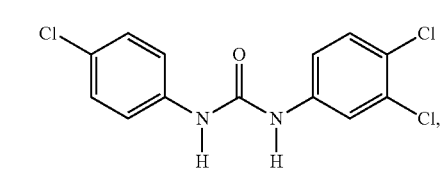

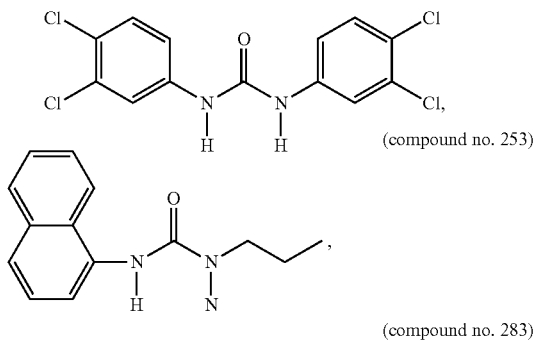

(compound no. 299)

(compound no. 253)

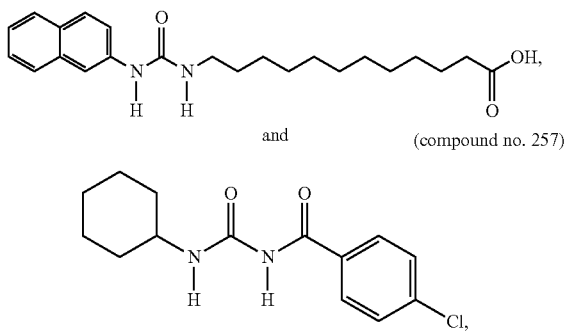

(compound no. 283)

(compound no. 257)

and or a pharmaceutically acceptable salt thereof, whereby the inflammation in the subject with ARDS is treated.

3. A method of claim 1, wherein said inflammatory disorder is systemic inflammatory response syndrome ("SIRS").

4. The method of claim 1, wherein the sEH is mammalian.

5. The method of claim 1, wherein the sEH is human.

6. The method of claim 1, wherein the inhibitor is administered orally or parentally.

7. The method of claim 1, wherein the inhibitor is administered in a total daily dose from about 0.001 µM/kg to about 100 mg/kg body weight of the patient.

8. The method of claim 1, wherein the inhibitor is formulated as a unit dosage form.

9. The method of claim 2, wherein the inhibitor is administered orally or parentally.

10. The method of claim 2, wherein the inhibitor is administered in a total daily dose from about 0.001 µM/kg to about 100 mg/kg body weight of the subject.

11. The method of claim 2, wherein the inhibitor is formulated as a unit dosage form.

* * * * *